United States Patent
Longo et al.

(10) Patent No.: US 10,660,932 B2
(45) Date of Patent: May 26, 2020

(54) DRUG COMBINATIONS AND METHODS TO STIMULATE EMBRYONIC-LIKE REGENERATION TO TREAT DIABETES AND OTHER DISEASES

(71) Applicant: UNIVERSITY OF SOUTHERN CALIFORNIA, Los Angeles, CA (US)

(72) Inventors: Valter D. Longo, Playa del Rey, CA (US); Roberta Buono, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 203 days.

(21) Appl. No.: 15/433,906

(22) Filed: Feb. 15, 2017

(65) Prior Publication Data
US 2017/0232053 A1   Aug. 17, 2017

Related U.S. Application Data

(60) Provisional application No. 62/295,422, filed on Feb. 15, 2016.

(51) Int. Cl.

| | |
|---|---|
| *A61K 38/02* | (2006.01) |
| *A23L 33/00* | (2016.01) |
| *A23L 33/10* | (2016.01) |
| *A61K 31/375* | (2006.01) |
| *A61K 31/4415* | (2006.01) |
| *A61K 31/525* | (2006.01) |
| *A61K 31/51* | (2006.01) |
| *A61K 31/4188* | (2006.01) |
| *A61K 31/07* | (2006.01) |
| *A61K 33/32* | (2006.01) |
| *A61K 33/04* | (2006.01) |
| *A61K 33/06* | (2006.01) |
| *A61K 31/519* | (2006.01) |
| *A61K 31/455* | (2006.01) |
| *A61K 33/26* | (2006.01) |
| *A61K 31/197* | (2006.01) |
| *A61K 33/34* | (2006.01) |
| *A23L 33/12* | (2016.01) |
| *A23L 33/17* | (2016.01) |
| *A23L 33/115* | (2016.01) |
| *A23L 33/16* | (2016.01) |

(Continued)

(52) U.S. Cl.
CPC .............. *A61K 38/02* (2013.01); *A23L 33/10* (2016.08); *A23L 33/115* (2016.08); *A23L 33/12* (2016.08); *A23L 33/125* (2016.08); *A23L 33/15* (2016.08); *A23L 33/155* (2016.08); *A23L 33/16* (2016.08); *A23L 33/17* (2016.08); *A23L 33/30* (2016.08); *A23L 33/40* (2016.08); *A61K 31/07* (2013.01); *A61K 31/197* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/70* (2013.01); *A61K 33/04* (2013.01); *A61K 33/06* (2013.01); *A61K 33/26* (2013.01); *A61K 33/32* (2013.01); *A61K 33/34* (2013.01); *A61K 45/06* (2013.01); *A23V 2002/00* (2013.01)

(58) Field of Classification Search
CPC ........ A61K 38/02; A61K 33/34; A61K 31/07; A61K 31/197; A61K 31/375; A61K 31/4188; A61K 31/4415; A61K 31/455; A61K 31/51; A61K 31/519; A61K 31/525; A61K 33/04; A61K 33/06; A61K 33/26; A61K 33/32; A61K 45/06; A61K 31/70; A23L 33/30; A23L 33/10; A23L 33/12; A23L 33/155; A23L 33/15; A23L 33/125; A23L 33/16; A23L 33/115; A23L 33/17; A23L 33/40; A23V 2002/00

See application file for complete search history.

(56) References Cited

U.S. PATENT DOCUMENTS

| | | |
|---|---|---|
| 8,211,700 B2 | 7/2012 | Longo |
| 8,728,815 B2 | 5/2014 | Longo |

(Continued)

FOREIGN PATENT DOCUMENTS

WO   2015153850 A2   8/2015

OTHER PUBLICATIONS

Tsuboi et a, Biochem. J., 2003, 369, 287-299 (Year: 2003).*

(Continued)

*Primary Examiner* — Sudhakar Katakam
(74) *Attorney, Agent, or Firm* — Brooks Kushman P.C.

(57) ABSTRACT

Stem cell-based therapies can potentially reverse organ dysfunction and diseases but the removal of impaired tissue and reactivation of the program leading to organ regeneration pose major challenges. In mice, a four-day fasting mimicking diet (FMD) induces a step-wise expression of Sox17 and Pdx-1, resembling that observed during pancreatic development and followed by Ngn3-driven generation of insulin-producing β-cells. FMD cycles restore insulin secretion and glucose homeostasis in both a type 2 and type 1 diabetes mouse models. In human type 1 diabetes pancreatic islets, fasting conditions reduce PKA and mTOR activity and induce Sox2 and Ngn3 expression and insulin production. The effects of the FMD are reversed by IGF-1 treatment and recapitulated by PKA and mTOR inhibition. These results indicate that a FMD promotes the reprogramming of pancreatic cells to restore insulin generation in islets from T1D patients and reverse both T1D and T2D phenotypes in mouse models.

27 Claims, 50 Drawing Sheets

(51) Int. Cl.
    *A23L 33/125*     (2016.01)
    *A23L 33/15*     (2016.01)
    *A23L 33/155*     (2016.01)
    *A61K 31/70*     (2006.01)
    *A61K 45/06*     (2006.01)

(56) References Cited

U.S. PATENT DOCUMENTS

| | | |
|---|---|---|
| 8,865,646 B2 | 10/2014 | Longo |
| 9,237,761 B2 | 1/2016 | Longo |
| 9,386,790 B2 * | 7/2016 | Longo ............... A23L 33/30 |
| 2008/0070826 A1 | 3/2008 | Selby, III |
| 2011/0118528 A1 | 5/2011 | Longo |
| 2013/0045215 A1 | 2/2013 | Longo |
| 2013/0316948 A1 | 11/2013 | Longo |
| 2014/0112909 A1 | 4/2014 | Longo |
| 2014/0328863 A1 | 11/2014 | Longo |
| 2015/0004280 A1 * | 1/2015 | Longo ............... A23L 33/30 426/2 |
| 2015/0133370 A1 | 5/2015 | Longo |
| 2015/0250771 A1 | 9/2015 | Longo |
| 2016/0303056 A1 | 10/2016 | Longo |
| 2016/0324193 A1 | 11/2016 | Longo |
| 2016/0331016 A1 | 11/2016 | Longo |
| 2017/0000183 A1 | 1/2017 | Longo |
| 2017/0027217 A1 | 2/2017 | Longo |
| 2017/0035093 A1 | 2/2017 | Longo |
| 2017/0035094 A1 | 2/2017 | Longo |

OTHER PUBLICATIONS

Fraenjek et al, Diabetes, vol. 57, Apr. 2008, 945-957 (Year: 2008).*
Zahr et al, Transplantation, vol. 84, No. 12, Dec. 27, 2007, 1576-1583 (Year: 2007).*
Brandhorst, S. et al., "Cell Metabolism," Clinical and Translational Report, V. 22, Jul. 7, 2015, pp. 86-99.
International Search Report dated May 24, 2017, PCT Appn. No. PCT/US2017/017982 filed Feb. 15, 2017, 4 pages.
U.S. Appl. No. 15/432,803, filed Feb. 14, 2017, Fasting-Mimicking Diet, 1st inventor: Valter D. Longo, 76 pgs.

* cited by examiner

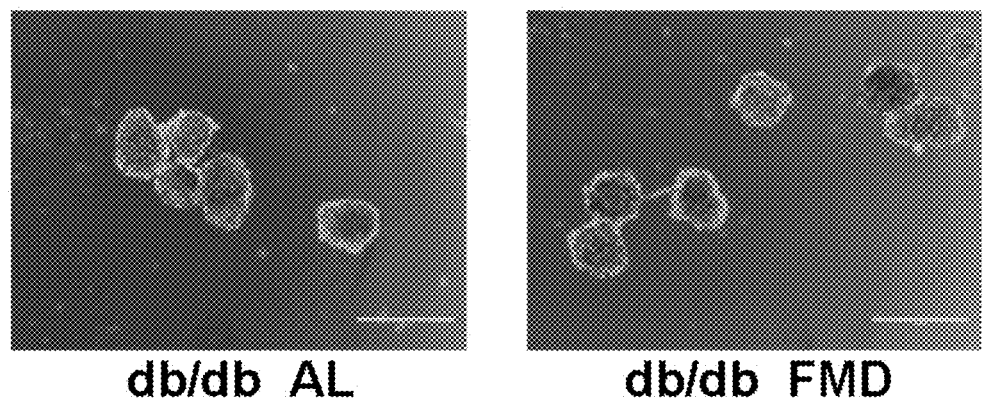
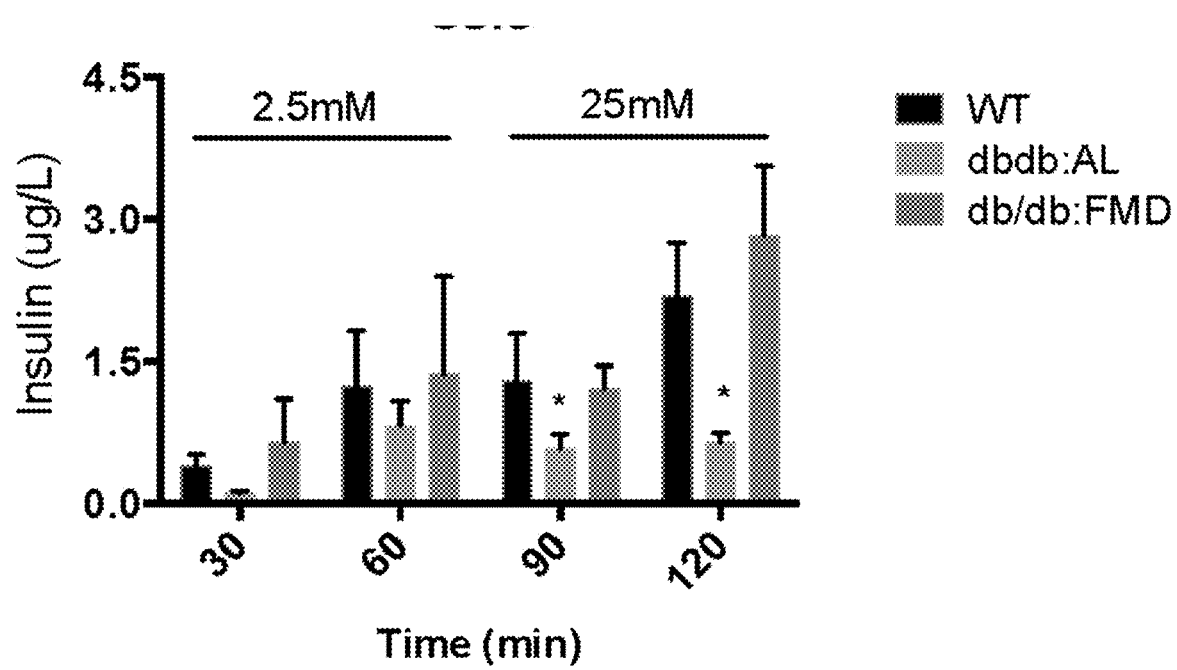
Fig. 1J

A. AL:TAM+
B. TAM before FMD
C. TAM during FMD
D. viehicle during FMD

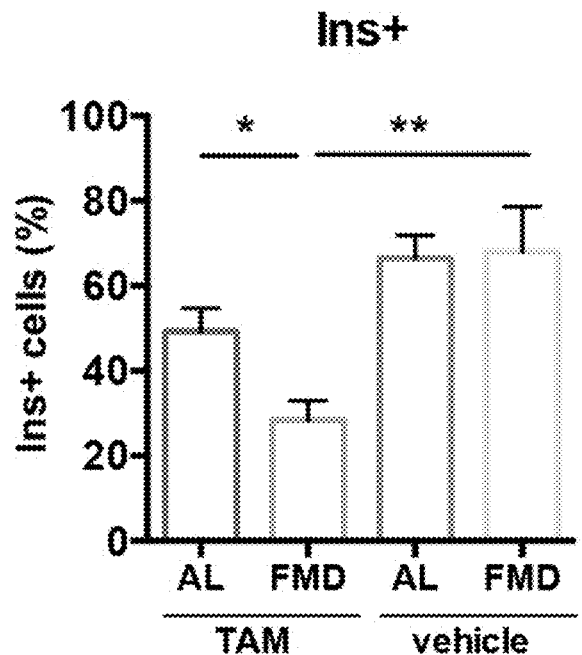
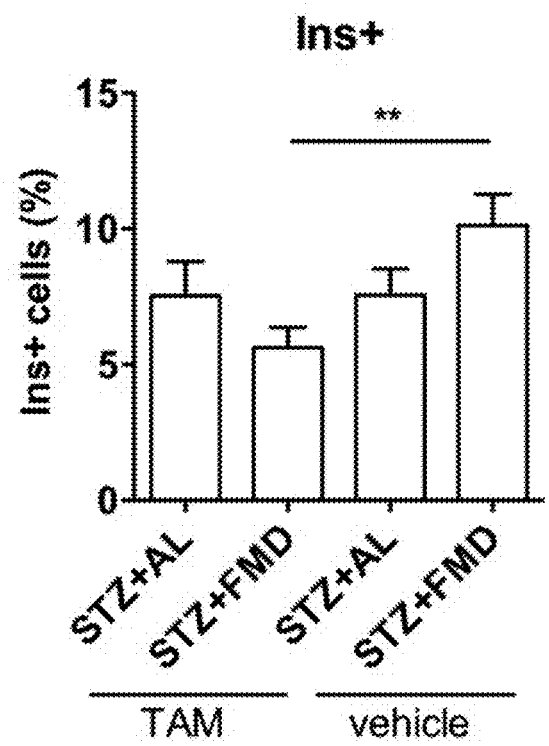
Fig. 5F

Table 1. Profile of the human subjects, related to STAR methods and Figure 6.

| Sex | Age | BMI(kg/m2) | hIGF-I (ng/ml) | | hIGF-I (%A) | | Insulin (uIU/ml) | | Glucose (mg/dl) | |
|---|---|---|---|---|---|---|---|---|---|---|
| | | | A | B | A | B | A | B | A | B |
| F | 49 | 23.0 | 125.2 | 48.4 | 100 | 39 | N/A | N/A | 83 | 72.5 |
| F | 59 | 24.7 | 141.3 | 57.4 | 100 | 41 | N/A | N/A | 85 | 90 |
| F | 28 | 22.4 | 310.0 | 112.0 | 100 | 36 | 6 | 8 | 93 | 79 |
| M | 42 | 24.7 | 177.0 | 78.0 | 100 | 44 | 1.9 | 1.9 | 112 | 96 |
| F | 68 | 18.9 | 157.3 | 70.0 | 100 | 44 | 4 | 1.9 | 101 | 84 |

Fig. 7

Table 2. Mouse FMD ingredients, related to STAR methods.

| | Day 1 (g) | Days 2-4 (g) | Note |
|---|---|---|---|
| Broth mix | 5.95 | 5.31 | The blend ratio of 3 broth mixes is 1:1:1.<br>• Vegetable Broth Mix (#60017, ABCO Laboratories, Fairfield, CA): Ingredients: Maltodextrin, Salt, Autolyzed yeast extract, Natural Flavor, Dehydrated Vegetables (tomato, onion, celery, parsley, spinach, garlic, carrot), Potato Flour, Xanthan Gum, Spices, Extractive of Spice (including turmeric), Soy Lecithin. Not more than 2% Soybean Oil added as a processing aid.<br>• Chicken Flavor Broth Mix (#60016, ABCO Laboratories, Fairfield, CA): Ingredients: Maltodextrin, Salt, Autolyzed yeast extract, Natural Flavor, Dehydrated Vegetables (onion, celery, parsley, spinach, garlic, carrot), Potato Flour, Xanthan Gum, Spices, Extractive of Spice (including turmeric), Soy Lecithin. Not more than 2% Soybean Oil added as a processing aid.<br>• Beef Flavor Broth Mix (#60024, ABCO Laboratories, Fairfield, CA): Ingredients: Maltodextrin, Salt, Autolyzed yeast extract, Natural Flavors, Dehydrated Vegetables (onion, celery, parsley, spinach, garlic, carrot), Caramel Color, Spices. |
| EVOO | 12.75 | 0 | EVOO, Bertolli Extra virgin olive oil (Mizkan American, Inc, Mount Prospect, Illinois). |
| Essential fatty acid | 0.21 | 0 | Udo's Oil, 3*6*9 (Udo's Choice) Blend Ratio Ω3:6:9 (Omega-3, alpha-linolenic acid; Omega-6, linoleic acid; Omega-9 oleic acid) is 6:3:2.5. (Flora Incorporated, Lynden, Washington). |
| Vegetable mix | 14.88 | 0 | • Beet Root powder (RM10711, The Synergy Company, Moab, Utah) (2.86 g).<br>• Carrot Root powder (RM10437, The Synergy Company, Moab, Utah) (1.86 g).<br>• Collard Leaf powder (RM10114, The Synergy Company, Moab, Utah) (1.24 g).<br>• Kale Leaf powder (RM10115, The Synergy Company, Moab, Utah) (1.24 g).<br>• Nettle Leaf powder (RM10130, The Synergy Company, Moab, Utah) (1.24 g).<br>• Spinach Leaf powder (RM10747, The Synergy Company, Moab, Utah) (2.48 g).<br>• Tomato Fruit powder (RM10409, The Synergy Company, Moab, Utah) (2.48 g).<br>• Mitake Mushroom powder (ZNature Foods, West Palm Beach, FL) (1.86 g). |
| Glycerol | 0 | 0.75 | G9012, Sigma-Aldrich, St. Louis, Missouri. |
| Hydrogel (binding agent) | 56.7 | 93.9 | Clear H2O, Westbrook, Maine. |
| Fiber | 5 | 0 | Cellulose, #3425, Bio-Serv, Flemington, New Jersey. |
| Mineral (AIN-93G-MX) | 3.5 | 0 | Teklad, TD.94046, ENVIGO. |
| Vitamin (AIN-93-VX) | 1 | 0 | Teklad, TD.94047, ENVIGO |
| Sum | *100* | *100* | |

*Fig. 8*

DRUG COMBINATIONS AND METHODS TO STIMULATE EMBRYONIC-LIKE REGENERATION TO TREAT DIABETES AND OTHER DISEASES

CROSS-REFERENCE TO RELATED APPLICATION

This application claims the benefit of U.S. provisional application Ser. No. 62/295,422 filed Feb. 15, 2016, the disclosure of which is incorporated in its entirety by reference herein.

STATEMENT REGARDING FEDERALLY SPONSORED RESEARCH OR DEVELOPMENT

The invention was made with Government support under Contract No. P01 AG034906 awarded by the National Institute of Health. The Government has certain rights to the invention.

TECHNICAL FIELD

The present invention, in general, relates to compositions and methods for: a) regenerating pancreatic cells, 2) treating diabetes. In particular, the present invention promotes pancreatic β-cell regeneration and it can be used to treat diabetes and other disorders in which cellular and tissue regeneration can lead to a reversal of the disease phenotype.

BACKGROUND

The ability of animals to survive food deprivation is an adaptive response accompanied by the atrophy of many tissues and organs to minimize energy expenditure. This atrophy and its reversal following the return to a normal diet involves stem cell-based regeneration in the hematopoietic and nervous systems (Brandhorst et al., 2015; Cheng et al., 2014). However, whether prolonged fasting and refeeding can also cause pancreatic regeneration and/or cellular reprogramming leading to functional lineage development is unknown. β cells residing in pancreatic islets are among the most sensitive to nutrient availability. Whereas Type 1 and type 2 diabetes (T1D and T2D) are characterized by β-cell dedifferentiation and trans-differentiation (Cnop et al., 2005, Dor and Glaser, Talchai et al., 2012; Wang et al.), β-cell reprogramming, proliferation and/or stepwise re-differentiation from pluripotent cells are proposed as therapeutic interventions (Baeyens et al., 2014; Chera et al., 2014; Maehr et al., 2009; Pagliuca et al., 2014; Sneddon et al., 2012; Zhou et al., 2008), suggesting that lineage-conversion is critical in both diabetes pathogenesis and therapy (Weir et al., 2013).

Although the dietary intervention with the potential to ameliorate insulin resistance and Type II diabetes have been studied extensively for decades, whether these have the potential to promote a lineage-reprogramming reminiscent of that achieved by iPSCs-based engineering remains unknown. We previously showed that cycles of prolonged fasting (2-3 days) can protect mice and humans from toxicity associated with chemotherapy and promote hematopoietic stem cell-dependent regeneration (Cheng et al., 2014; Laviano and Rossi Fanelli; Piran et al., 2014; Raffaghello et al., 2008).

Accordingly, there is an ongoing need for methods of promoting cell regeneration.

SUMMARY

In consideration of the challenges and side effects associated with prolonged fasting in humans, an embodiment of the present invention provides a low-calorie, low-protein and low-carbohydrate but high-fat 4-day fasting mimicking diet (FMD) which causes changes in the levels of specific growth factors, glucose and ketone bodies similar to those caused by fasting (Brandhorst et al., 2015)(see also FIG. 9 for metabolic cage studies).

In an embodiment, a method for promoting pancreatic β-cell regeneration and somatic cell reprogramming is provided. The method includes a step of identifying a subject in need of human pancreatic β-cell regeneration and/or somatic cell reprogramming. A fasting mimicking diet (FMD) is administered for a predetermined period of time and/or a PKA and/or Tor inhibitor to the subject to promote pancreatic β-cell regeneration and somatic cell reprogramming.

In another embodiment, a diet package for implementing the methods set forth herein is provided.

DRAWING DESCRIPTIONS

FIGS. 1A, 1B, 1C, 1D, 1E, 1F, 1G, 1H, 1I, and 1J. FMD cycles promote β-cell regeneration and reverse β-cell failure in T2D. (A) Experimental scheme to determine effects of periodic FMD on T2D in the leptin receptor deficient ($Lepr^{db/db}$) mice. Mice were monitored for hyperglycemia and insulinemia for two weeks (baseline, BL) and then distributed to the dietary groups. Each FMD cycle contains 4-day FMD and up to 10 days of refeeding (RF). During refeeding, mice received regular chow identical to that given prior to FMD and that given constantly to the ad libitum (AL) controls. (B) Plasma glucose levels and (C) Plasma insulin levels; vertical dashed lines indicate each cycle of FMD and horizontal lines indicate the range of glucose levels (mean±s.e.m) in age-matched healthy wild-type littermates. Blood samples were collected at the last refeeding day/$1^{st}$ day of the indicated cycles. Mice were fasted for 6 hours (morning fasting) for blood glucose measurements. (D) Homeostatic model assessment (HOMA) of insulin resistance (IR) and steady state β-cell function (% B) at indicated time points. HOMA-B=(20×Fasting Insulin)/(Fasting Glucose-3.5) %. (E) Glucose tolerance test and Insulin tolerance test at day 60. (F) Survival curve. mean±s.e.m,*p<0.05, Log-rank (Mantel-Cox) Test for trend. n≥16 mice per group; for (B-E), each point represents the mean±s.e.m; *p<0.05,  p<0.01, *p<0.005, two-way ANOVA. (G) Proportion of β cells per islet. (H) Proliferative proportion of β cells per islet. For (G to I), mean±s.e.m, *p<0.05,  p<0.01, *p<0.005, one-way ANOVA. (I) Immunostaining on pancreatic sections from $Lepr^{db/db}$ mice and their wild-type littermates at indicated time points. Arrow in the 8×-enlarged example image indicates a typical proliferative β cell (PCNA$^+$Insulin$^+$). Scale bar represents 50 μm. (J) Representative images for size-matched islets isolated from AL-dbdb and FMD-dbdb mice and results of glucose-stimulated insulin secretion (GSIS) test in islets isolated from $Lepr^{db/db}$ mice on FMD or fed ad libitum. Scale bar represents 50 μm. Mice are C57BL/6J background, at the age as indicated in (A), received no additional treatments other than the indicated diet. For (F-J), each point represents the mean±s.e.m; *p<0.05,  p<0.01, *p<0.005, two-way ANOVA. n≥6 mice per group, n≥15 islets per sample.

FIGS. 2A, 2B, 2C, 2D, 2E, 2F, and 2G. FMD cycles reverses STZ-induced β-cell depletion and restore glucose homeostasis. (A) Experimental scheme of periodic FMD's effects on STZ-induced T1D; Baseline measurements (BL) were performed at day 5 after STZ treatment. (B) Fasting glucose levels and (C) Plasma insulin levels during and 55 days after the FMD cycles (d5 to d35); vertical dashed lines indicate each cycle of FMD; horizontal lines (125±12 mg/dl) indicate levels of blood glucose in the naïve control mice. (D) Glucose tolerance test at d50. (E) Cytokine profile of mice treated with STZ or STZ+FMD at d30, comparing to the naïve control. Pancreatic samples collected at indicated time points were analyzed for: (F) Proliferative proportion in β cells, and proportion of insulin-producing β cells per islet and (G) Representative micrographs with immunostaining of insulin, glucagon and DAPI on pancreas sections of mice treated with STZ or STZ+FMD at the indicated time points. Scale bar represents 50 µm. Mice are C57BL/6J background, at the age 3-6 month old, received STZ treatments (150 mg/kg) as indicated in (A). For (B-G), each point represents the mean±s.e.m and sample size (n) is indicated in parentheses and for (F and G), *p<0.05, p<0.01, *p<0.005, one-way ANOVA. Ctrl, STZ-untreated control; STZ BL, baseline level of STZ treated mice at day 5. n≥6 mice per group per time point, n≥15 islets per mouse.

FIGS. 3A, 3B, 3C, 3D, and 3E. FMD and post-FMD refeeding promote β-cell proliferation and regeneration. (A) Size and number of pancreatic islets per pancreatic section. (B) Proliferative proportion of β cells and proportion of β cells per islet. (C) Representative images of pancreatic islets with Insulin, glucagon and PCNA immuno-staining. (D) Transitional cell population co-expressing both the markers of α and β cells: Proportion of α cells and Pdx1$^+$α cells. (E) Schematic of FMD- and post-FMD refeeding induced cellular changes in pancreatic islets. Mice are C57BL/6J background, at the age 3-6 month old, received no additional treatments other than the indicated diet. Pancreatic samples were collected from mice fed ad libitum (AL) or on fasting mimicking diet (FMD) at indicated time points: the end of 4d FMD (FMD), 1 day after re-feeding (RF1d) and 3 days after re-feeding (RF3d); for immunohistochemical and morphometric analysis (A to E): n≥6 mice per group, n≥30 islets per staining per time point. mean±s.e.m,*p<0.05,  p<0.01, *p<0.005, one-way ANOVA.† p<0.05, t-test.

FIGS. 4A, 4B, 4C, and 4D. Fasting mimicking diet (FMD) initiates metabolic reprogramming in pancreatic islets and stepwise redirect development of β cells in adult mice. (A) mRNA expression profile indicating changes of metabolic genes in pancreatic islets and (B) mRNA expression profile indicating changes in lineage markers in pancreatic islets, at the end of 4 d FMD (FMD) and 1 d after refeeding (RF1d), comparing the ad libitum (AL) control; *p<0.05. t-test. Heat-map generated by Qiagen RT$^2$ PCR array indicating a fold-regulation ranging from 77 (max, red) to −4 (min, green). (C) Quantification of protein expressing cells of lineage markers in pancreatic islets, from mice fed AL or on FMD at indicated time points. Protein expression was defined as a marker+ area/total islet area. See also FIG. 13B *p<0.05, p<0.01, *p<0.005. t-test comparing to AL control. (D) Representative images of immunofluorescent staining indicating stepwise transition of Sox17/Pdx1 and Pdx1/Ngn3. Scale bar represents 50 um. Mice are C57BL/5J background, at the age 3-6 month old, received no additional treatments other than the indicated diet. Pancreatic samples were collected from mice fed ad libitum (AL) or on fasting mimicking diet (FMD) at indicated time points: the end of 4 d FMD (FMD), 1 day after re-feeding (RF1d) and 3 days after re-feeding (RF3d); n=6 mice per group, ≥30 islets per marker.

FIGS. 5A, 5B, 5C, 5D, 5E, 5F, and 5G. FMD promotes Ngn3-dependent lineage reprogramming to generate insulin-producing β cells. (A) Genetic strategy used to perform lineage tracing (tdTomato) of NGN3-expressing cells in pancreas and schematic time line of tamoxifen (TAM) treatments for lineage tracing experiments. A, mice fed ad libitum were treated with TAM; B, mice receiving FMD 3 days after TAM injection; C, mice receiving TAM and FMD concurrently and D, mice receiving FMD and vehicle (corn oil) concurrently. Pancreatic tissues were collected 11 days after TAM injection to analyze the effects of FMD on Ngn3-lineage generation. Tdtomato+ cells (red, arrows) are Ngn3-derived cells; n=6 for each group. (B) Representative images of the labeled Ngn3-lineage cells (red, tdTomato) and Insulin-producing β cells (green, Ins) at indicated time-points in pancreatic islets. Left panel, scale bar represents 200 µm; right panel, scale bar represents 100 µm. (C) Quantification of total tdTomato labeled Ngn3-lineage cells per islet (top) and proportion of labeled insulin-producing β cells (ins+tdTomato+) (bottom). mean±s.e.m, p<0.01, *p<0.005, t-test. (D) Genetic strategy used to perform diphtheria toxin gene A chain (DTA)-mediated Ngn3-lineage ablation in pancreas and schematic time line of tamoxifen (TAM) treatments for lineage ablation experiments (left) and results of glucose homeostasis (right). Mice were injected with TAM prior to and after FMD, to ablate Ngn3 lineage developed and/or expanded during FMD and early refeeding (RF3d). Alternatively, mice were given additional STZ injection and then distributed into the indicated dietary groups (i.e. AL+STZ or FMD+STZ), to analyze the contribution of FMD-induced β-cell conversion in glucose homeostasis. (E) Representative images of pancreatic islets with Insulin and Pdx1 immunostaining for β cells, DAPI for nuclei. See also FIG. 13 for the images of vehicle controls. Scale bar represents 50 µm. (F) Quantification of insulin-producing β cells from Ngn3-lineage ablated mice of indicated groups. mean±s.e.m,*p<0.05, p<0.01 t-test, (top) paired t-test (bottom). n=6 for TAM and STZ, n=3 for vehicle controls. (G) Glucose levels in homeostasis and intraperitoneal glucose tolerance tests (IPGTTs) of indicated groups. mean±s.e.m,p<0.01 t-test, (top) paired t-test (bottom). n=6 for TAM and STZ, n=3 for vehicle controls. For (A) to (C), mice are ICR and B6; 12956 mixed background, at the age 3-6 month old, received the diet and/or STZ treatments indicated in (A). For (D) to (G), mice are ICR and B6; 129S6 mixed background, at the age 3-6 month old, received the diet and/or STZ treatments indicated in (D).

FIGS. 6A, 6B, 6C, 6D, 6E, 6F, 6G, 6H, 6I, 6J, and 6K. Ngn3 expression and insulin producing function of human pancreatic islets in response to fasting conditions. (A) Experimental scheme for fasting conditioning treatments on human pancreatic islet. Pancreatic islets from healthy human subject (HI) and that from T1D subjects (T1DI) were cultured separately based on manufacturer's instructions and then treated with fasting conditions (i.e. STS media, mTOR and PKA inhibitors and PKA siRNA) or control media for 36 hr. (B) Levels of hIGF-1, glucose, insulin and ketone bodies in the serum from human subjects, prior (baseline) and after receiving FMD (FMD). n=5 per group. (C) Insulin secretion capacity of HI and T1DI pre-treated with short-term starvation (STS) conditioned medium (2% FBS and 0.5 g/L glucose) and then induced with 25 mM glucose, comparing to that cultured in standard medium (STD). n=3 per group. (D) Sox2 and (E) Ngn3 expression of HI and T1DI pre-treated with STS-conditioned medium with or without administration of IGF-1 (40 ng/ml). n=6 per group. (F) Quantification of immunostaining for Ngn3 protein expression in HI and T1DI. n=5 per group. Scale bar represents 100 um. (G) Insulin gene expression, (H) PKA activities and (I) mTOR activities in HI and T1DI pretreated with STS-conditioned medium with or without administration of IGF-1 (40 ng/ml); phosphorylated versus total p70S6K ratio was used as an indicator of mTOR activities which was normalized to the levels of STD (standard medium); n=6 per group. (J and K) expression of lineage markers (Sox2 and Ngn3) of HI and T1DI treated with inhibitors dampening IGF-1 signalings; rapamycin, mTOR inhibitor; H89, PKA inhibitor and PKA siRNA. mean±s.e.m,*p<0.05,  p<0.01, *p<0.005, unpaired t-test.

FIG. 7 is Table 2 which provides Profile of the human subjects, related to STAR methods and FIG. 6.

FIG. 8 is Table 3 which provides mouse FMD ingredients, related to STAR methods.

FIGS. 9A, 9B, 9C, and 9D. S1, Related STAR methods "Diet:FMD": metabolic effects of FMD and short-term starvation (STS) on (A) body weights with lean- and fat-mass ratio prior to, after STS or FMD and 3 days after refeeding. (B) Water intake, food intake (kcal/day), Total movement and VCO2/VO2 before, during and after STS and (C) after FMD. (D) Levels of circulating insulin and ketone body (β-HB) in mice on FMD and post-FMD refeeding, comparing to that of mice under prolonged fasting (24, 36 and 60 hr). *p<0.05, p<0.01 and *p<0.005, t-test.

FIGS. 10A, 10B, 10C, 10D, 10E, 10F, and 10G. S2, Related to FIG. 1 and STAR methods. Effects of FMD in Lepr$^{db/db}$ mice. (A) Numbers of indicated cell type per islet, (B) Proliferation frequency of indicated cell type per islet, (C) Body weight and (D) Proliferation frequency and numbers and (E) example image of non-insulin/glucagon pro-ducing cells (non-α/b) and Pdx1$^+$α cells. (F) Levels of circulating insulin during IPGTT. (G) illustration of pancre-atic islet sampling. *p<0.05,  p<0.01, *p<0.005, one-way ANOVA FIGS. 11A, 11B, 11C, 11D, 11E, and 11F, Related to FIG. 2. Effects of FMD cycles on STZ-treated mice. (A) body weight, one cycle of FMD (B) Numbers of indicated cell type per islet, (C) Proliferation frequency of indicated cell type per islet, (D) Proliferation frequency of a cells and number of Pdx1$^+$α cells per islet and (E) Proliferation frequency and numbers of the non-insulin/glucagon produc-ing cells (non-α/b) and (F) Levels of circulating cytokines. *p<0.05,  p<0.01, *p<0.005,t-test.

FIGS. 12A, 12B, 12C, 12D, 12E, 12F, 12G, and 12H. related to FIG. 3. Effects of FMD and post-FMD refeeding on non-diabetic wild-type mice. (A) Number and area of pancreatic islets per pancreas section. (B) Numbers of indicated cell type per islet. (C) Proportion and (D) number of Proliferation frequency of indicated cell type per islet. (E) Number of Pdx1+α transitional cells per islet, (F) Repre-sentative images of Pdx1+α transitional cells. (G) z-stack confocal microscopy images of Gluc+ Ins+ cells (H) Pro-liferation frequency and numbers of the non-insulin/gluca-gon producing cells (non-α/b) in wild-type mice without STZ treatments. *p<0.05,  p<0.01, *p<0.005, one-way ANOVA.

Figure 13A:
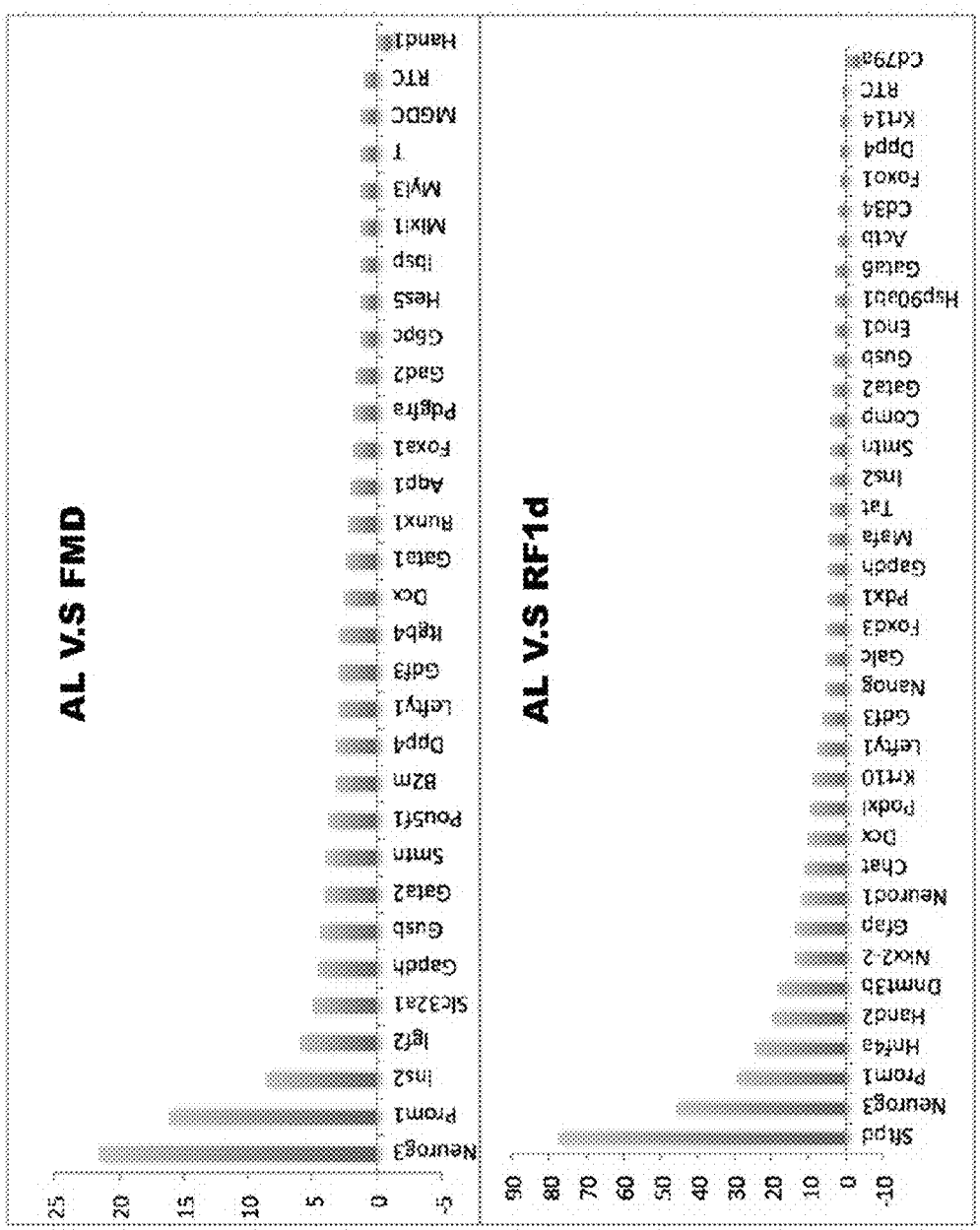
Figure 13B:
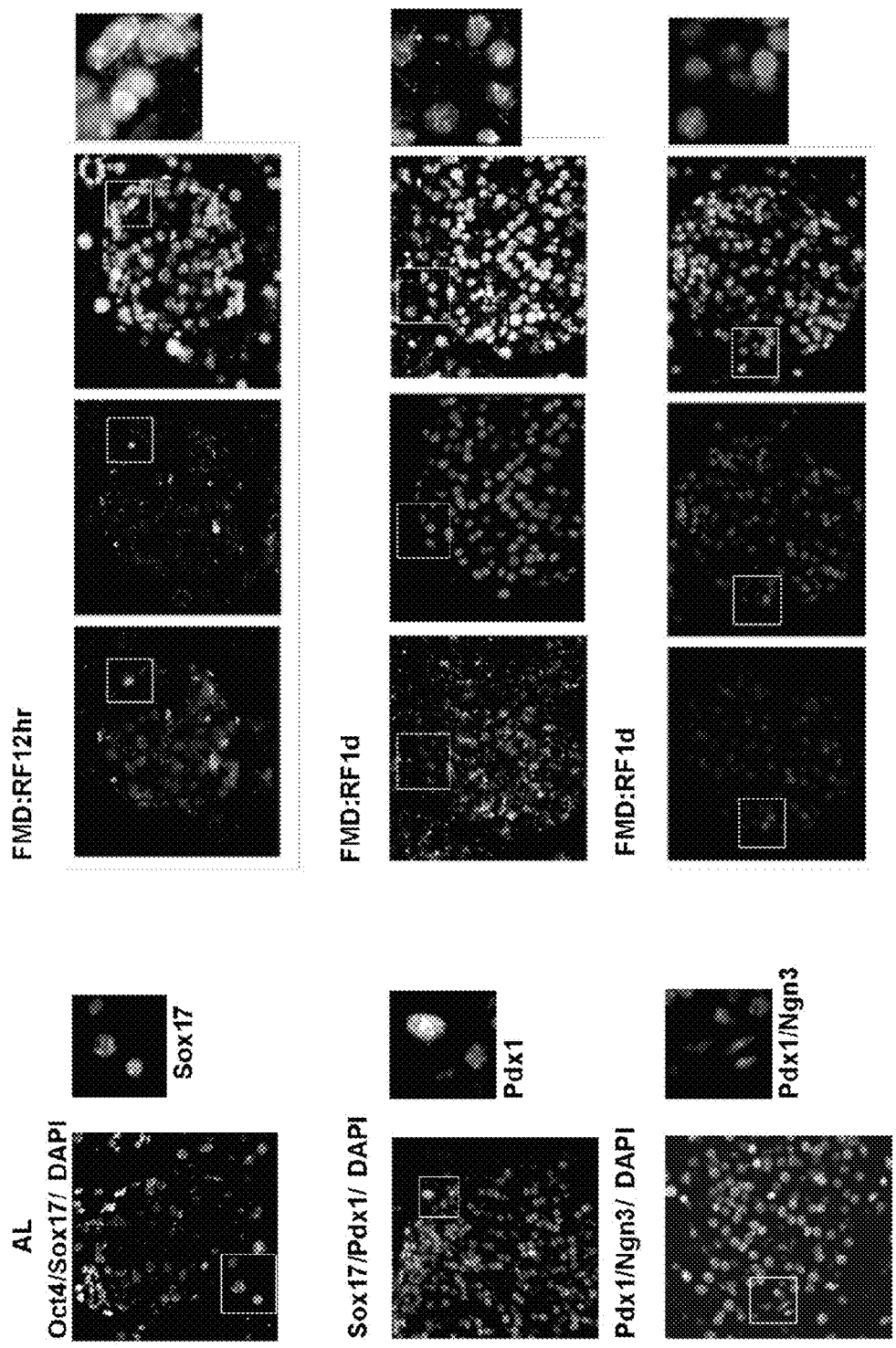
Figure 13C:
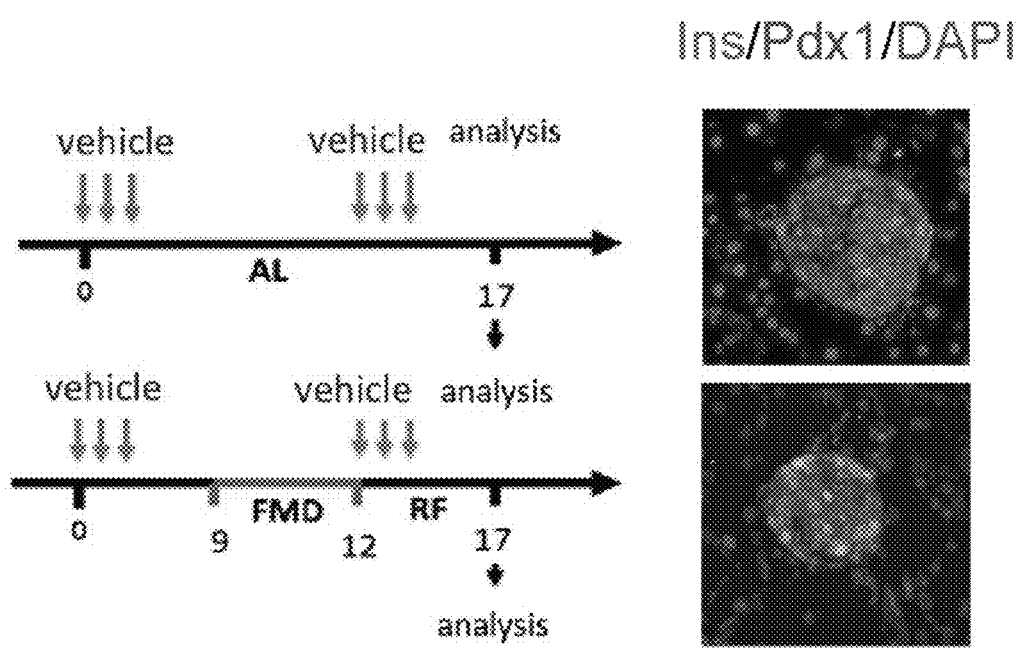

FIGS. 13A, 13B, and 13C, related to FIGS. 4 and 5. Effects of FMD on expression of developmental markers of β cell in adult mice. (A) Fold-regulation of genes signifi-cantly (*p<0.05) up-or down-regulated by FMD or RF1d comparing to AL. The p values are calculated based on a student t-test of the replicate 2^(–Delta Ct) values for each gene in the control group and treatment groups. (B) Immu-nostaining for proteins expression of lineage markers in pancreatic islets. (C) schematic time line and representative images of corn oil (vehicle control) treatments for Ngn3-lineage ablation experiments shown in FIG. 5F.

Figure 14A:
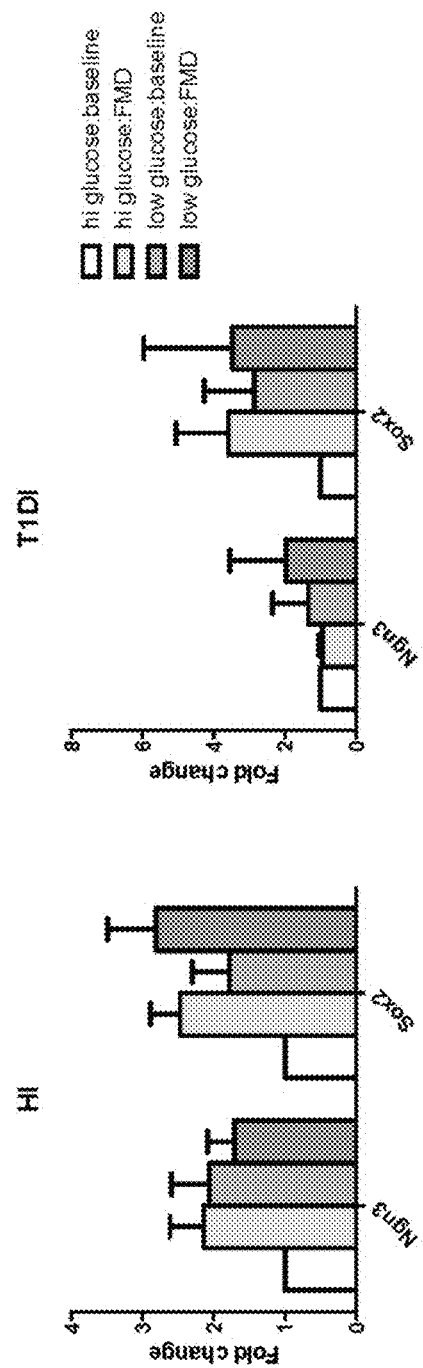
Figure 14B:
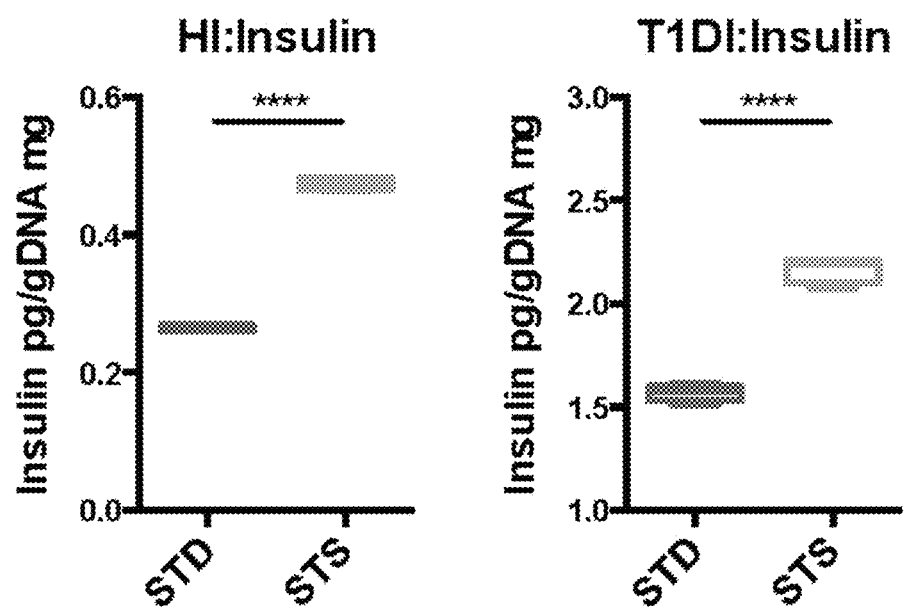

FIGS. 14A and 14B, related to FIG. 6. (A) Gene expres-sion and (B) insulin production of healthy pancreatic islets (HI) and T1DI treated with serum form subjects at indicated time points. ****p<0.0001, t-test.

DETAILED DESCRIPTION

Reference will now be made in detail to presently pre-ferred compositions, embodiments, and methods of the present invention which constitute the best modes of prac-ticing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indi-cating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of con-stituents in chemical terms refers to the constituents at the time of addition to any combination specified in the descrip-tion, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the"

comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

The terms "kilocalorie" (kcal) and "Calorie" refer to the food calorie. The term "calorie" refers to the so-called small calorie.

The term "fasting mimicking diet" (FMD) means a diet that mimics the effects of fasting typically by providing a subject with at most 50% of their normal caloric intake but with some nutritional component so that fasting is mimicked while a subject is not completely starved. Examples of useful fasting mimicking and enhancing diets and method for monitoring the effects of these diets on markers such as IGF-1 and IGFBP1 in the context of the present invention are set forth in U.S. patent application Ser. No. 14/273,946 filed May 9, 2014; Ser. No. 14/497,752 filed Sep. 26, 2014; Ser. No. 12/910,508 filed Oct. 22, 2010; Ser. No. 13/643,673 filed Oct. 26, 2012; Ser. No. 13/982,307 filed Jul. 29, 2013; Ser. No. 14/060,494 filed Oct. 22, 2013; Ser. No. 14/178,953 filed Feb. 12, 2014; Ser. No. 14/320,996 filed Jul. 1, 2014; Ser. No. 14/671,622 filed Mar. 27, 2015; the entire disclosure of these patent applications is hereby incorporated by reference. The fasting mimicking diet set forth in U.S. patent application Ser. Nos. 14/060,494 and 14/178,953 are found to be particularly useful in the present invention.

In an embodiment, a method for promoting pancreatic β-cell regeneration and somatic cell reprogramming is provided. The method includes a step of identifying a subject in need of human pancreatic β-cell regeneration and/or somatic cell reprogramming. A fasting mimicking diet (i.e. the first diet) and/or a PKA and/or Tor inhibitor is administered to the subject to promote pancreatic β-cell regeneration and somatic cell reprogramming. Examples of the PKA Tor inhibitor include, but are not limited to, an antibody, antagonist or small molecule which blocks IGF-1R; rapamycin which inhibits mTOR; H89 which inhibits PKA; and combinations thereof. The FMD is administered to the subject for a predetermined period of time. In some variations, the predetermined time period is equal to or greater than, in increasing order of preference, 3, 5, 6, or 7 days. In addition, the predetermined time period is equal to or less than, in increasing order of preference, 20, 15, 10, or 8 days. In a refinement, the predetermined time period 1, 2, 3, 4, 5, 6, 7, 8, 9, or 10 days. In another refinement, the predetermined time period is 5 to 10 days. In some variations of the methods set forth herein, the fasting mimicking and enhancing diet is repeated at predetermined intervals. For example, the fasting mimicking and enhancing diet can be initiated once a month for the duration of the subject's treatment which can be 3 months to a year or more (e.g., 1 to 5 years).

In some variations, the both the fasting mimicking diet and the PKA Tor inhibitor are administered. In other variation, the fast mimicking diet is administered while the PKA Tor inhibitor is not. In other variation, the PKA Tor inhibitor is administered while the fasting mimicking diet is not.

The administration of the fasting mimicking diet and/the PKA Tor inhibitor is found to alleviate symptoms (i.e., treat) subjects diagnosed with diabetes type 1 or diabetes type 2. In some circumstances, the administration of the fasting mimicking diet and/the PKA and/or Tor inhibitor is found to alleviate symptoms (i.e., treat) subjects identified as benefiting or needing somatic cell dedifferentiation and/or reprogramming to be promoted. In particular, gastrointestinal cell dedifferentiation and/or reprogramming can be promoted. In other circumstances, the administration of the fasting mimicking diet and/the PKA and/or Tor inhibitor is found to alleviate symptoms (i.e., treat) subjects identified as benefiting or needing promotion of muscle rejuvenation associated with stem cell generation. In still other circumstances, the administration of the fasting mimicking diet and/the PKA and/or Tor inhibitor is found to alleviate symptoms (i.e., treat) subjects identified as benefiting or needing a decrease in insulin resistance. In yet other circumstances, the administration of the fasting mimicking diet and/the PKA Tor inhibitor is found to alleviate symptoms (i.e., treat) subjects identified as benefiting or needing a reduction in hyperglycemia.

In some variations, the fasting mimicking diet for each of the methods set forth herein provides at most, in increasing order of preference, 50%, 40%, 30%, or 100% of the subject's normal caloric intake. In a refinement, the fasting mimicking diet provides at least, in increasing order of preference, 5%, 10%, or 20% of the subject's normal caloric intake. The subject's normal caloric intake is the number of kcal that the subject consumes to maintain his/her weight. The subject's normal caloric intake may be estimated by interviewing the subject or by consideration of a subject's weight. As a rough guide, subject's normal caloric intake is on average 2600 kcal/day for men and 1850 kcal/day for women. In certain instances, the fasting mimicking diet provides the subject with from 700 to 1200 kcal/day. In a particularly useful refinement, the fasting mimicking diet provides a male subject of average weight with at most 1100 kcal/day and a female subject of average weight with at most 900 kcal/day. In some refinements, the fasting mimicking diet provides at most, in increasing order of preference, 1500 kcal/day, 1400 kcal/day, 1300 kcal/day, 1200 kcal/day, 1100 kcal/day, 1000 kcal/day, 900 kcal/day, 800 kcal/day, 700 kcal/day, 600 kcal/day, 500 kcal/day, or 2500 kcal/day. In some further refinements, the fasting mimicking diet provides at least, in increasing order of preference, 0 kcal/day, 10 kcal/day, 100 kcal/day, 200 kcal/day, 300 kcal/day, 400 kcal/day, or 500 kcal/day.

In certain variations, the fasting mimicking and enhancing diet provides from 4.5 to 7 kilocalories per pound of subject for a first day (day 1) and then 3 to 5 kilocalories per pound of subject per day for the second to the final day. After a cycle of the fasting mimicking and enhancing diet, a second diet is administered to the subject for a second time period. In a refinement, the second diet provides an overall calorie consumption that is within 20 percent of a subject's normal calorie consumption for 10 to 26 days (e.g., immediately) following the fasting mimicking and enhancing diet.

The consumption guidelines for the FMD include Nutrition Facts relative to calories, macronutrients and micronutrients. Calories are consumed according to the user's body weight. Total calorie consumption is 4.5-7 calorie per pound (or 10-16 calorie per kilogram) for day 1 and 3-5 calorie per pound (or 7-11 calorie per kilogram) for day 2 to 5 and any remaining days. In a variation of the embodiments set forth above, the fasting mimicking diet provides less than 40 grams of sugar for day 1, less than 30 grams of sugar for days 2 to 5 and any remaining days, less than 28 grams of protein for day 1, less than 18 grams of protein for days 2 to 5 and any remaining days, 20-100 or 20-30 grams of monounsaturated fats or more to reach a higher calorie consumption (i.e., to reach a higher predetermined calorie consumption) for day 1, 6-30 or 6-10 grams of polyunsaturated fats or more to reach a higher calorie consumption for day 1, 2-12 grams of saturated fats or more to reach a higher calorie consumption for day 1, 10-50 or 10-15 grams of monounsaturated fats or more to reach a higher calorie consumption for days 2 to 5 and any remaining days, 3-15 or 3-5 grams of polyunsaturated fats or more to reach a higher calorie consumption for days 2 to 5 and any remaining days, 1-12 or 1-6 grams of saturated fats or more to reach a higher calorie consumption for days 2 to 5, or any remaining days, and a micronutrient composition on each day and any remaining days. To reach the higher calorie consumption described earlier which can be as high as a normal calorie intake, equal parts of the fats described above and of vegetable derived carbohydrate sources (vegetable soups and chips) described elsewhere in the patent can be used. A FMD with calories ranging from 50% restricted to normal, is expected to be effective but less effective than the 50% or more restricted diet described in this application.

In another variation of the embodiments set forth above, the fasting mimicking diet provides 8-10 kcal per kilogram body weight for each diet day. In this variation, the fasting mimicking diet provides less than 30 grams of sugar for each diet day, less than 18 grams of protein for each diet day, 9-15 grams of monounsaturated fats for each diet day, and 2.5-4.5 grams of polyunsaturated fats for each diet day and 1-5.5 grams of saturated fats for each diet day.

In still another variation of the embodiments set forth above, the fasting mimicking diet provides 5-8 kcal per kilogram body weight for each diet day. In this variation, the fasting mimicking diet provides less than 20 grams of sugar for each diet day, less than 12 grams of protein for each diet day, and 6.5-10 grams of monounsaturated fats for each diet day, 2.5-4.5 grams of polyunsaturated fats for each diet day and 1.5-4 grams of saturated fats for each diet day.

In still another variation of the embodiments set forth above, the fasting mimicking diet provides 0-3 kcal per kilogram body weight for each diet day. In this variation, the fasting mimicking diet provides less than 5 grams of sugar for each diet day, less than 3 grams of protein for each diet day, and less than 2.5 grams of monounsaturated fats for each diet day, less than 1 grams of polyunsaturated fats for each diet day and less than 1 grams of saturated fats for each diet day.

The fast mimicking diet can include virtually any source of fat, but sources high in unsaturated fat, including monounsaturated and polyunsaturated fat sources, are particularly useful. Suitable examples of monounsaturated food sources include, but are not limited to, peanut butter, olives, nuts (e.g., almonds, pecans, walnut, pistachios, cashews, macadamia), avocado, seeds (e.g., sesame), oils (e.g., olive, sesame, peanut, canola), etc. Suitable examples of polyunsaturated food sources include, but are not limited to, walnuts, seeds (e.g., pumpkin, sunflower), flaxseed, fish (e.g., salmon, tuna, mackerel), oils (e.g., safflower, soybean, corn). The first diet also includes a component selected from the group consisting of vegetable extracts, minerals, omega-3/6 essential fatty acids, and combinations thereof. In one refinement, such a vegetable extract provides the equivalent of 5 recommended daily servings of vegetables. Suitable sources for the vegetable extract include, but are not limited to, bokchoy, kale, lettuce, asparagus, carrot, butternut squash, alfalfa, green peas, tomato, cabbage, cauliflower, beets. Suitable sources for the omega-3/6 essential fatty acids include fish such as salmon, tuna, mackerel, bluefish, swordfish, and the like.

In a variation, the fasting mimicking diet includes the following micronutrients (at least 95% non-animal based): over 5,000 IU of vitamin A per day (day 1 to the final day); 60-240 mg of vitamin C per day (day 1 to the final day); 400-800 mg of Calcium per day (day 1 to the final day); 7.2-14.4 mg of Iron per day (day 1 to the final day); 200-400 mg of Magnesium per day (day 1 to the final day); 1-2 mg of copper per day (day 1 to the final day); 1-2 mg of Manganese per day (day 1 to the final day); 3.5-7 mcg of Selenium per day (day 1 to the final day); 2-4 mg of Vitamin B1 per day (day 1 to the final day); 2-4 mg of Vitamin B2 per day (day 1 to the final day); 20-30 mg of Vitamin B3 per day (day 1 to the final day); 1-1.5 mg of Vitamin B5 per day (day 1 to the final day); 2-4 mg of Vitamin B6 per day (day 1 to the final day); 240-480 mcg of Vitamin B9 per day (day 1 to the final day); 600-1000 IU of Vitamin D per day (day 1 to the final day); 14-30 mg of Vitamin E per day (day 1 to the final day); over 80 mcg of Vitamin K per day (day 1 to the final day); 16-25 mcg Vitamin B12 are provided during the entire 5-day period; 600 mg of Docosahexaenoic acid (DHA, algae-derived) are provided during the entire 5-day period. The FMED diet provides high micronutrient content mostly (i.e., greater than 50 percent by weight) from natural sources including: Kale, Cashews, Yellow Bell Pepper, Onion, Lemon Juice, Yeast, and Turmeric. Mushroom, Carrot, Olive Oil, Beet Juice, Spinach, Tomato, Collard, Nettle, Thyme, Salt, Pepper, Vitamin B12 (Cyanocobalamin), Beets, Butternut Squash, Collard, Tomato, Oregano, Tomato Juice, Orange Juice, Celery, Romaine Lettuce, Spinach, Cumin, Orange Rind, Citric Acid, Nutmeg, Cloves, and combinations thereof. Table 1 provides an example of additional micronutrient supplementation that can be provided in the FMD diet:

TABLE 1

Micronutrient Supplementation

| | Supplement | Formula | Amount | Amount Range | Unit |
|---|---|---|---|---|---|
| Vit A | | | 1250 IU | 900-1600 | IU |
| Vit C | Ascorbic Acid | $C_6H_8O_6$ | 15.0000 | 10-20 | mg |
| Ca | Calcium Carbonate | $CaCO_3$ | 80.0000 | 60-100 | mg |
| Fe | Ferrous Fumarate | $C_4H_2FeO_4$ | 4.5000 | 3-6 | mg |
| Vit D3 | Cholecalciferol | $C_{27}H_{44}O$ | 0.0025 | 0.001-0.005 | mg |
| Vit E | dl-Alpha Tocopheryl Acetate | $C_{29}H_{50}O_2$ | 5.0000 | 3-7 | mg |
| Vit K | Phytonadione | | 0.0200 | 0.1-0.04 | mg |
| Vit B1 | Thiamine Mononitrate | $C_{12}H_{17}N_5O_4S$ | 0.3750 | 0.15-0.5 | mg |
| Vit B2 | Riboflavin E101 | $C_{17}H_{20}N_4O_6$ | 0.4250 | 0.2-0.6 | mg |

TABLE 1-continued

Micronutrient Supplementation

| | Supplement | Formula | Amount | Amount Range | Unit |
|---|---|---|---|---|---|
| Vit B3 | Niacinamide | $C_6H_6N_2O$ | 5.0000 | 3-7 | mg |
| Vit B5 | Calcium Pantothenate | $C_{18}H_{32}CaN_2O_{10}$ | 2.5000 | 1.5-4.0 | mg |
| Vit B6 | Pyridoxine Hydrochloride | $C_8H_{11}NO_3 \cdot HCl$ | 0.5000 | 0.3-0.7 | mg |
| Vit B7 | Biotin | $C_{10}H_{16}N_2O_3S$ | 0.0150 | 0.01-0.02 | mg |
| Vit B9 | Folic Acid | $C_{19}H_{19}N_7O_6$ | 0.1000 | 0.07-0.14 | mg |
| Vit B12 | Cyanocobalamin | $C_{63}H_{88}CoN_{14}O_{14}P$ | 0.0015 | 0.001-0.002 | mg |
| Cr | Chromium Picolinate | $Cr(C6H4NO2)3$ | 0.0174 | 0.014-0.022 | mg |
| Cu | Cupric Sulfate | $CuSO4$ | 0.2500 | 0.18-0.32 | mg |
| I | Potassium Iodide | KI | 0.0375 | 0.03-0.045 | mg |
| Mg | Magnesium Oxide | MgO | 26.0000 | 20-32 | mg |
| Mn | Manganese Sulfate | $MnSO_4$ | 0.5000 | 0.3-0.7 | mg |
| Mo | Sodium Molybdate | $Na_2MoO_4$ | 0.0188 | 0.014-0.023 | mg |
| Se | Sodium Selenate | $Na_2O_4Se$ | 0.0175 | 0.014-0.023 | mg |
| Zn | Zinc Oxide | ZnO | 3.7500 | 3-5 | mg |

In some variations, a second diet is administered to the subject for a second time period. The second diet provides an overall calorie consumption that is within 10 percent of a subject's normal calorie consumption. Although the present invention is not significantly limited by the second time period, the second time period can be from 7 days to 6 months or longer. Typically, the second diet can be administered for 25 to 26 days or longer following the fasting mimicking and enhancing diet. In some refinements, the second diet provides at most, in increasing order of preference, 2500 kcal/day, 2400 kcal/day, 2300 kcal/day, 2200 kcal/day, 2100 kcal/day, 2000 kcal/day, 1900 kcal/day, 1800 kcal/day, 1700 kcal/day, 1600 kcal/day, or 1500 kcal/day. In some further refinements, the second diet provides at least, in increasing order of preference, 1200 kcal/day, 1300 kcal/day, 1400 kcal/day, 1500 kcal/day, 1600 kcal/day, 1700 kcal/day, or 1800 kcal/day.

In another embodiment, a diet package for promoting pancreatic β-cell regeneration and somatic cell reprogramming is provided. In a variation, the diet includes the caloric, food and nutritional specification set forth above in accordance to the methods and administration schedule set forth above. For example, the diet package includes a first set of rations for a first diet to be administered for a predetermined time period to a subject with administration schedule. The first diet providing less than 40 grams of sugar for day 1; less than 30 grams of sugar for days 2 to 5 and any remaining days; less than 28 grams of protein for day 1; less than 18 grams of protein for days 2 to 5 and any remaining days; 20-100 or 20-30 grams of monounsaturated fats or more to reach the higher calorie intake for day 1; 6-30 or 6-10 grams of polyunsaturated fats or more to reach the higher calorie intake for day 1; 2-12 grams of saturated fats or more to reach the higher calorie intake for day 1; 10-50 or 10-15 grams of monounsaturated fats or more to reach the higher calorie intake for days 2 to 5 and any remaining days; 3-15 or 3-5 grams of polyunsaturated fats or more to reach the higher calorie intake for days 2 to 5 and any remaining days; 1-30 or 1-6 grams of saturated fats or more to reach the higher calorie intake for days 2 to 5, or any remaining days; and a micronutrient composition on each day and any remaining days. In a refinement, the diet package also includes instructions for administering the fasting mimicking diet in accordance to the methods herein, and in particular, instructions for administering the diet package to a subject for promoting pancreatic β-cell regeneration and somatic cell reprogramming with the instructions including the administration schedule. To reach the higher calorie consumption described earlier which can be as high as a normal calorie intake, equal parts of the fats described above and of vegetable derived carbohydrate sources (vegetable soups and chips) described elsewhere in the patent can be used. A FMD with calories ranging from 50% restricted to normal, is expected to be effective but less effective than the 50% or more restricted diet described in this application.

In a variation, the fasting mimicking diet of the diet package provides 8-25 or 8-10 kcal per kilogram body weight for each diet day; less than 30 grams of sugar for each diet day; less than 18 grams of protein for each diet day; and 9-30 or 9-15 grams of monounsaturated fats for each diet day, 2.5-9 or 2.5-4.5 grams of polyunsaturated fats for each diet day and 1-10 or 1-5.5 grams of saturated fats for each diet day. In another variation, the fasting mimicking diet of the diet package provides 5-8 kcal per kilogram body weight for each diet day; less than 20 grams of sugar for each diet day; less than 12 grams of protein for each diet day; and 6.5-10 grams of monounsaturated fats for each diet day, 2.5-4.5 grams of polyunsaturated fats for each diet day and 1.5-4 grams of saturated fats for each diet day. In still another variation, the diet package provides 0-3 kcal per kilogram body weight for each diet day; less than 5 grams of sugar for each diet day; less than 3 grams of protein for each diet day; and less than 2.5 grams of monounsaturated fats for each diet day, less than 1 grams of polyunsaturated fats for each diet day and less than 1 grams of saturated fats for each diet day.

The first set of rations can also provide 400-800 mg of calcium per day for days 1-5; 7.2-14.4 mg of iron per day for days 1-5; 200-400 mg of magnesium per day for days 1-5; 1-2 mg of copper per day for days 1-5; 1-2 mg of manganese per day for days 1-5; and 3.5-7 mcg of selenium per day for days 1-5. In a refinement, the first set of rations provides 2-4 mg of Vitamin B1 per day for days 1-5; 2-4 mg of Vitamin B2 per day for days 1-5; 20-30 mg of Vitamin B3 per day for days 1-5; 1-1.5 mg of Vitamin B5 per day for days 1-5; 2-4 mg of Vitamin B6 per day for days 1-5; 240-480 mcg of Vitamin B9 per day for days 1-5; 600-1000 IU of Vitamin D per day for days 1-5; 14-30 mg of Vitamin E per day for days 1-5; over 80 mcg of Vitamin K per day for days 1-5; and 16-25 mcg Vitamin B12 are provided during the predetermined time period. In a further refinement, the first set of rations provides 600 mg of Docosahexaenoic acid (DHA, algae-derived) during the predetermined time period. In a refinement the first set of rations also provides a component having Vitamin A in an amount of 900-1600 IU; Ascorbic Acid in an amount of 10-20 mg; calcium carbonate in an amount of 60-100 mg; ferrous fumarate in an amount of 3-6 mg; cholecalciferol in an amount of 0.001-0.005 mg; dl-alpha tocopheryl acetate in an amount 3-7 mg; phytonadione in an amount of 0.1-0.04 mg; thiamine mononitrate in an amount of 0.15-0.5 mg; riboflavin in an amount 0.2-0.6 mg; and niacinamide in an amount of 3-7 mg. In a refinement the first set of rations also provides a component having calcium pantothenate in an amount of 1.5-4.0 mg; pyridoxine hydrochloride in an amount of 0.3-0.7 mg; biotin in an amount of 0.01-0.02 mg; folic acid in an amount of 0.07-0.14 mg; cyanocobalamin in an amount of 0.001-0.002 mg; chromium picolinate in an amount of 0.014-0.022 mg; cupric sulfate in an amount of 0.18-0.32 mg; potassium iodide in an amount of 0.03-0.045 mg; magnesium oxide in an amount of 20-32 mg; manganese sulfate of 0.3-0.7 mg; sodium molybdate in an amount of 0.014-0.023 mg; sodium selenate in an amount of 0.014-0.023 mg; and zinc oxide in an amount of 3-5 mg.

In some variations, the diet package includes a second set of rations for a second diet to be administered to the subject for a second time period. The second diet providing an overall calorie consumption that is within 10 percent of a subject's normal calorie consumption for 25 to 26 days following the first diet. In particular, the second diet provides the caloric, food and nutritional specification for a subject's normal diet as set forth above.

A particularly useful version of the fasting mimicking diet is disclosed in U.S. patent application Ser. No. 15/432,803 filed on Feb. 14, 2017; the entire disclosure of which is hereby incorporated by references. In particular, a diet package with certain specific meal components for implementing a fasting mimicking diet in the method set forth herein is provided. In a refinement, the diet package also includes instruction for administering the fasting mimicking diet in accordance to the methods herein, and in particular, instructions for administering the diet package to a subject for promoting pancreatic β-cell regeneration and somatic cell reprogramming with the instructions including the administration schedule. In one variation, the fasting mimicking diet package and its associated fasting mimicking diet provide daily meal portions for a predetermined number of days are set forth above (e.g., 1, 2, 3, 4, 5, 6, 7, 8, 9, or 10 days). The fasting mimicking diet package includes a kale cracker composition, a first vegetable broth composition, a mushroom soup composition, a tomato soup composition, a quinoa-containing minestrone soup composition, a bean-containing minestrone soup composition, and a pumpkin soup composition. Characteristically, the daily meal portions are packaged into meal servings or into a total daily serving to be divided into meals. In a refinement, the fasting mimicking diet package and its associated fasting mimicking diet further includes a nut-containing nutrition bar, a cocoa-containing nutrition bar, a first olive-containing composition, a first vegetable broth composition, a tea composition that includes spearmint, a energy drink composition, a micronutritional composition, and a algal oil composition. In a further refinement, the fasting mimicking diet package and its associated fasting mimicking diet further includes a second olive-containing composition, a second vegetable broth composition, a tea composition that includes spearmint and lemon, and a tea composition that includes hibiscus. It should be appreciated that each of the soup, broth, tea and energy compositions set forth herein are designed to have added water when consumed.

In another variation of a fasting mimicking diet package, diet package includes a nut-containing nutrition bar, a cocoa-containing nutrition bar, a first olive-containing composition, a kale cracker composition, a vegetable soup composition, a first vegetable broth composition, a tea composition that includes spearmint, a energy drink composition, a micronutritional composition, and a algal oil composition. Characteristically, the daily meal portions are packaged into meal servings or into a total daily serving to be divided into meals. This diet package also includes daily meal portions for a predetermined number of days as set forth above with the daily meal portions being packaged into meal servings or into a total daily serving to be divided into meals. In a refinement, the fasting mimicking diet package further includes a mushroom soup composition, a tomato soup composition, a quinoa-containing minestrone soup composition, and a pumpkin soup composition. In a further refinement, the fasting mimicking diet package further includes a second olive-containing composition, a second vegetable broth composition, a bean-containing minestrone soup composition, a tea composition that includes spearmint and lemon, and a tea composition that includes hibiscus.

As set forth above, the fasting mimicking diet packages includes specific meal components that are administered for the fasting mimicking diet. Typically, compositions are as follows. The nut-containing nutrition bar includes almond meal and macadamia nuts. The cocoa-containing nutrition bar includes almond butter, almonds, and brown rice crispy (e.g., brown puffed rice). The mushroom soup composition includes brown rice powder, carrots, inulin, and mushrooms. The bean-containing minestrone soup composition includes white beans, cabbage, and potatoes. The first vegetable broth composition includes carrots, maltodextrin, celery, spinach, and tomatoes. The second vegetable broth composition includes carrots, maltodextrin, celery, spinach, soy lecithin, and tomatoes. The energy drink composition includes glycerin and water. The algal oil composition includes schizocatrium algae oil. The micronutrient composition includes beet root powder, calcium carbonate, carrots, collard leaf, kale leaf, and tomatoes. In a refinement, the micronutrient composition includes Vit A, Vit C, Ca, Fe, Vit D3, Vit E, Vit K, Vit B1, Vit B2, Vit B3, Vit B5, Vit B6, Vit B7, Vit B9, Vit B12, Cr, Cu, I, Mg, Mn, Mo, Se, and Zn.

In a refinement, the nut-containing nutrition bar (L-Bar Nut based) includes almond meal and macadamia nuts. In a refinement, the nut-containing nutrition bar (L-Bar Nut based) includes almond meal preferably in an amount of 20 to 35 weight %; coconut preferably in an amount of 2 to 10 weight %; coconut oil preferably in an amount of 1 to 8 weight %; flax seed meal preferably in an amount of 1 to 8 weight %; honey preferably in an amount of 10 to 30 weight %; macadamia nuts preferably in an amount of 10 to 30 weight %; pecans preferably in an amount of 10 to 25 weight %; salt preferably in an amount of 0.1 to 0.8 weight %; and optionally vanilla preferably in an amount of 0.3 to 1.5 weight %.

In a refinement, the cocoa-containing nutrition bar (L-Bar ChocoCrisp) includes almond butter, almonds, and brown rice crispy (PGP10235). In a refinement, the cocoa-containing nutrition bar (L-Bar ChocoCrisp) includes almond butter preferably in an amount of 10 to 25 weight %; almonds preferably in an amount of 3 to 12 weight %; brown rice crispy (PGP10235) preferably in an amount of 10 to 25 weight %; brown rice syrup preferably in an amount of 2 to 8 weight %; chocolate liquor preferably in an amount of 1 to 4 weight %, cocoa butter preferably in an amount of 0.4 to 1.6 weight %; cocoa powder preferably in an amount of 4 to 12 weight %; fiber syrup SF75 preferably in an amount of 18 to 38 weight %, flax seed oil preferably in an amount of 1 to 3 weight %; salt preferably in an amount of 0.1 to 0.4 weight % and sugar preferably in an amount of 1 to 6 weight %.

In a refinement, the first olive-containing composition (sea salt version) includes olives, olive oil, and sea salt. In a refinement, the first olive-containing composition (sea salt) includes lactic acid preferably in an amount of 0.3 to 1 weight %; oil (olive) preferably in an amount of 2 to 6 weight %; olives (raw, green pitted) preferably in an amount of 50 to 97 weight %; salt (reg., kosher, sea salt) preferably in an amount of 0.8 to 3 weight %; and thyme preferably in an amount of 0.1 to 0.5 weight %.

In a refinement, the second olive-containing composition (garlic version) includes olives, olive oil, and garlic. In a refinement, the second olive-containing composition (garlic) includes garlic preferably in an amount of 0.1 to 0.6 weight %; lactic acid preferably in an amount of 0.3 to 1 weight %; oil (olive) preferably in an amount of 2 to 6 weight %; olives (raw, green pitted) preferably in an amount of 50 to 97 weight %; salt (reg., kosher, sea salt) preferably in an amount of 0.8 to 3 weight %; thyme preferably in an amount of 0.1 to 0.5 weight %.

In a refinement, the kale cracker composition includes kale, almonds, tapioca flour, and optionally sesame seeds. In another refinement, the kale cracker composition includes almonds preferably in an amount of 15 to 40 weight %; black pepper preferably in an amount of 0.1 to 0.4 weight %; chia seeds preferably in an amount of 3 to 10 weight %; chili pepper preferably in an amount of 0.4 to 1.2 weight %; cumin seeds preferably in an amount of 0.3 to 0.9 weight %; flax seeds preferably in an amount of 3 to 10 weight %; garlic preferably in an amount of 0.02 to 0.04 weight %; kale preferably in an amount of 2 to 6 weight %; oil (sun flower) preferably in an about of 2 to 7 weight %; onion (powder, minced) typically in an amount of 0.3 to 0.9 weight %; oregano preferably in an amount of 0.01 to 0.06 weight %; salt preferably in an amount of 1 to 4 weight %; sesame seeds preferably in an amount of 15 to 35 weight %; sugar (coconut) preferably in an amount of 1 to 5 weight %; tapioca flour preferably in an amount of 10 to 30 weight %; vinegar (coconut) preferably in an amount of 1 to 4 weight %; water (purified) preferably in an amount of 2 to 12 weight %; and yeast extract preferably in an amount of 0.3 to 1 weight %.

In another refinement, the kale cracker composition includes kale, flax seeds golden, sesame seeds, and sunflower seeds. In another refinement, the apple cider vinegar preferably in an amount 1 to 3 weight %; black pepper preferably in an amount of 0.4 to 1.3 weight %; cashews preferably in an amount of 4 to 13 weight %; dill weed preferably in an amount of 0.4 to 1.3 weight %; flax seeds golden preferably in an amount of 13 to 40 weight %; hemp seeds preferably in an amount of 0.7 to 2 weight %; kale preferably in an amount of 14 to 42 weight %; onion, white, dried, (powder, minced) preferably in an amount of 0.5 to 1.6 weight %; pumpkin seeds preferably in an amount of 0.7 to 2 weight %; salt (reg., kosher, sea salt) preferably in an amount of 0.7 to 2 weight %; Sesame seeds preferably in an amount of 2 to 8 weight %; sunflower seeds preferably in an amount of 10 to 30 weight %; and yeast extract preferably in an amount of 1 to 5 weight %.

In a refinement, the vegetable soup composition includes onions, tomatoes, spinach, green tree extract, optionally rice flour, optionally brown rice powder, optionally carrots, and optionally inulin, leeks, In a refinement, the vegetable soup composition includes basil (whole leaf, dried) preferably in an amount of 0.3 to 0.9 weight %; brown rice powder (whole grain) preferably in an amount of 3 to 12 weight %; carrot (dehydrated, puffed, powder, pieces) preferably in an amount of 4 to 14 weight %; green tea extract preferably in an amount of 0.02 to 0.06 weight %; inulin preferably in an amount of 5 to 15 weight %; leeks (granules −10+40) preferably in an amount of 1 to 5 weight %; oil (olive) preferably in an amount of 1 to 6 weight %; onion (powder, minced) preferably in an amount of 4 to 15 weight %; parsley preferably in an amount of 0.3 to 0.8 weight %; red bell peppers preferably in an amount of 1 to 5 weight %; rice flour preferably in an amount of 18 to 50 weight %; salt preferably in an amount of 2 to 7 weight %; spinach (leaf, powder) preferably in an amount of 0.4 to 1.5 weight %; tomatoes (fruit powder, sun dried, granules) preferably in an amount of 4 to 14 weight %; yeast extract preferably in an amount of 0.5 to 1.8 weight %. In the vegetable soup composition and any of the compositions set forth herein having rice flour, the rice flour can be glutinous or non-glutinous, milled or unmilled.

In another refinement, the vegetable soup composition includes carrots, inulin, leeks, onions and rice flour. In a refinement, the vegetable soup composition includes basil, whole leaf, dried preferably in an amount of 0.3 to 1 weight %; carrot (dehydrated, puffed, powder, pieces) preferably in an amount of 4 to 12 weight %; inulin preferably in an amount of 6 to 18 weight %; leeks in an amount of 1 to 5 weight %; oil (olive) preferably in an amount of 1 to 3 weight %; Onion, white, dried, (powder, minced) preferably in an amount of 10 to 30 weight %; parsley preferably in an amount of 0.3 to 1 weight %; potato preferably in an amount of 1 to 5 weight %; red pepper preferably in an amount of 1 to 6 weight %; rice flour in an amount of 13 to 40 weight %; salt (reg., kosher, sea salt) in an amount of 4 to 12 weight %; spinach (leaf, powder) preferably in an amount of 0.2 to 1 weight %; and tomatoes, (fruit powder, sun dried granules) preferably in an amount of 3 to 13 weight %.

In a refinement, the mushroom soup composition includes mushrooms, green tea extract, optionally brown rice powder, optionally carrots, and optionally inulin. In a refinement, the mushroom soup composition includes brown rice powder (whole grain) preferably in an amount of 10 to 30 weight %; carrot (dehydrated, puffed, powder, pieces) preferably in an amount of 3 to 12 weight %; green tea extract preferably in an amount of 0.02 to 0.06 weight %; inulin preferably in an amount of 3 to 12 weight %; mushrooms (European mix, powder, pieces) preferably in an amount of 6 to 18 weight %; oil (olive) preferably in an amount of 1 to 6 weight %; onion preferably in an amount of powder, minced) preferably in an amount of 3 to 12 weight %; parsley preferably in an amount of 0.1 to 0.5 weight %; rice flour preferably in an amount of 18 to 50 weight %; salt preferably in an amount of 2 to 8 weight %; yeast extract preferably in an amount of 0.5 to 1.5 weight %.

In another refinement, the mushroom soup composition includes carrots, inulin, mushrooms, onions, and rice flour. In another refinement, the mushroom soup composition includes carrot (dehydrated, puffed, powder, pieces) preferably in an amount of 7 to 22 weight %; inulin preferably in an amount of 7 to 22 weight %; mushrooms (European mix), (powder & pieces) dehydrated preferably in an amount of 7 to 22 weight %; oil (olive) preferably in an amount of 0.6 to 2 weight %; Onion, white, dried, (powder, minced) preferably in an amount of 7 to 22 weight %; parsley preferably in an amount of 0.3 to 0.9 weight %; potato preferably in an amount of 0.6 to 2 weight %; rice flour preferably in an amount of 15 to 45 weight %; salt (reg., kosher, sea salt) preferably in an amount of 6 to 18 weight %; and yeast extract preferably in an amount of 0.7 to 2.2 weight %.

In a refinement, the tomato soup composition includes tomatoes, green tea extract, optionally inulin, and optionally onions. In a refinement, the tomato soup composition (new) includes basil (whole leaf, dried) preferably in an amount of 0.2 to 0.7 weight %; brown rice powder (whole grain) preferably in an amount of 1 to 5 weight %; green tea extract preferably in an amount of 0.02 to 0.06 weight %; inulin preferably in an amount of 7 to 20 weight %; oil (olive) preferably in an amount of 3 to 9 weight %; onion preferably (powder, minced) preferably in an amount of 4 to 12 weight %; parsley preferably in an amount of 0.1 to 0.6 weight %; rice flour preferably in an amount of 18 to 50 weight %; salt preferably in an amount of 2 to 9 weight %; tomatoes (fruit powder, sun dried, granules) preferably in an amount of 12 to 36 weight %; and yeast extract preferably in an amount of 0.5 to 3 weight %.

In another refinement, the tomato soup composition includes tomatoes, inulin, olives, onions, potatoes, and rice flour. In still another refinement, the tomato soup composition includes basil, whole leaf, dried preferably in an amount of 0.3 to 1 weight %; inulin preferably in an amount of 6 to 18 weight %; oil (olive) preferably in an amount of 4 to 14 weight %; onion, white, dried, (powder, minced) preferably in an amount of 8 to 24 weight %; parsley preferably in an amount of 0.3 to 0.9 weight %; potato preferably in an amount of 6 to 18 weight %; rice flour preferably in an amount of 9 to 27 weight %; salt (reg., kosher, sea salt) preferably in an amount of 4 to 14 weight %; tomatoes, (fruit powder, sun dried granules) preferably in an amount of 8 to 24 weight %; and yeast extract preferably in an amount of 0.7 to 2.2 weight %.

In a refinement, the quinoa-containing minestrone soup composition includes quinoa, green tea extract, optionally olive oil, optionally cabbage, optionally potatoes, optionally rice flour, and optionally tomatoes and optionally no tumeric. In a refinement, the quinoa-containing minestrone soup composition includes basil (whole leaf, dried preferably in an amount of 0.7 to 2 weight %; broccoli powder preferably in an amount of 0.6 to 2 weight %; cabbage white (flakes) preferably in an amount of 3 to 10 weight %; carrot (dehydrated, puffed, powder, pieces) preferably in an amount of 3 to 10 weight %; celery preferably in an amount of 1 to 4 weight %; celery seeds (powder) preferably in an amount of 0.07 to 0.2 weight %; garlic preferably in an amount of 0.7 to 2 weight %; green tea extract preferably in an amount of 0.02 to 0.06 weight %; inulin preferably in an amount of 1 to 5 weight %; leeks (granules −10+40), preferably in an amount of 0.7 to 2 weight %; oil (olive) preferably in an amount of 0.6 to 2 weight %; onion (powder, minced) preferably in an amount of 2 to 8 weight %; peas preferably in an amount of 3 to 10 weight %; potato preferably in an amount of 7 to 20 weight %; quinoa preferably in an amount of 7 to 20 weight %; rice flour preferably in an amount of 7 to 20 weight %; salt, preferably in an amount of 1 to 6 weight %; spinach (leaf, powder) preferably in an amount of 0.5 to 2 weight %; tomatoes (fruit powder, sun dried, granules) preferably in an amount of 2 to 6 weight %; yeast extract preferably in an amount of 0.6 to 2 weight %; zucchini (powder, diced) preferably in an amount of 2 to 8 weight %.

In another refinement, the quinoa-containing minestrone soup includes quinoa, cabbage, potatoes, and rice flour. In still another refinement, the quinoa-containing minestrone soup includes basil, whole leaf, dried preferably in an amount of 0.7 to 2.2 weight %; broccoli powder preferably in an amount of 0.7 to 2.2 weight %; cabbage white (flakes) preferably in an amount of 0.6 to 2.2 weight %; carrot (dehydrated, puffed, powder, pieces) preferably in an amount of 3 to 10 weight %; celeriac preferably in an amount of 2 to 6 weight %; celery seeds powder preferably in an amount of 0.6 to 1.8 weight %; garlic preferably in an amount of 1 to 3 weight %; Onion, white, dried, (powder, minced) preferably in an amount of 3 to 9 weight %; peas preferably in an amount of 3 to 10 weight %; potato preferably in an amount of 6 to 20 weight %; quinoa preferably in an amount of 8 to 23 weight %; rice flour preferably in an amount of 7 to 22 weight %; salt (reg., kosher, sea salt) preferably in an amount of 2 to 7 weight %; savoy cabbage preferably in an amount of 3 to 10 weight %; spinach (leaf, powder) preferably in an amount of 0.7 to 2.2 weight %; turmeric preferably in an amount of 0.6 to 1.8 weight %; yeast extract preferably in an amount of 3 to 10 weight %; and zucchini (powder,diced) preferably in an amount of 1 to 5 weight %.

In a refinement, the bean-containing minestrone soup composition includes white beans (e.g., great northern beans), great tea extract, optionally cabbage, and optionally potatoes. In a refinement, the bean-containing minestrone soup composition includes beans (great northern) preferably in an amount of 3 to 10 weight %; cabbage white (flakes) preferably in an amount of 2 to 8 weight %; carrot (dehydrated, puffed, powder, pieces) preferably in an amount of 2 to 8 weight %; celery preferably in an amount of 1 to 4 weight %; green tea extract preferably in an amount of 0.02 to 0.06 weight %; inulin preferably in an amount of 2 to 10 weight %; leeks (granules −10+40) preferably in an amount of 2 to 7 weight %; oil (olive) preferably in an amount of 2 to 7 weight %; onion (powder, minced) preferably in an amount of 2 to 7 weight %; parsley preferably in an amount of 0.2 to 1 weight %; peas preferably in an amount of 3 to 9 weight %; potato preferably in an amount of 15 to 45 weight %; rice flour preferably in an amount of 6 to 18 weight %; salt preferably in an amount of 2 to 8 weight %; spinach (leaf, powder) preferably in an amount of 0.5 to 1.5 weight %; tomatoes (fruit powder, sun dried, granules) preferably in an amount of 2 to 7 weight %; and yeast extract preferably in an amount of 0.5 to 1.5 weight %.

In a refinement, the bean-containing minestrone soup composition includes brown beans, carrots, peas, potato, and rice flour. In another refinement, the bean-containing minestrone soup composition includes carrot (dehydrated, puffed, powder, pieces) preferably in an amount of 4 to 14 weight %; celeriac preferably in an amount of 1 to 5 weight %; celery preferably in an amount of 0.5 to 1.6 weight %; leeks preferably in an amount of 2 to 8 weight %; oil (olive) preferably in an amount of 2 to 8 weight %; Onion, white, dried, (powder, minced) preferably in an amount of 3 to 10 weight %; parsley preferably in an amount of 0.5 to 1.5 weight %; peas preferably in an amount of 5 to 18 weight %; potato preferably in an amount of 8 to 24 weight %; rice flour preferably in an amount of 5 to 18 weight %; salt (reg., kosher, sea salt) preferably in an amount of 4 to 14 weight %; spinach (leaf, powder) preferably in an amount of 0.5 to 1.5 weight %; tomatoes, (fruit powder, sun dried granules) preferably in an amount of 0.9 to 2.8 weight %; turmeric preferably in an amount of 0.3 to 1.2 weight %; and yeast extract preferably in an amount of 0.5 to 1.5 weight %.

In a refinement, the pumpkin soup composition includes pumpkin, green tree extract, optionally rice flour, optionally carrots, and optionally brown rice powder. In a refinement, the pumpkin soup composition includes (new) includes brown rice powder (whole grain) preferably in an amount of 3 to 9 weight %; carrot (dehydrated, puffed, powder, pieces) preferably in an amount of 2 to 8 weight %; green tea extract preferably in an amount of 0.02 to 0.06 weight %; inulin preferably in an amount of 2 to 10 weight %; oil (olive) preferably in an amount of 1 to 7 weight %; onion (powder, minced) preferably in an amount of 1.0 to 3 weight %; pumpkin powder preferably in an amount of 20 to 60 weight %; rice flour preferably in an amount of 15 to 45 weight %; salt preferably in an amount of 2 to 10 weight %; and yeast extract preferably in an amount of 0.3 to 1 weight %.

In a refinement, the first vegetable broth includes carrots, maltodextrin, celery, spinach, and tomatoes. In a refinement, the first vegetable broth includes carrot (dehydrated, puffed, powder, pieces) preferably in an amount of 6 to 18 weight %; celery preferably in an amount of 3 to 10 weight %; garlic preferably in an amount of 3 to 10 weight %; maltodextrin preferably in an amount of 8 to 25 weight %; oil (canola) preferably in an amount of 0.5 to 2 weight %; onion (powder, minced) preferably in an amount of 6 to 18 weight %; parsley preferably in an amount of 3 to 10 weight %; potato preferably in an amount of 1 to 3 weight %; salt preferably in an amount of 7 to 21 weight %; spinach (leaf, powder) preferably in an amount of 3 to 10 weight %; tomatoes (fruit powder, sun dried, granules) preferably in an amount of 6 to 18 weight %; and yeast extract preferably in an amount of 1 to 6 weight %.

In a refinement, the second vegetable broth (chicken flavoring) includes carrots, chicken flavoring, maltodextrin, celery, spinach, soy lecithin, and tomatoes. In a refinement, the second vegetable broth composition includes carrot (dehydrated, puffed, powder, pieces) preferably in an amount of 3 to 10 weight %; celery preferably in an amount of 3 to 12 weight %; garlic preferably in an amount of 3 to 9 weight %; maltodextrin preferably in an amount of 8 to 25 weight %; oil (canola) preferably in an amount of 0.5 to 2 weight %; onion preferably in an amount of powder, minced) preferably in an amount of 3 to 12 weight %; parsley preferably in an amount of 3 to 10 weight %; potato preferably in an amount of 1 to 6 weight %; salt preferably in an amount of 8 to 25 weight %; soy lecithin preferably in an amount of 0.5 to 3 weight %; spinach (leaf, powder) preferably in an amount of 3 to 12 weight %; tomatoes (fruit powder, sun dried, granules) preferably in an amount of 6 to 18 weight %; xanthan gum preferably in an amount of 0.5 to 4 weight %; and yeast extract preferably in an amount of 4 to 12 weight %.

In a refinement, the energy drink composition includes glycerin preferably in an amount of 20 to 60 weight %; water (purified) preferably in an amount of 40 to 80 weight %.

In a refinement, the tea composition that includes spearmint includes spearmint leaves organic preferably in an amount of 70 to 100 weight %.

In a refinement, the tea composition that includes lemon and spearmint includes lemon myrtle organic preferably in an amount of 3 to 12 weight %; lemon peel organic preferably in an amount of 10 to 25 weight %; spearmint leaves organic preferably in an amount of 50 to 95 weight %.

In a refinement, the tea composition that includes hibiscus includes hibiscus tea leaves organic preferably in an amount of 80 to 100 weight %.

In a refinement, the algal oil composition includes schizocatrium algae oil (DHA Omega-3) preferably in an amount of 80 to 100 weight %.

In a refinement, the nutrient replenishment composition (NR-1) includes beet root powder, calcium carbonate, carrots, collard leaf, kale leaf, and tomatoes. In a refinement, the nutrient replenishment composition (NR-1) includes ascorbic acid preferably in an amount of 1 to 3 weight %; beet root powder preferably in an amount of 6 to 20 weight %; beta carotene preferably in an amount of 0.05 to 0.15 weight %; calcium carbonate preferably in an amount of 6 to 20 weight %; carrot (dehydrated, puffed, powder, pieces) preferably in an amount of 6 to 20 weight %; cholecaliciferol preferably in an amount of 0.00 weight %; chromuim Picolinate preferably in an amount of 0.00 weight %; collard leaf powder preferably in an amount of 6 to 20 weight %; cupric sulfate preferably in an amount of 0.01 to 0.06 weight %; cyanocobalamin, 0.00; D1-alpha tocopherol acetate preferably in an amount of 0.3 to 1 weight %; ferrous fumarate preferably in an amount of 0.2 to 1 weight %; folic acid preferably in an amount of 0.00 weight %; kale leaf preferably in an amount of 6 to 20 weight %; magnesium stearate preferably in an amount of 1 to 6 weight %; manganese sulfate preferably in an amount of 0.04 to 0.08 weight %; niacinamide preferably in an amount of 0.3 to 1 weight %; pantothenic acid preferably in an amount of 0.1 to 0.6 weight %; phytonadione preferably in an amount of 0.00 weight %; potassium iodine preferably in an amount of 0 weight %; pyriodoxine HCl preferably in an amount of 0.03 to 0.1 weight %; riboflavin preferably in an amount of 0.02 to 0.1 weight %; sodium molybdate preferably in an amount of 0.00 weight %; sodium selenate preferably in an amount of 0.00 weight %; spinach (leaf, powder) preferably in an amount of 6 to 20 weight %; thiamine mononitrate preferably in an amount of 0.02 to 0.1 weight %; tomatoes (fruit powder, sun dried, granules) preferably in an amount of 6 to 20 weight %; tribasic calcium phosphate preferably in an amount of 0.5 to 2 weight %; and zinc oxide preferably in an amount of 0.2 to 0.8 weight %.

In a variation, the each of the components of the fasting mimicking diet package and therefore the fasting mimicking diet, is substantially gluten free (e.g., each component has less than 20 ppm gluten) or very low gluten (e.g., each component has 20-100 ppm). In other variations, each of the components are provided in a serving size from 20 to 60 g. In other variations, the nut-containing nutrition bar is provided in a serving size from 30 to 60 g; cocoa-containing nutrition bar is provided in a serving size from 15 to 40 g; the olive containing composition (sea salt version) in a serving size from 10 to 20 g; the olive containing composition (garlic version) in a serving size from 10 to 20 g; kale cracker composition is provides in a serving size from 30 to 60 g; In another variation, the kale cracker compositions are provided in a serving size from 20 to 50 g; the vegetable soup compositions are provided in a serving size from 20 to 50 g; the mushroom soup compositions are provided in a serving size from 20 to 50 g; the tomato soup compositions are provided in a serving size from 20 to 50 g; the bean-containing minestrone soup compositions are provided in a serving size from 20 to 50 g; the quinoa-containing minestrone soup compositions are provided in a serving size from 20 to 50 g; the pumpkin soup compositions are provided in a serving size from 20 to 50; the first vegetable both compositions are provided in a serving size from 5 to 15; the second vegetable both compositions are provided in a serving size from 3 to 15; and Energy Drink composition is provided in serving size of 1 to 5 oz.

It should be appreciated that the present invention provides a method, dietary composition and combination of drugs listed as set forth above to promote cellular reprogramming to generate multi-potent cells and promote regeneration in multiple systems and/or organs including the nervous system, hematopoietic system, liver, muscle, digestive system, heart, lungs, kidneys, and bones for the purpose of rejuvenating these systems and reversing the diseases that affect them.

The following examples illustrate the various embodiments of the present invention. Those skilled in the art will recognize many variations that are within the spirit of the present invention and scope of the claims.

Cycles of a Fasting Mimicking Diet (FMD) Rescue Mice from Late Stage T2D

As a consequence of insulin resistance, the decrease in the number of functional insulin-producing β-cells contributes to the pathophysiology of T2D by eventually leading to insulin deficiency (Cnop et al., 2005; Dor and Glaser, 2013). Previously, we showed that a 4-day fasting mimicking diet (FMD) could induce metabolic changes similar to those caused by prolonged fasting and reduce insulin and glucose levels while increasing ketone bodies and igfbp1 (Brandhorst et al., 2015) (FIG. 9). Although the role of periodic fasting and fasting mimicking diets on insulin function is unknown, the effects of intermittent fasting and chronic calorie restrictions (CR) on insulin sensitivity have been previously reported (Barnosky et al., 2014). Here our focus is on the putative effects of the FMD in promoting β-cells regeneration, although we have also investigated the effects of the FMD on insulin resistance.

Figure 1A:
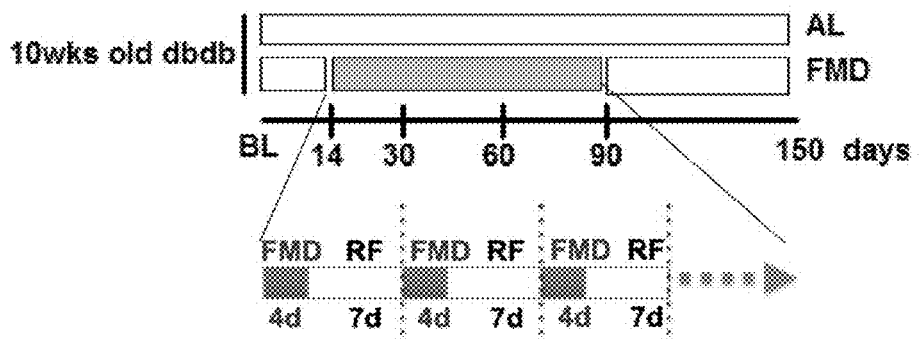
Figure 1B:
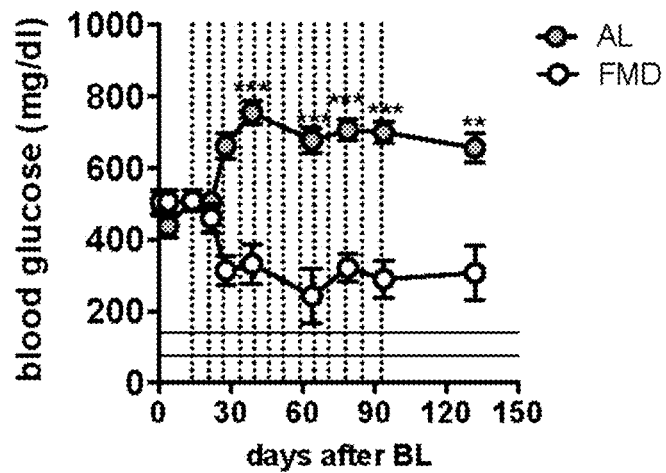
Figure 1C:
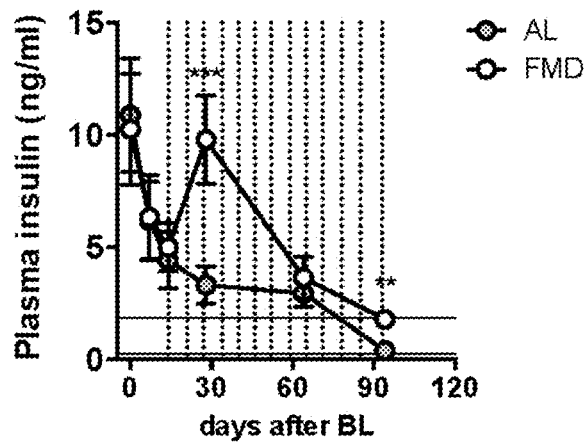
Figure 1D:
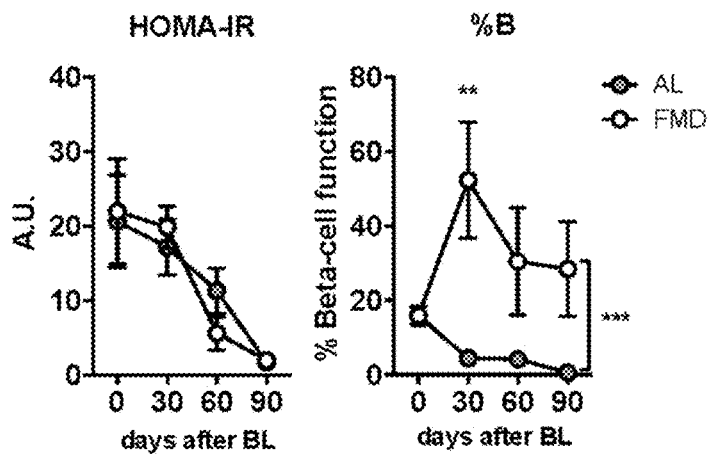
Figure 1E:
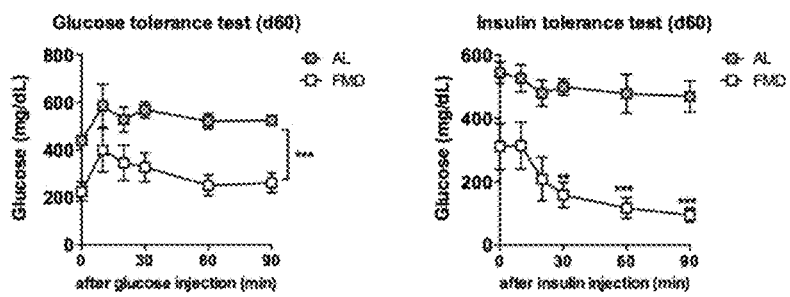
Figure 1F:
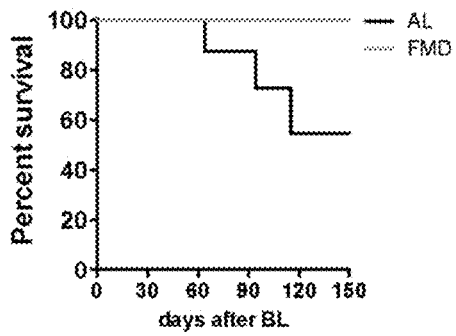
Figure 10A:
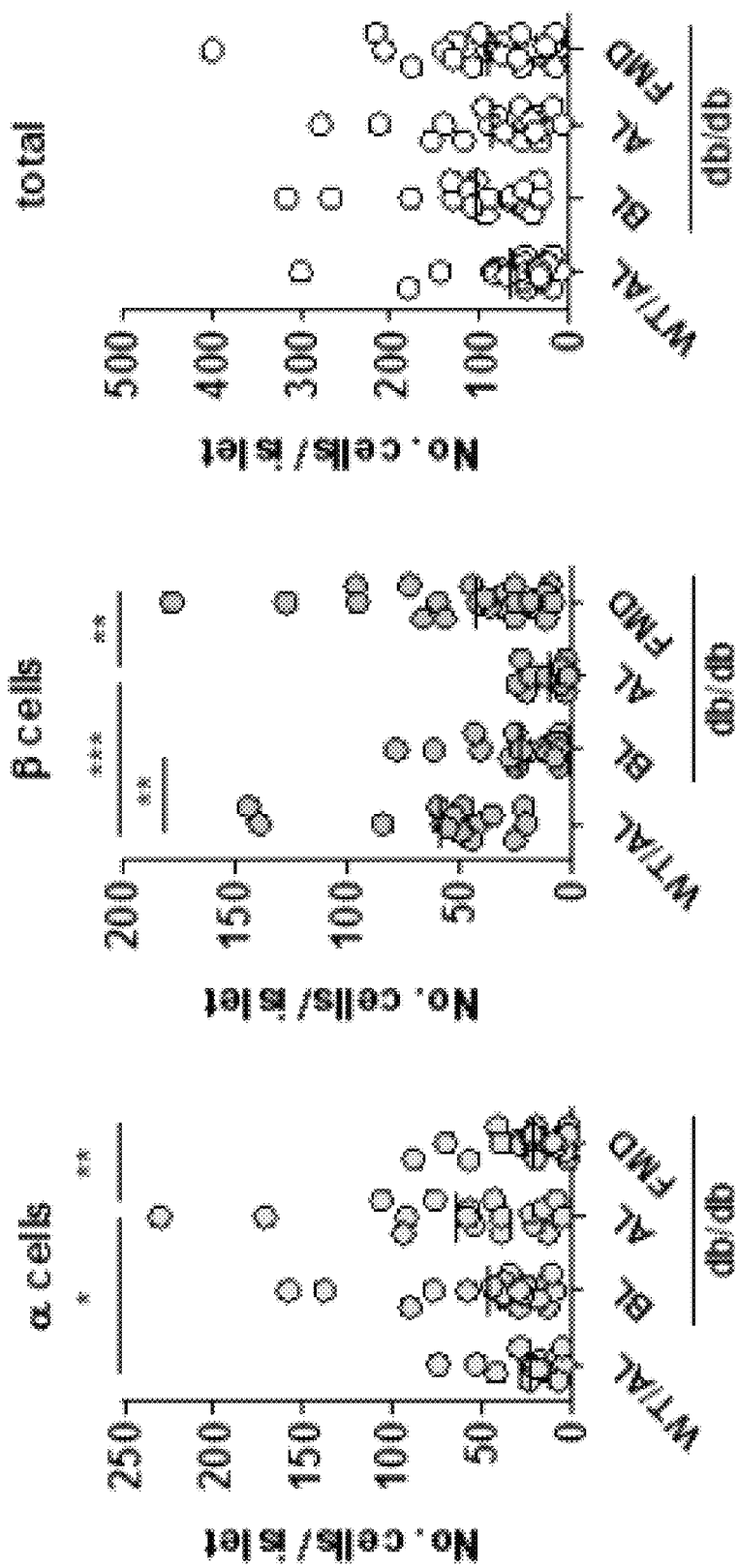
Figure 10B:
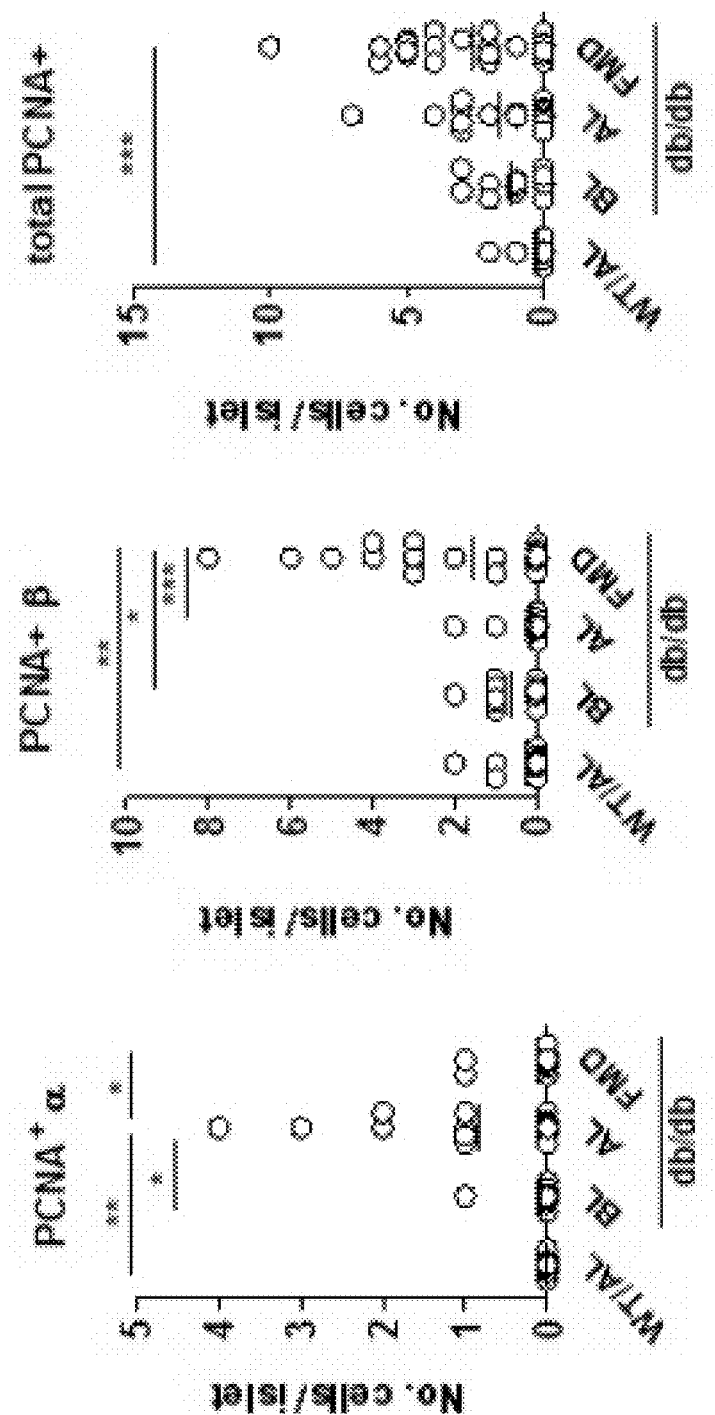
Figure 10C:
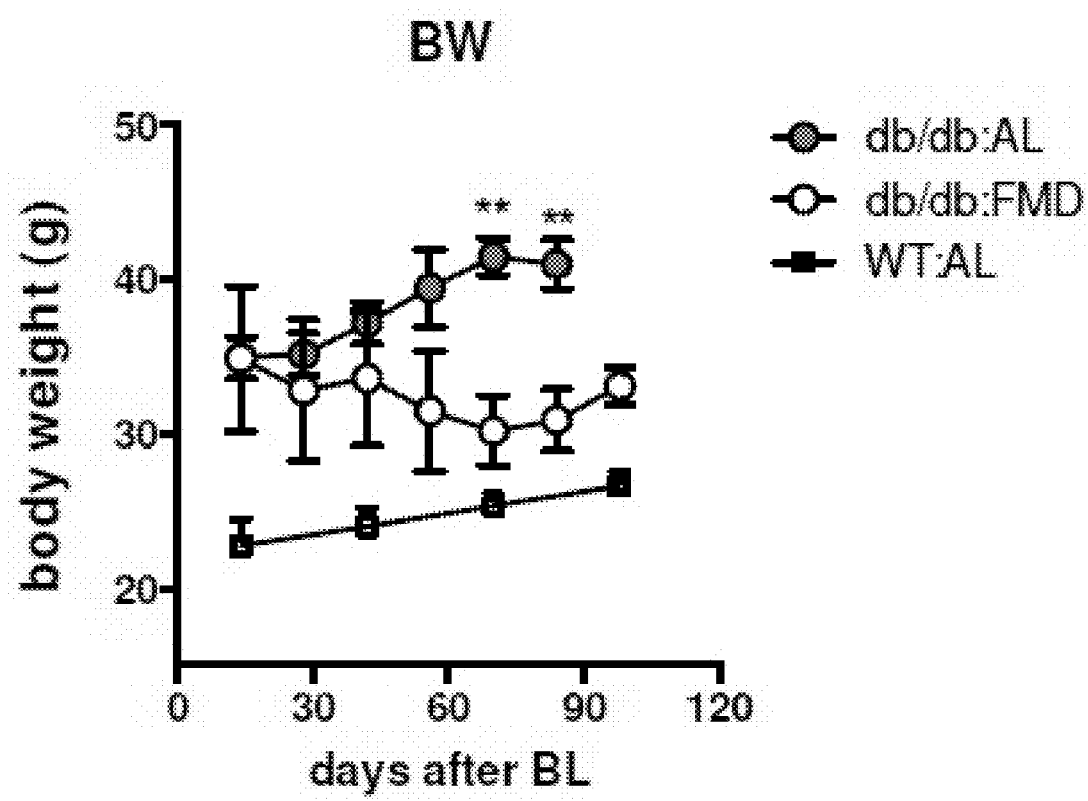
Figure 10D:
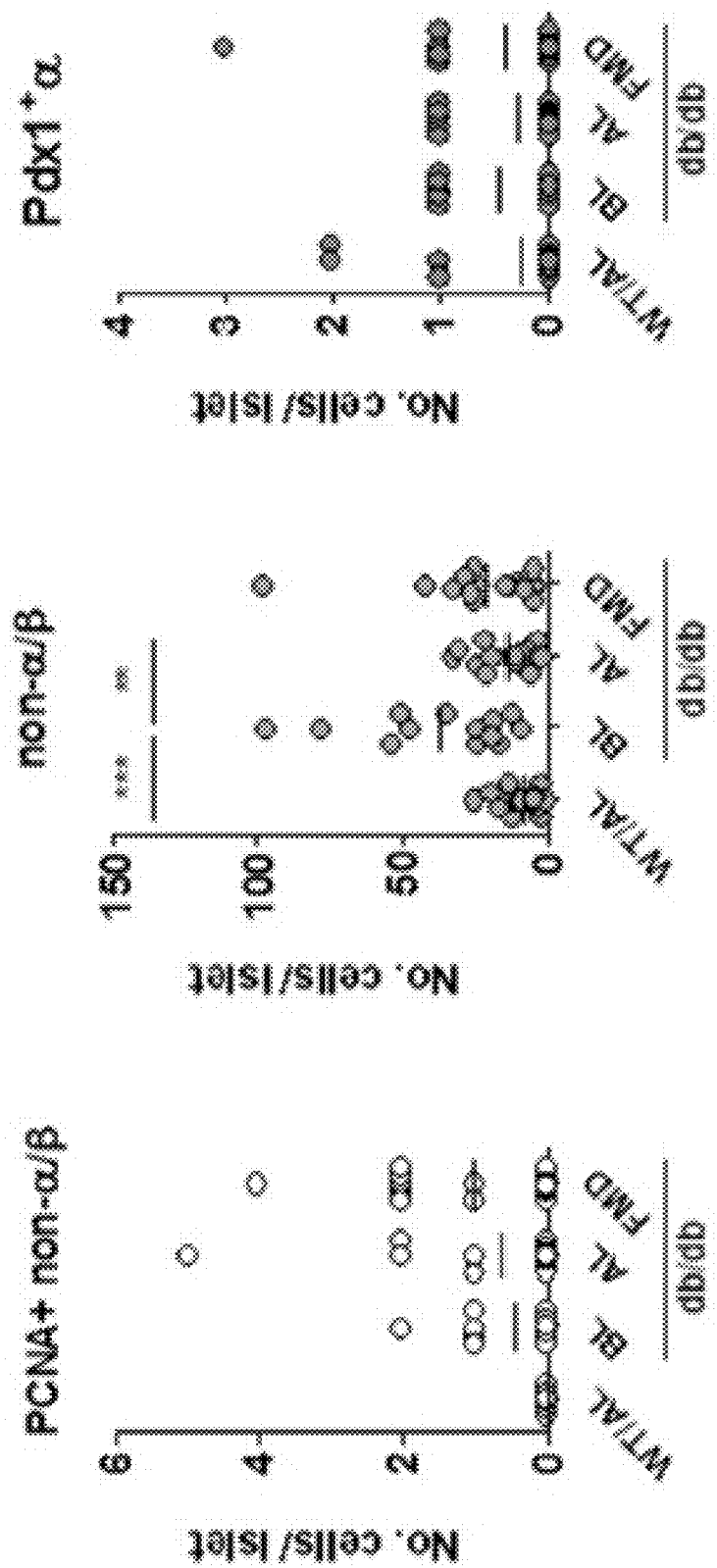
Figure 10E:
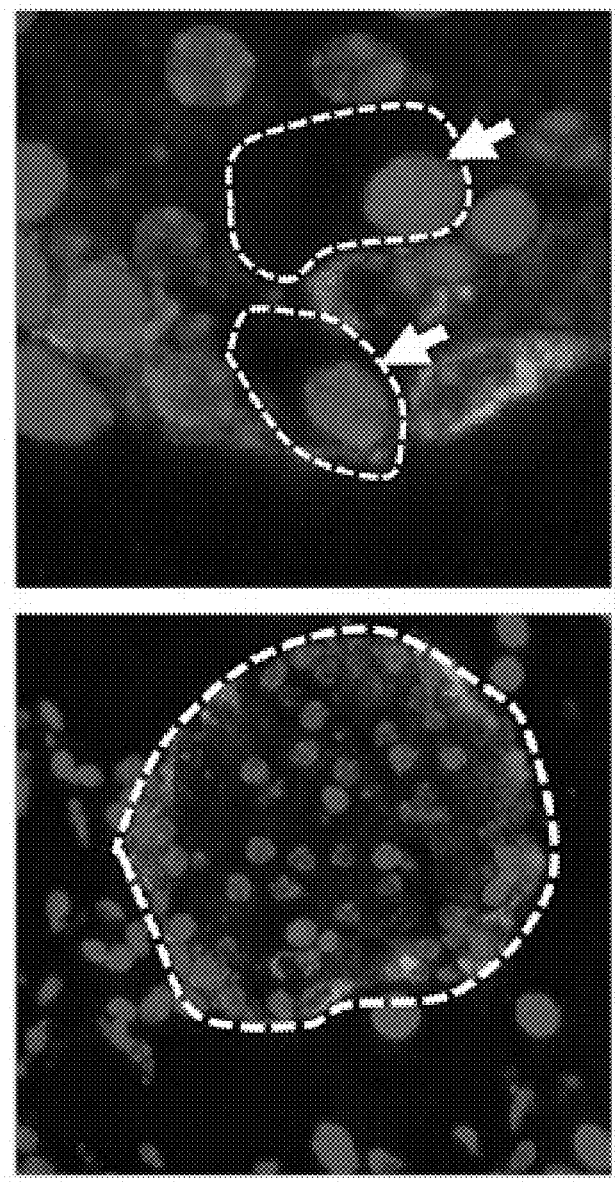
Figure 10F:
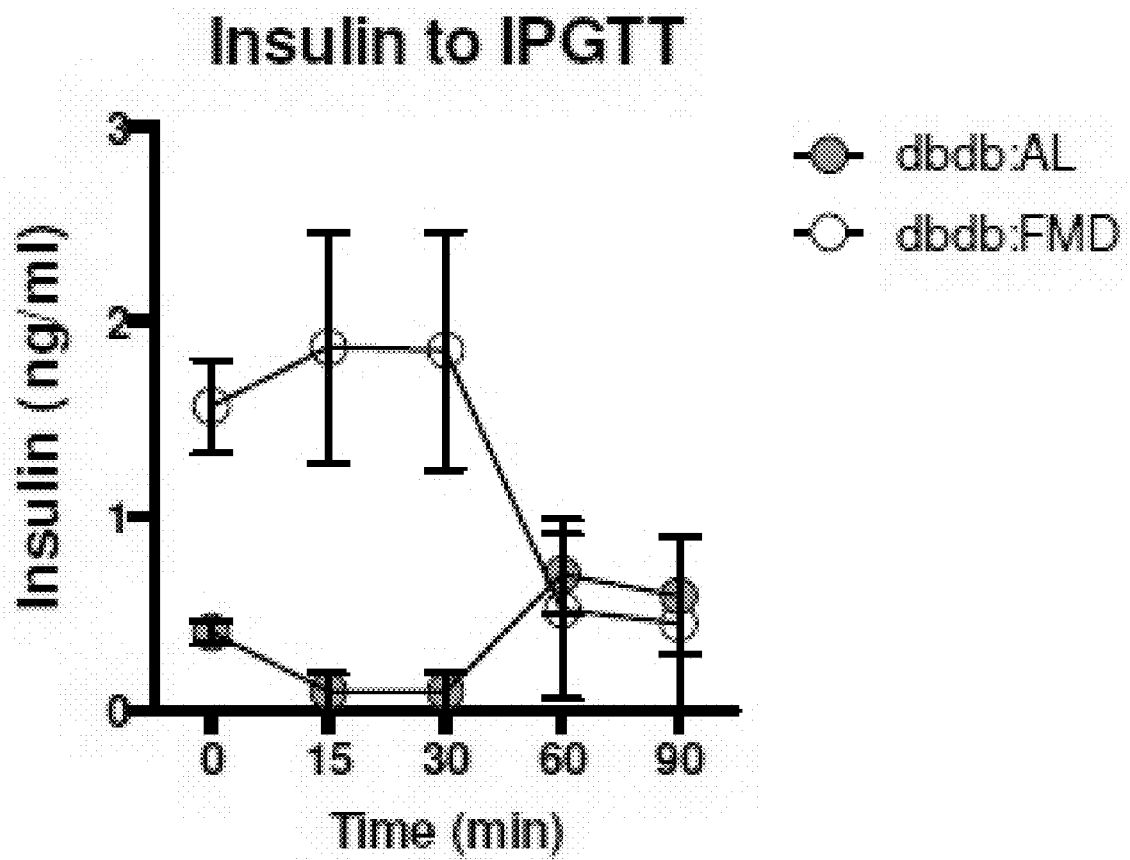
Figure 10G:
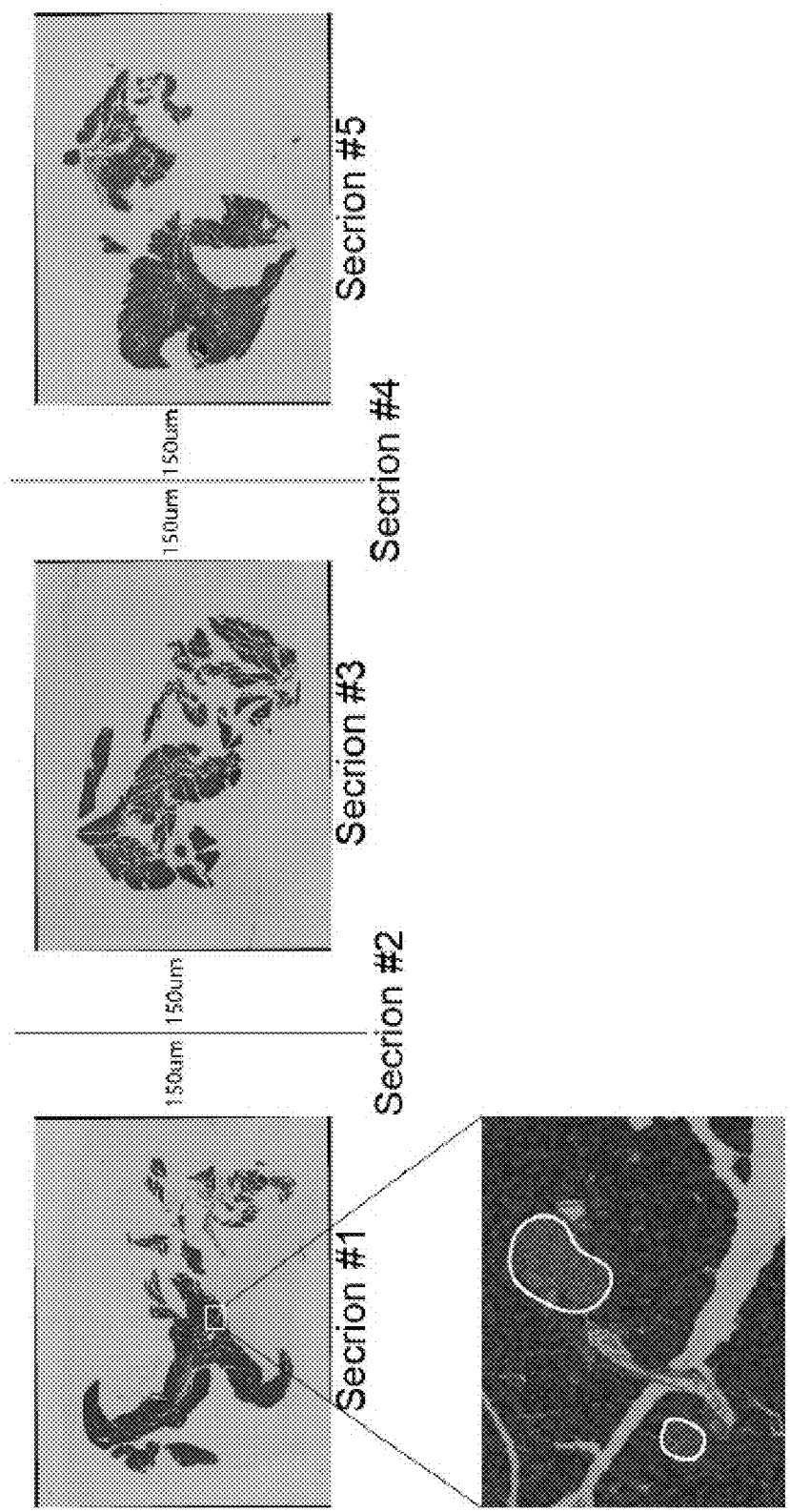
Figure 11A:
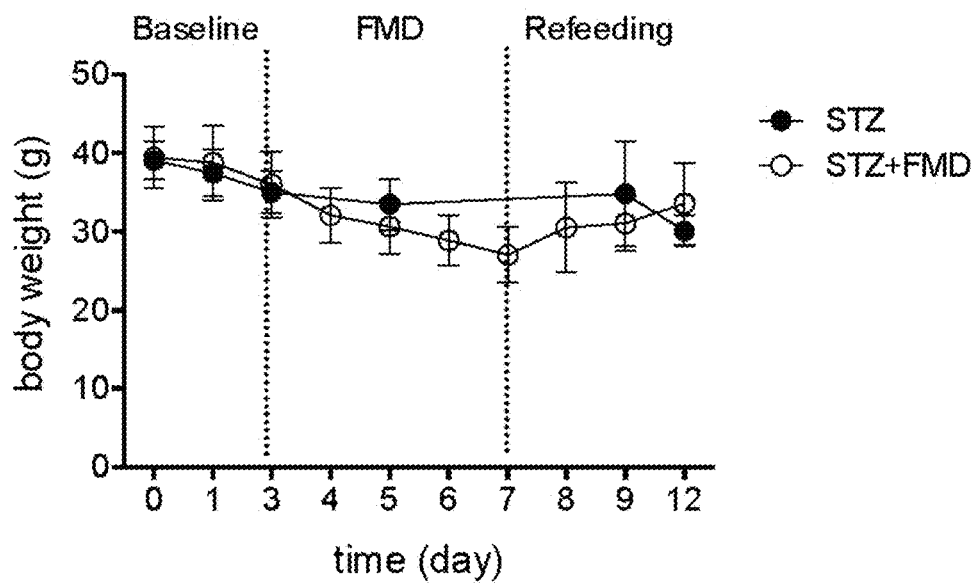
Figure 11B:
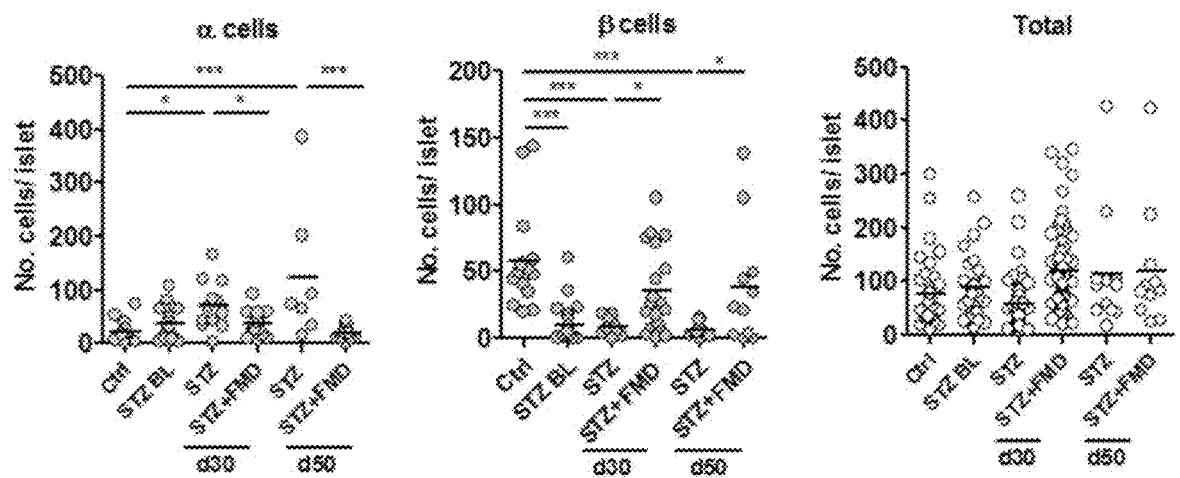
Figure 11C:
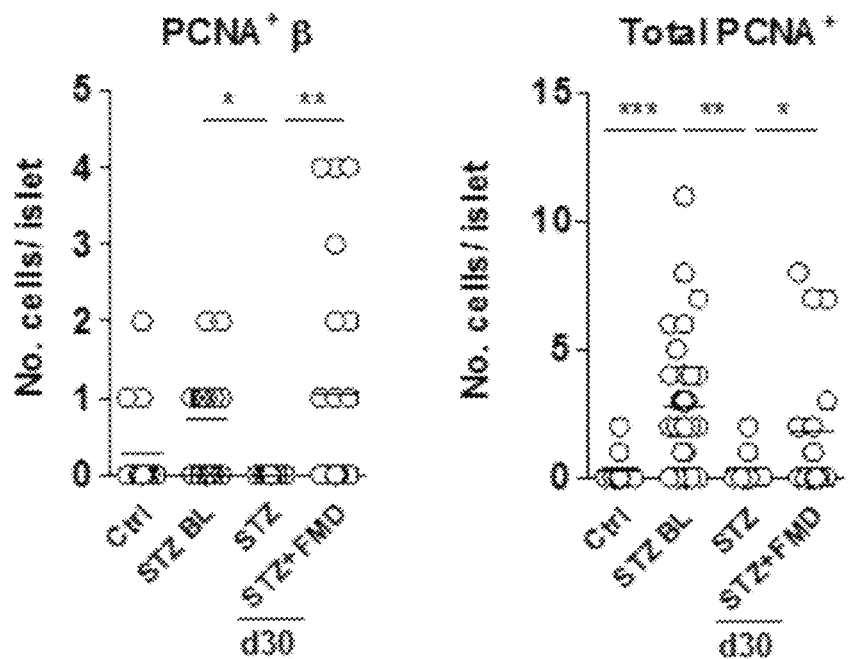
Figure 11D:
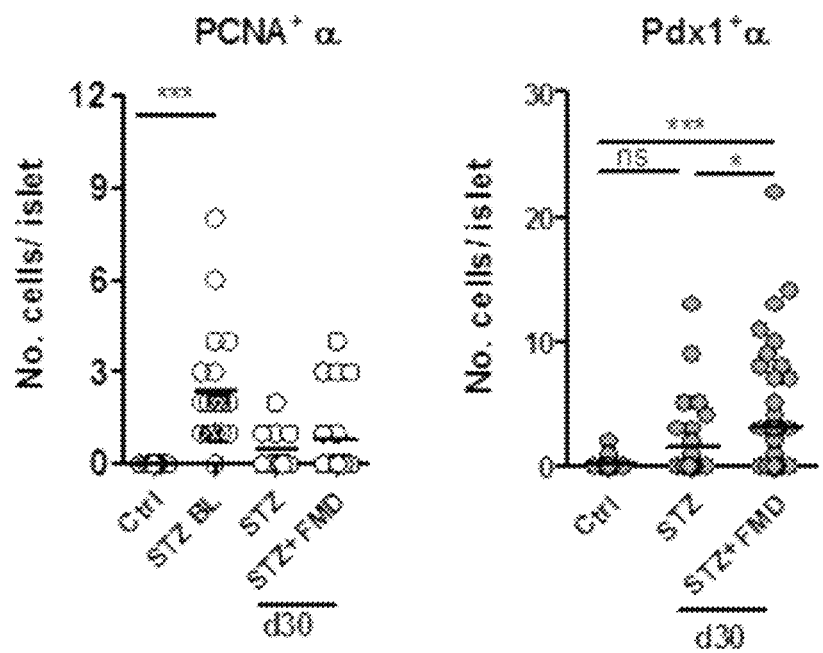
Figure 11E:
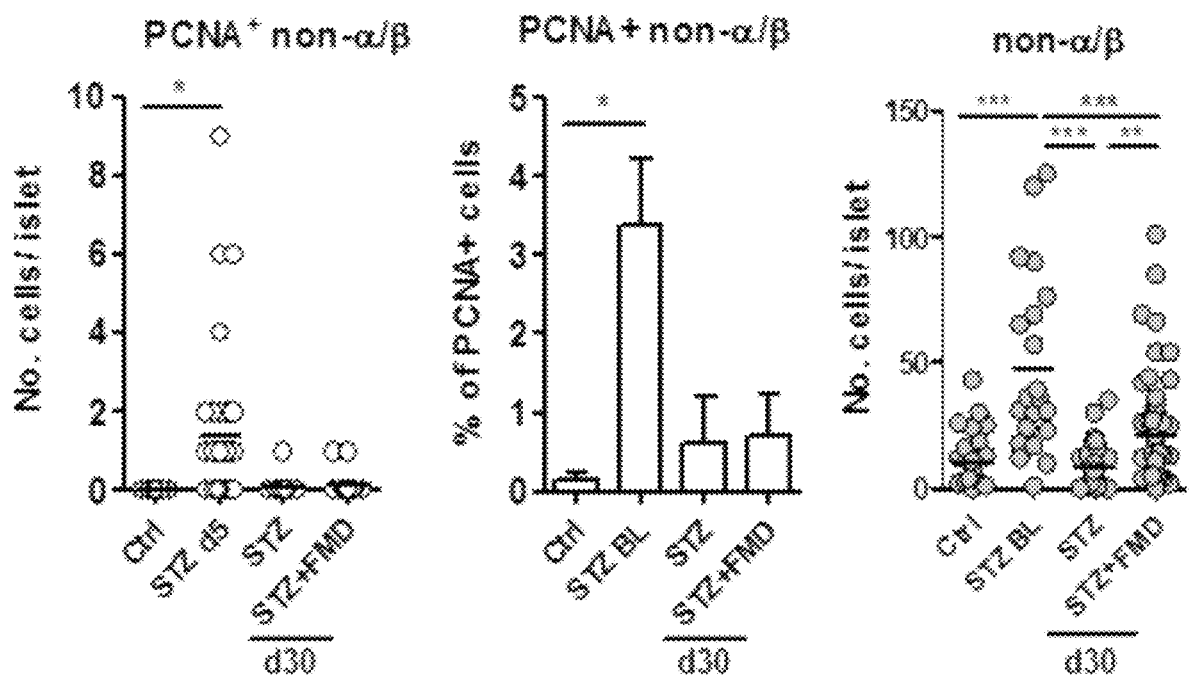
Figure 11F:
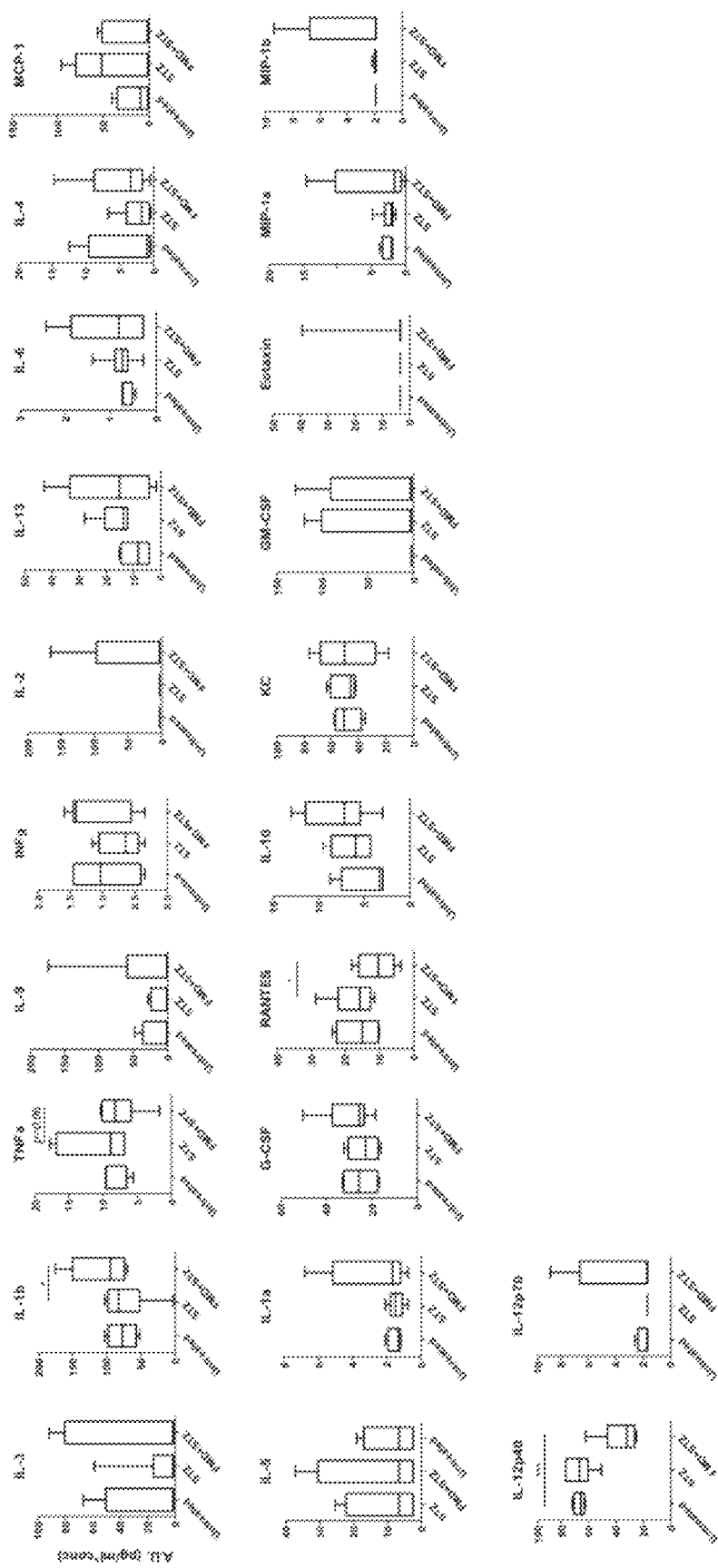
Figure 12A:
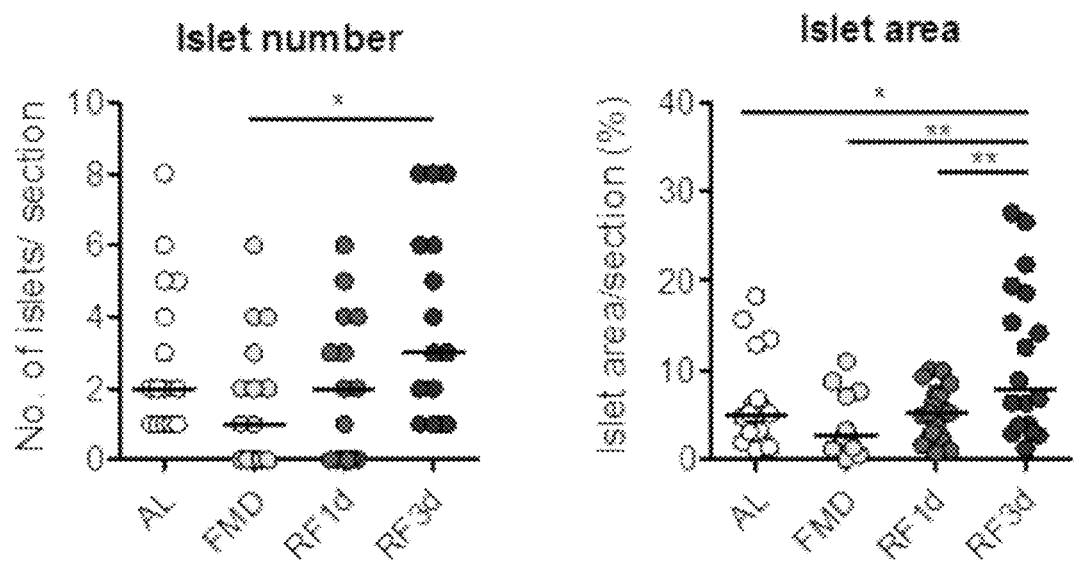
Figure 12B:
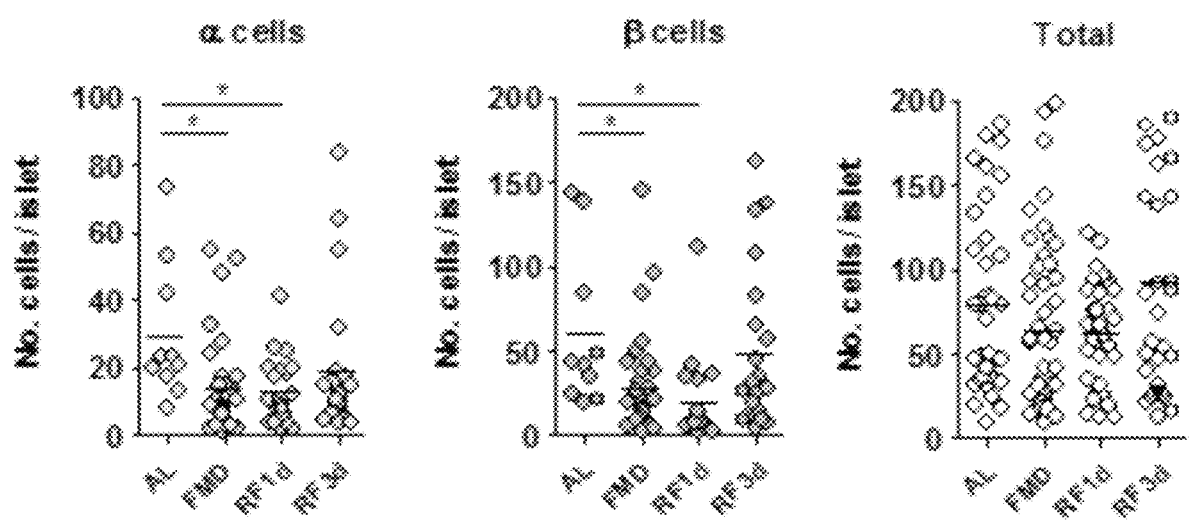
Figure 12C:
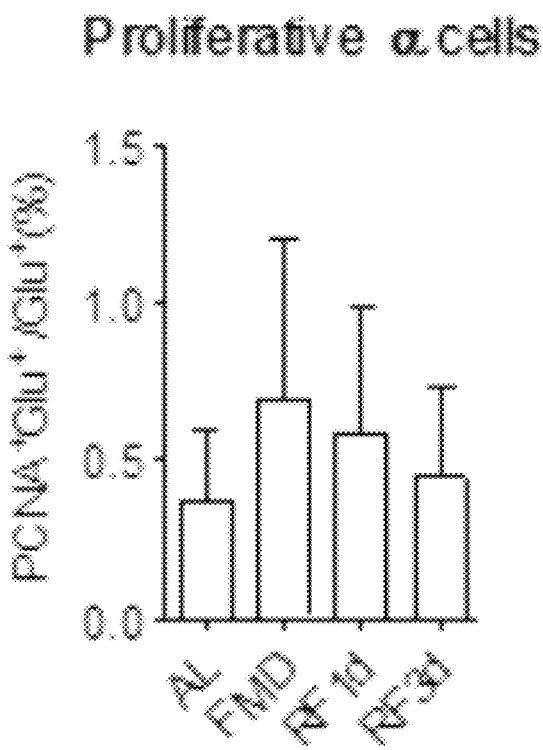
Figure 12D:
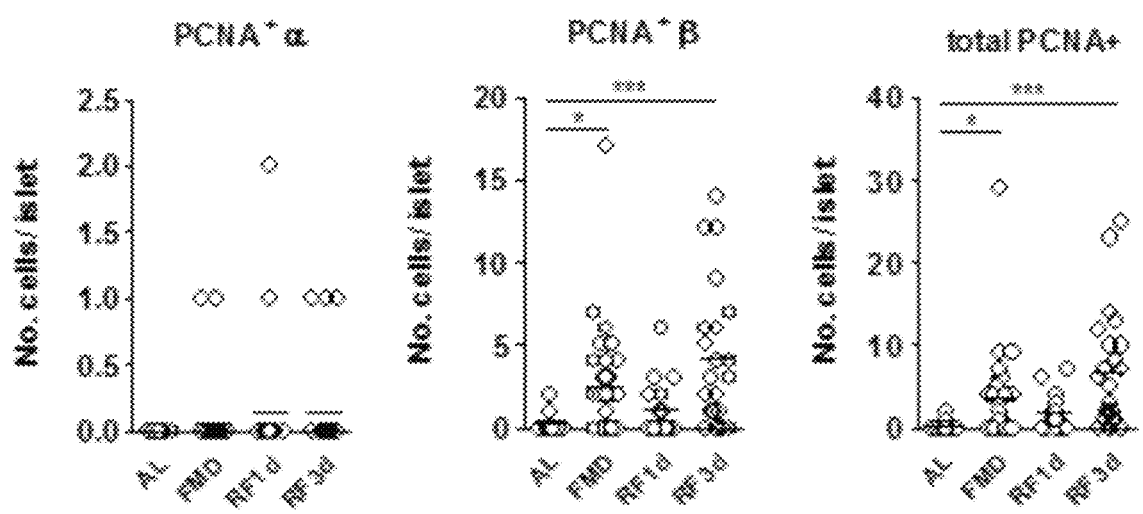
Figure 12E:
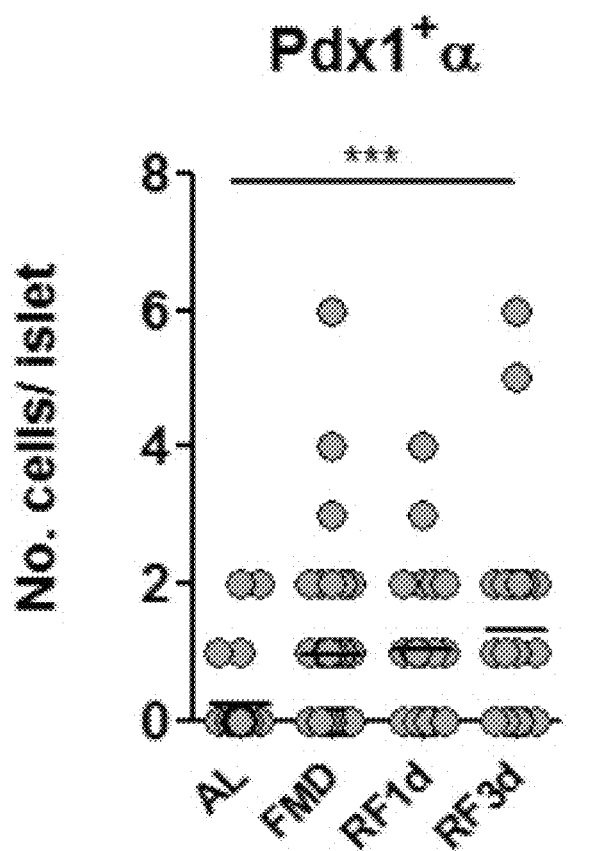
Figure 12F:
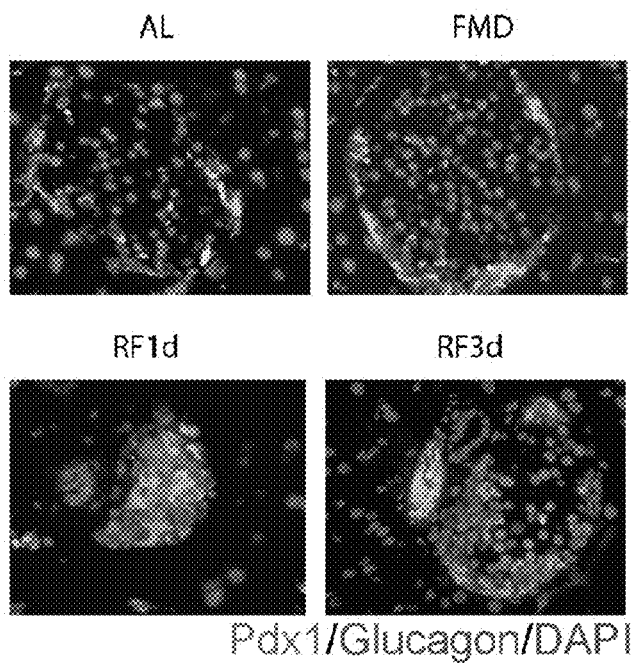
Figure 12G:
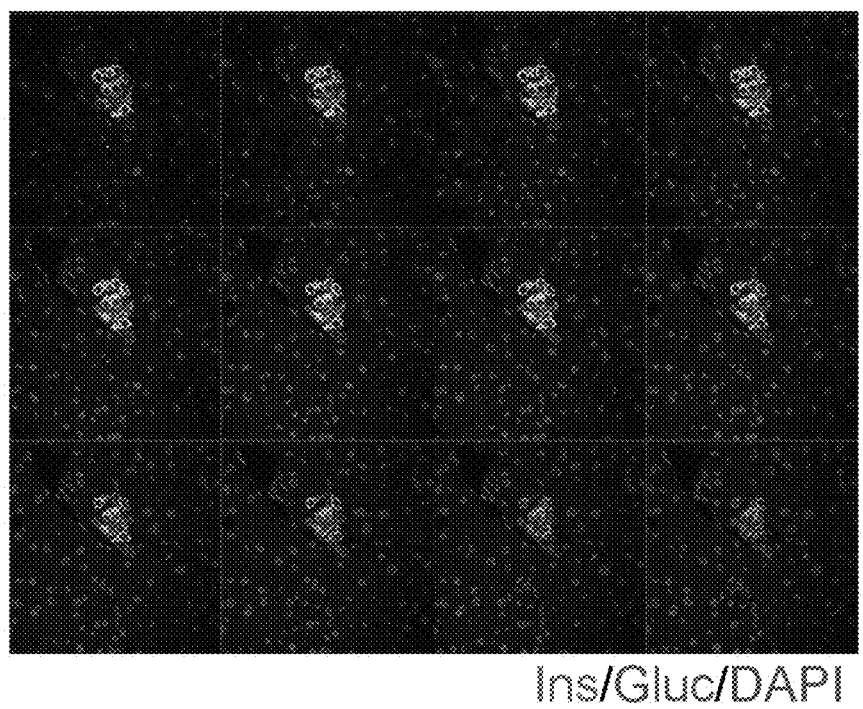
Figure 12H:
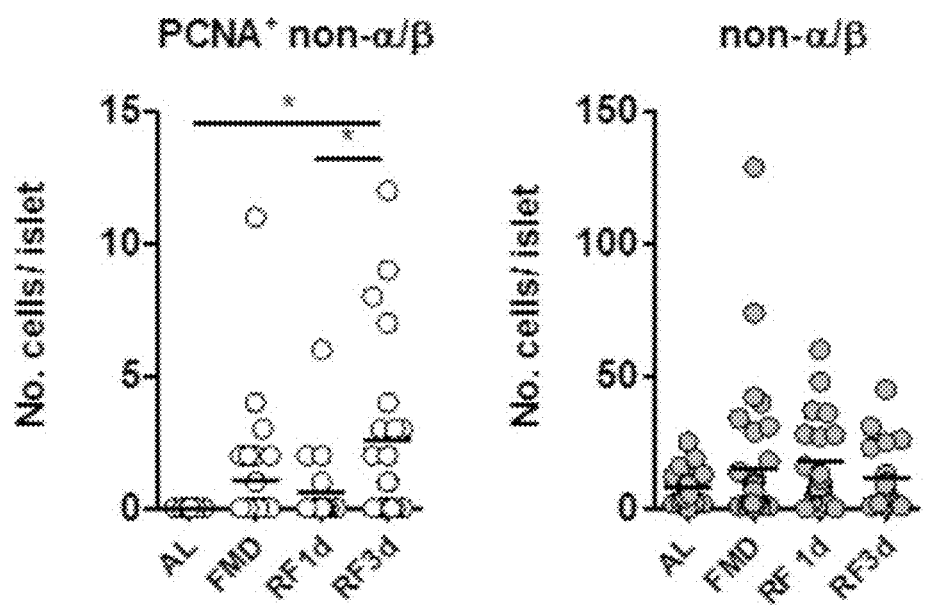

Given that β-cells replicate at an extremely low rate in the adult pancreas (Meier et al., 2008; Teta et al., 2005) and that β-cell neogenesis occurs rarely (Xiao et al., 2013), depletion of β cells and the consequent loss of insulin secretion during late stage diabetes have often been considered conditions whose reversals require islet and stem cells transplantation (Fiorina et al., 2008; Kroon et al., 2008; Milanesi et al., 2012; Pipeleers et al., 2002; Villani et al., 2014). To determine whether the FMD could affect the β-cell deficiency associated with T2D, we studied its effect on mice with a point mutation in the leptin receptor gene ($Lepr^{db/db}$), which causes insulin resistance and late stage loss of insulin secretion. As reported by others, db/db mice developed hyperglycemia at 10 weeks of age, which we refer to as baseline (BL) (FIG. 1A). This was accompanied by high insulin levels initially compensating for insulin resistance followed by the development of severe hyperglycemia at 12 weeks of age caused by the decline in insulin secretion (FIG. 1B to 1C)(Arakawa et al., 2001). As a result, db/db mice began to die at around 4 months of age. We attempted to reverse these late-stage T2D phenotypes by treating 12-week-old mice (14 days after the hyperglycemia stabilized, baseline) with weekly cycles of the 4-day FMD (FIG. 1A). FMD cycles caused a major reduction and return to nearly normal levels of blood glucose in db/db mice by d60, (FIG. 1B). The FMD cycles also reversed the decline in insulin secretion at d30 and improved plasma insulin levels at day 90 (FIG. 1C). A Homeostasis Model Assessment (HOMA) was performed to estimate steady state β-cell function (% B) and insulin sensitivity (% S), as previously described (Hsu et al., 2013; Matthews et al., 1985). The results indicate that the reversal of hyperglycemia was mainly caused by an induction of steady state β-cell function (% B) in addition to the minor alleviation of insulin resistance (HOMA-IR) (FIG. 1D). Nevertheless, mice receiving the FMD showed improved glucose tolerance and insulin tolerance compared to the ad libitum (AL) fed controls (FIG. 1E), due in part to the enhanced insulin secretion functions (FIG. 10F). Notably, although db/db mice on the FMD diet gained less weight compared to those on the regular diet, they maintained a weight that was approximately 22% higher than that of their healthy wild-type (WT) littermates during the entire experiment (FIG. 10C). Altogether, these results indicate that FMD cycles rescued mice from late stage T2D by restoring insulin secretion and reducing insulin resistance, leading to a major improvement in survival (FIG. 1F, *$p<0.05$, Log-rank test for trend).

Cycles of FMD Reverse β-Cell Failure in T2D

Figure 1G:
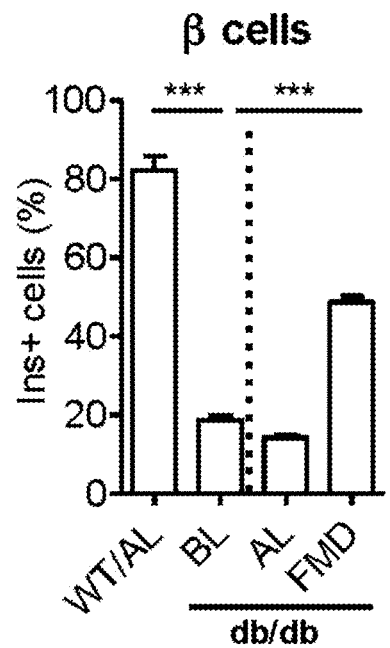
Figure 1H:
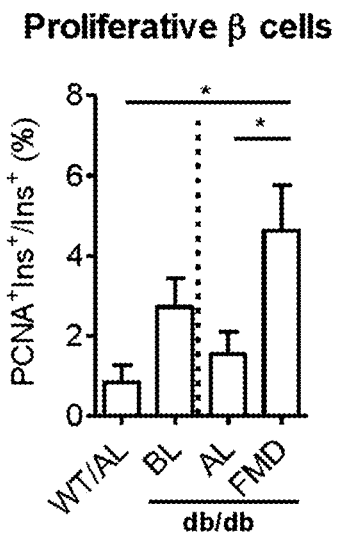
Figure 1I:
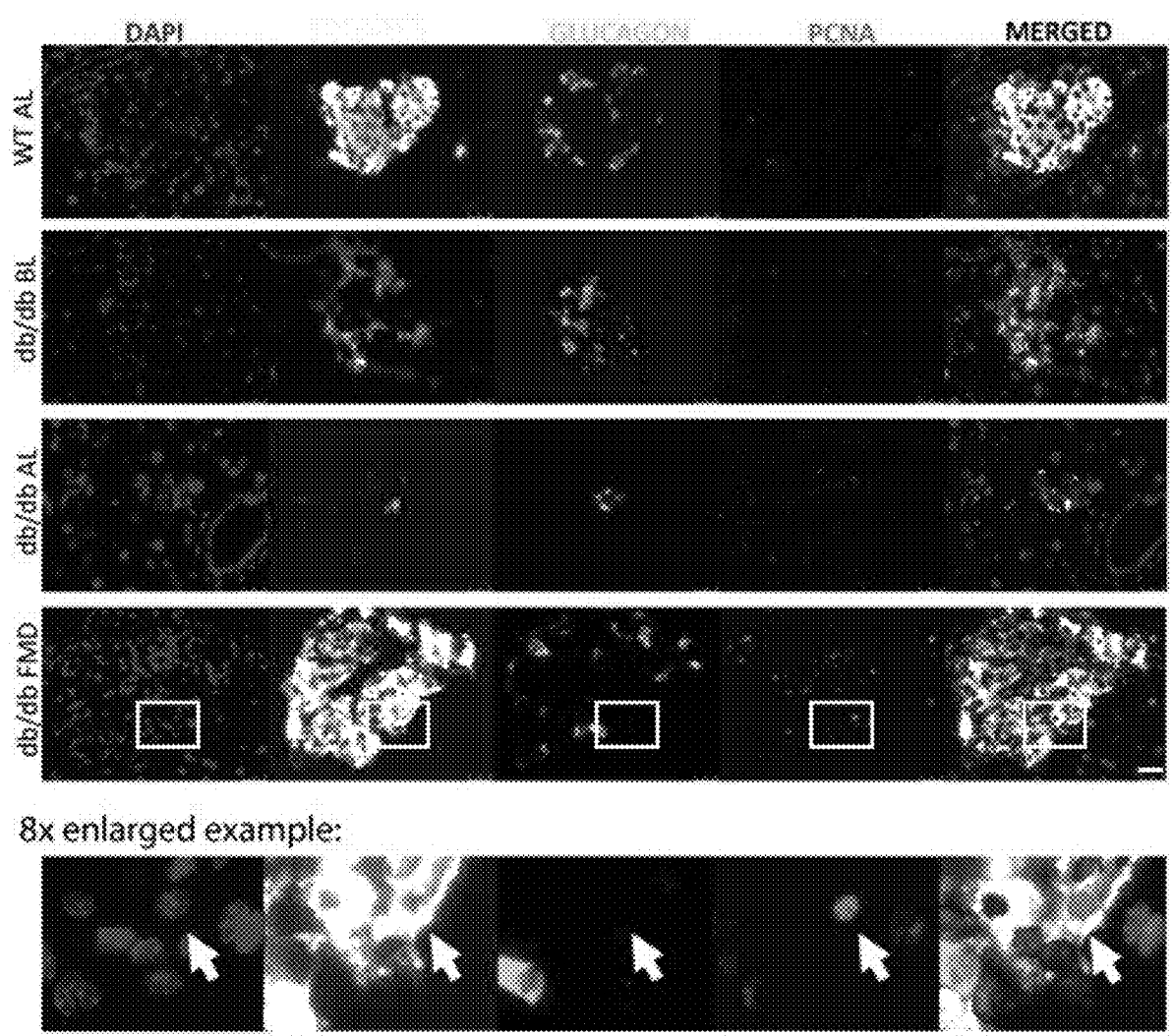

Dedifferentiation of β cells, which results in increased non-hormone producing cells within pancreatic islets, is a feature of diabetic β-cell failure (Dor and Glaser, 2013; Kim-Muller et al., 2014; Talchai et al., 2012). Similar to what was previously reported by others, we found an increase in cells producing neither insulin nor glucagon (i.e. non-α/β) and a decrease in β-cell number in pancreatic islets of late stage T2D mice but not in those of WT/AL healthy controls (FIGS. 1G and 10, db/db BL compared to WT/AL). We also found that β-cell proliferation was low in the late stage of the disease (FIG. 1H, AL day 60 compared to BL). Whereas db/db mice fed ad libitum (db/db:AL) showed a 60-80% reduction in β-cell count at day 60, db/db mice receiving FMD cycles (db/db:FMD) displayed a major improvement in the number and proliferation of insulin-generating β cells (comparing db/db BL, FIG. 1G-I), but not in the number of non-α/β cells (FIG. 10, day 60). Pancreatic islets collected from db/db mice treated with FMD cycles (day 60) displayed increased glucose stimulated insulin secretion (GSIS), compared to that of islets from db/db:AL mice (FIG. 1J). We also determined that a longer exposure time (time point 120) was necessary to distinguish between the functionality of islets from db/db:AL and db/db:FMD group mice (FIG. 1J). Overall, these results suggest that, in addition to improving insulin sensitivity, FMD induced β-cell regeneration to reverse β-cell loss, which may alleviate late stage T2D symptoms and mortality.

FMD Cycles Restore Insulin-Dependent Glucose Homeostasis in STZ-Induced T1D

Figure 2A:
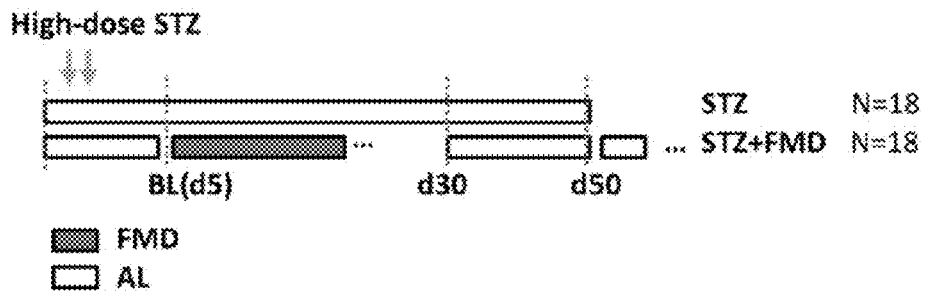
Figure 2B:
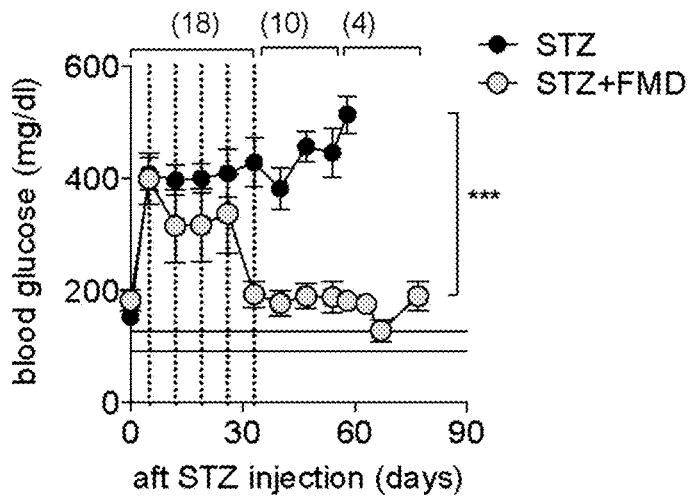
Figure 2C:
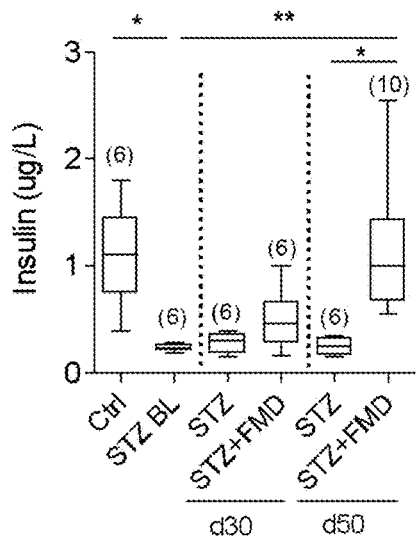
Figure 2D:
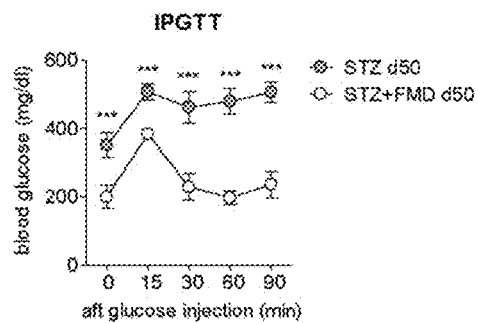
Figure 2E:
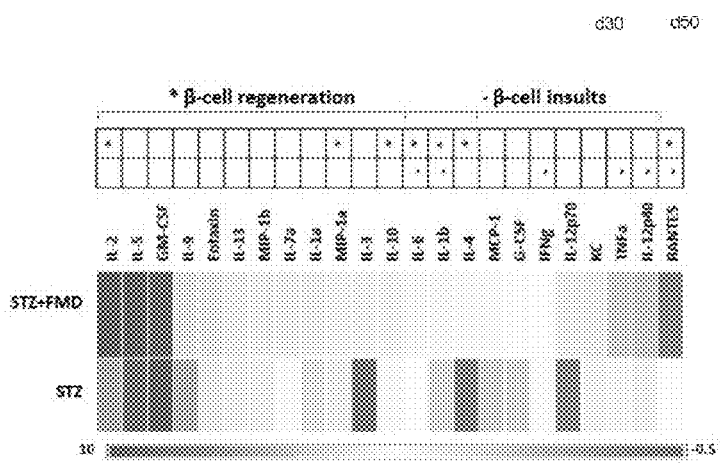

To examine further the role of FMD cycles in stimulating β-cell regeneration, we applied FMD cycles on a T1D model, in which high-dose streptozotocin (STZ) treatment causes the depletion of insulin-secreting β cells (Wu and Huan, 2008; Yin et al., 2006). Starting 5 days after STZ treatment, which we refer to as baseline (STZ BL), hyperglycemia (>300 mg/dl) was observed in both mice fed AL and those subjected to multiple cycles of the 4-day FMD every 7 days (4 days of FMD followed by 3 days of re-feeding, every 7 days per cycle) (FIGS. 2A and 2B). Levels of blood glucose continued to increase in STZ-treated mice receiving the AL diet, and reached levels above 450 mg/dl at both days 30 and 50. On the other hand, in mice receiving FMD cycles, hyperglycemia and insulin deficiency were both significantly alleviated on day 30. (FIG. 2B, sample size indicated in parentheses). More remarkably, the levels of these physiological parameters returned to nearly normal range by day 50-60 after cycles of FMD (FIGS. 2B and 2C, sample size indicated in parentheses). Intraperitoneal glucose tolerance tests (IPGTTs) at day 50 confirmed that STZ-treated mice undergoing the FMD cycles have improved capacity to clear exogenous blood glucose, compared to mice on the regular chow (AL)(FIG. 2D).

Levels of certain circulating cytokines have been used as indicators to determine islet pathological status in patients with recent-onset T1D (Baeyens et al., 2014; Grunnet et al., 2009; Lebastchi and Herold, 2012). We performed a 23-plex immunoassay to determine the effects of the FMD on inflammatory markers. We found that FMD cycles not only suppressed the circulating cytokines associated with β-cell damage (e.g. TNFalpha and IL-12) but also increased circulating cytokines associated with β-cell regeneration (e.g. IL-2 and IL-10)(FIG. 2E, day 30)(Dirice et al., 2014; Rabinovitch, 1998; Zhernakova et al., 2006).

Taken together these results indicate that FMD cycles reduce inflammation and promote changes in the levels of cytokines and other proteins, which may be beneficial for the restoration of insulin secretion and the reversal of hyperglycemia.

FMD Cycles Reverse STZ-Induced β-Cell Depletion

Figure 2F:
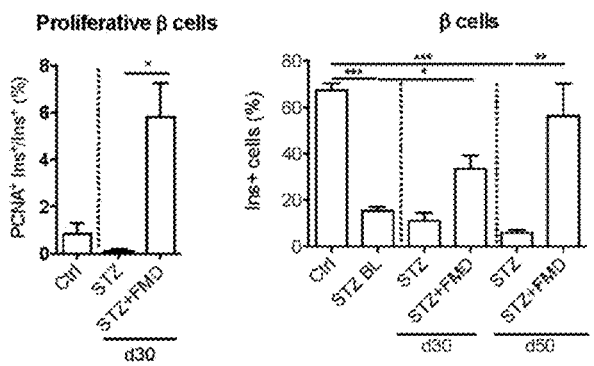
Figure 2G:
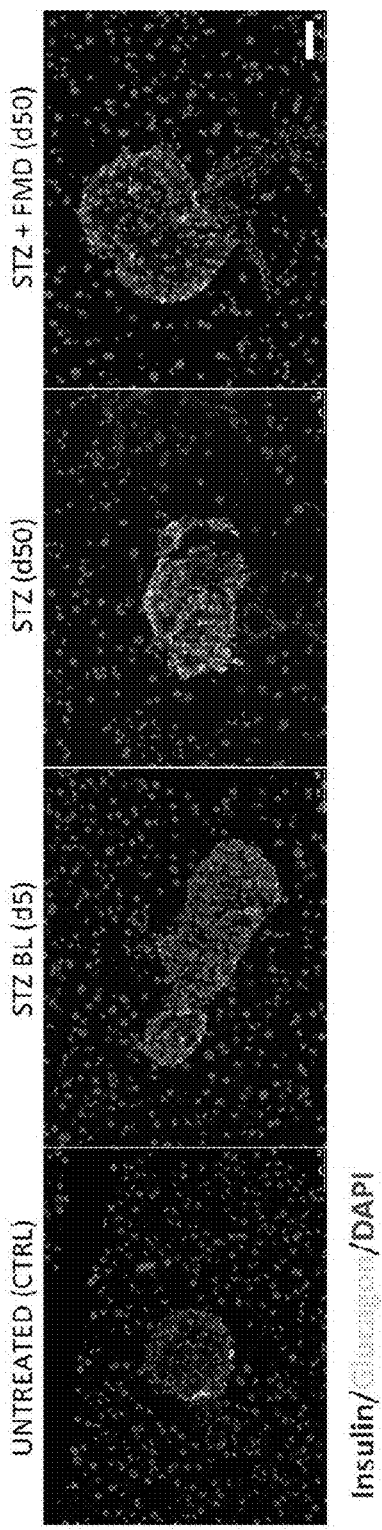

The characterization of pancreatic islet cells indicates a strong association between restored glucose homeostasis and the replenishment of pancreatic β cells in animals undergoing FMD cycles. STZ treatments resulted in an increase of non-α/β cells (FIG. 11) and an about 85% depletion of insulin-secreting β cells (FIG. 2F, STZ BL). The transient increase of non-α/β cells was reversed by d30 in both groups (FIGS. 10D and 10E). Mice receiving weekly cycles of the FMD showed a major increase in proliferative β cells followed by a return to a nearly normal level of insulin generating β cells by d50 (FIGS. 2F and 2G). In contrast, mice received ad libitum access to regular chow (AL) remained depleted of β-cells for more than 50 days (FIGS. 2F and 2G). Overall, the increase of non-α/β prior to β-cell proliferation raises the possibility that weekly cycle of the FMD might mediate the fate conversion of non-α/β cells to β cells to reverse the STZ-induced β-cell depletion, although other scenarios are possible.

FMD and Post-FMD Re-Feeding Promote β-Cell Regeneration in Non-Diabetic Mice

Figure 3A:
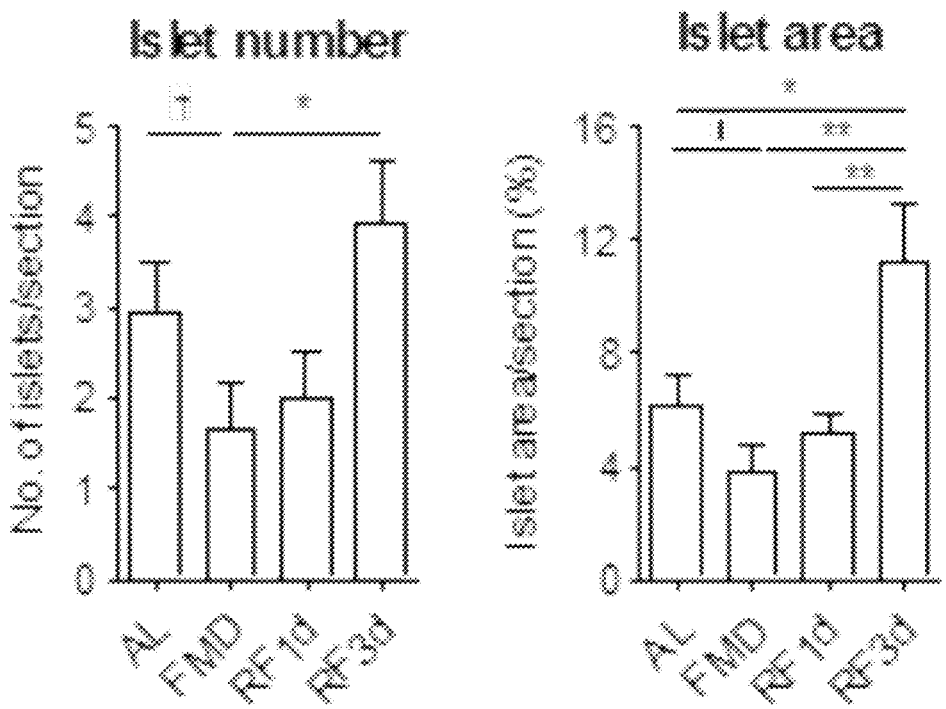
Figure 3B:
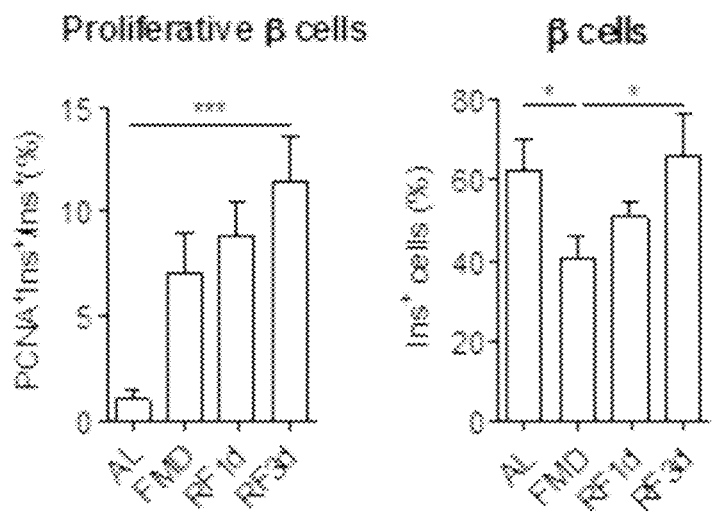
Figure 3C:
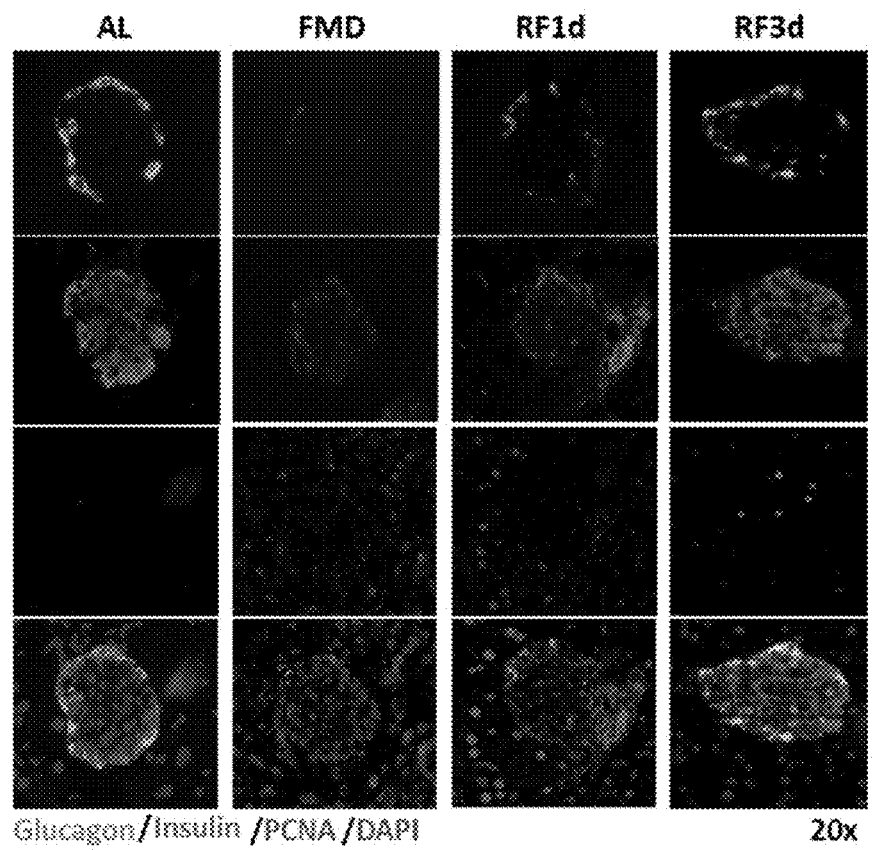
Figure 3D:
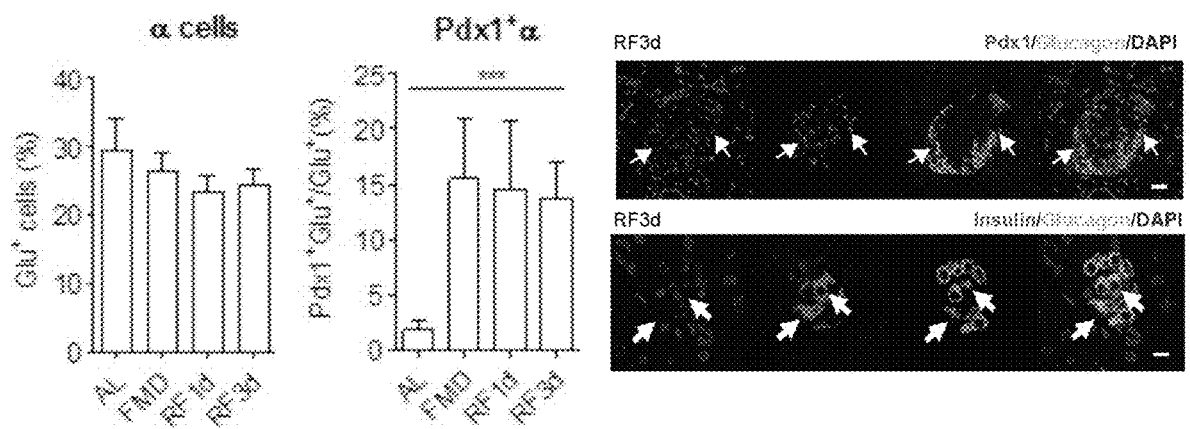
Figure 3E:
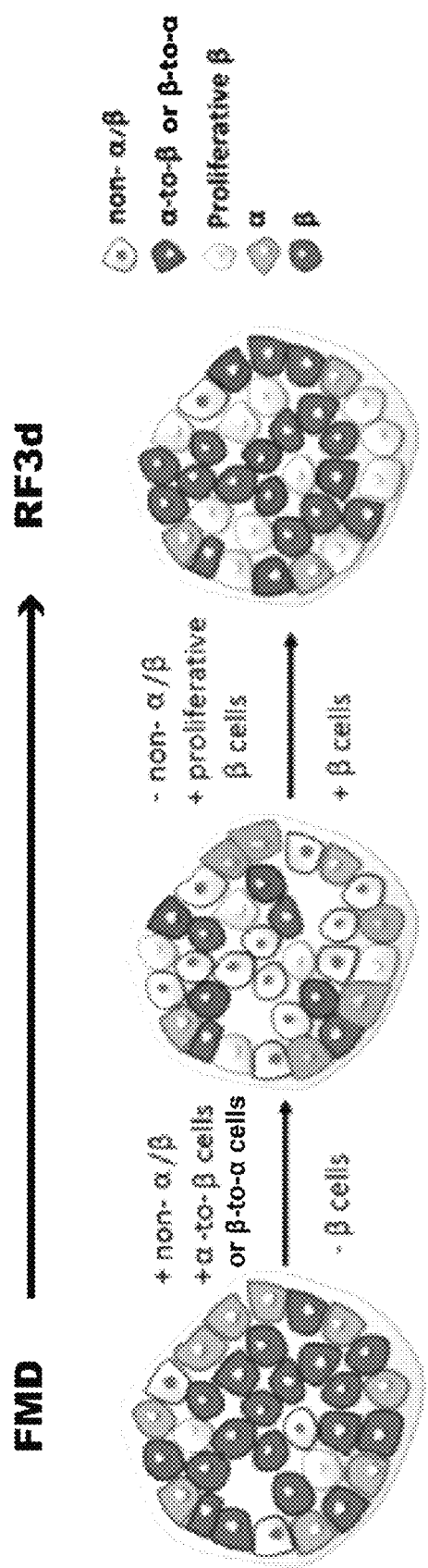

We investigated whether and how the FMD and the post-FMD re-feeding period could regulate the cell populations within the islets to promote β-cell regeneration independently of diabetes, with a focus on the non-α/β cells and proliferative β cells. To characterize cellular and hormonal changes, pancreatic samples and peripheral blood of wild-type C57Bl6 mice fed with the FMD for 4 days were collected before the diet (BL), at the end of the diet (d4) and 1 day or 3 days after mice returned to the normal diet (RF1d or RF3d). The FMD caused a trend of decrease in the number and size of pancreatic islets (FIG. 3A) and reduced the proportion of β cells by 35% (FIGS. 3B and 3C, see also FIG. 12 for absolute numbers). These effects were reversed within three days of re-feeding (FIGS. 3A and 3C). Non-α/β cells begun to proliferate at the end of the FMD and this proliferation persisted until 1 day after re-feeding (RF1d), leading to a 2.5-fold increase in non-α/β cells (proportion per islet) at RF1d (FIG. 12). By RF3d, the number of non-α/β cells had dropped and that of β cells returned to basal levels (BL), although β cells remained in a much more proliferative state in the FMD group (FIGS. 3B and 3C). The expression of proliferation marker PCNA was elevated in β cells but not α cells after re-feeding post FMD (FIGS. 3B, 3C and 12). Despite number of α cells per islet remain the same, the transitional α-to-β or β-to-α cells that co-express both α (i.e. glucagon) and β cell (i.e. Pdx-1 or insulin) markers were increased in mice that received the FMD (FIG. 3D). In summary, the FMD promotes a decrease in the numbers of differentiated or committed cells, followed by the induction of transitional cells leading to major increases in the proliferation and number of insulin-generating β cells (FIG. 3E).

Figure 4A:
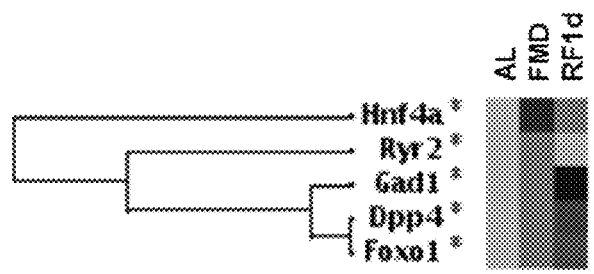
Figure 4B:
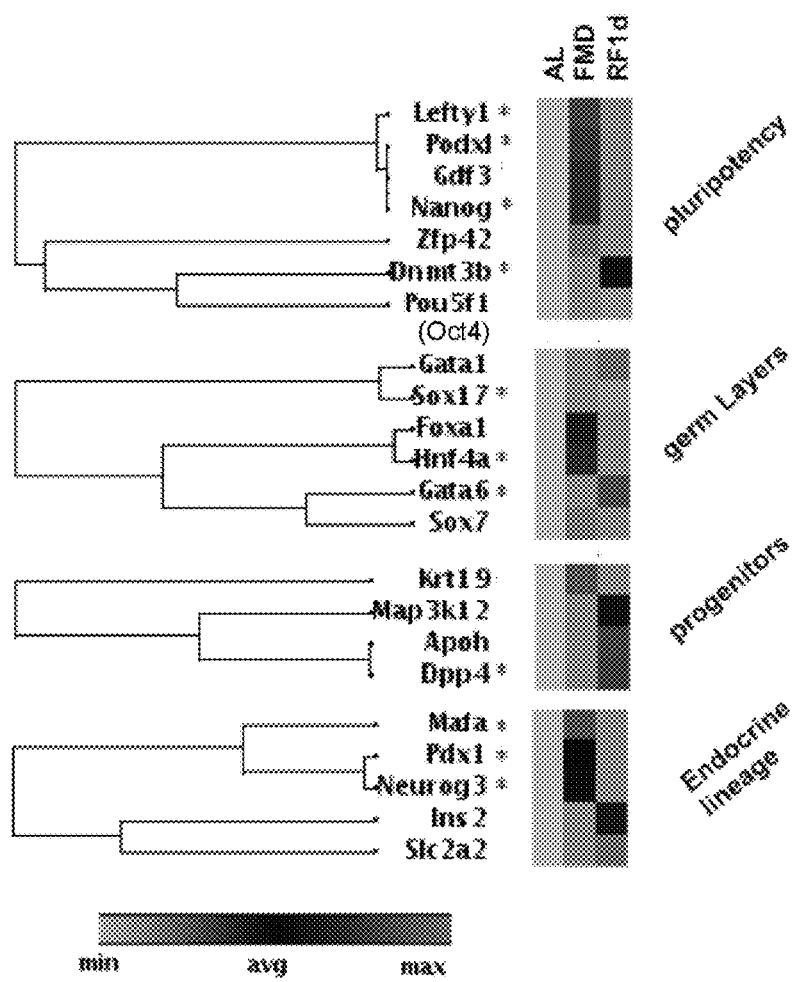
Figure 4C:
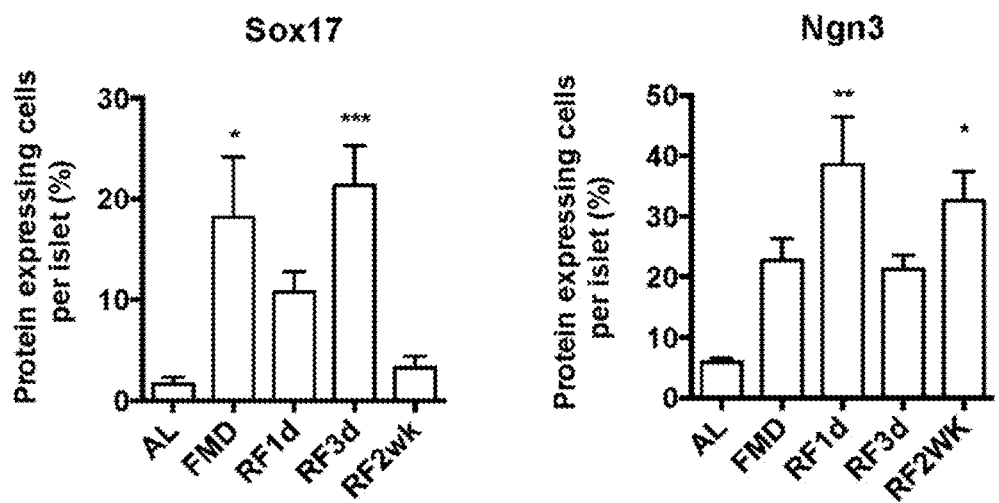
Figure 4D:
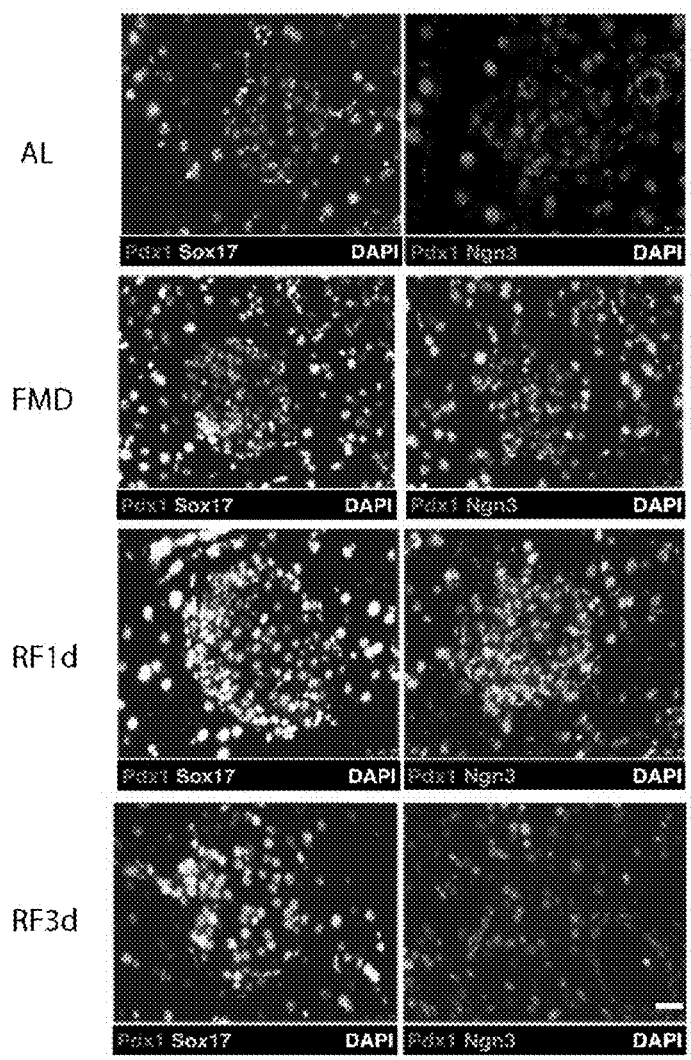

FMD Promotes a Gene Expression Profile in Adult Mice Similar to that Observed During Embryonic and Fetal Development To identify the genes that may mediate the FMD-induced pancreatic regeneration we measured gene expression in pancreatic islets at the end of the FMD and post-FMD re-feeding. At both time points, we observed a transient up-regulation of Foxo1 (6.9 fold at FMD, 5.3 fold at RF1d, *p<0.05 comparing to AL) and of a set of genes that have been previously identified as dual regulators for both fat-metabolism and fate-determination in mammalian cells (Cook et al., 2015; Haeusler et al., 2014; Johnson et al., 2004; Kim-Muller et al., 2014; Mu et al., 2006; Stanger, 2008; Talchai et al., 2012; Talchai and Accili, 2015; Tonne et al.)(FIG. 4A), in agreement with the metabolic changes found in mice receiving the FMD (FIG. 9). We further examined whether the metabolic reprogramming caused by the FMD affects lineage determination in pancreatic islets. In FIG. 4B, the expression of lineage markers was determined by the mRNA expression of purified islets from mice fed ad libitum (AL) or the FMD. Results from the qPCR array indicate that up-regulation of the following genes was statistically significant (*p<0.05 comparing to AL, FIG. 4B; see also FIG. 13): i) pluripotency markers (e.g. Lefty1, 3.0 fold during FMD, 7.0 fold at RF1d; Podx1, 3.9 fold during FMD, 9.8 fold at RF1d; Nanog, 2.6 fold during FMD and 5.4 fold RF1d and Dnmt3b, 31.6 fold during FMD and 18.3 fold RF1d), ii) embryonic development markers (e.g. Sox17, 3.4 fold during FMD and Gata6 3.1 fold during FMD and 2.7 fold at RF1d), iii) pancreatic fetal stage markers and iv) β-cell reprogramming markers (e.g. Mafa, 4.7 fold at RF1d; Pdx-1 3 fold during FMD, 5.07 fold at RF1d; and Ngn3, 21.5 fold during FMD, 45.6 fold at RF1d.) (FIG. 4B)(Zhou et al., 2008). These changes in gene expression suggest that the FMD either causes: i) a de-differentiation of pancreatic cells towards pluripotency at the end of the diet followed by re-differentiation to pancreatic β-cell lineage during early re-feeding (RF1d) or ii) recruitment of cells with these features from outside of the pancreatic islets. The assessment of protein expression of cells within the islets was also carried out by immunostaining for key proteins associated with pancreatic development (FIGS. 4C and 4D). In agreement with the results of qPCR array (FIG. 4B), we found that protein levels of Sox17, as the early lineage marker, were elevated at the end of the FMD (FMD-4d) and protein levels of Ngn3, a marker for endocrine progenitors, were transiently up-regulated during early re-feeding (FMD-4d to RF1d)(FIG. 4C).

To determine whether step-wise β-cell conversion from the dedifferentiated cells occurs during early refeeding, we performed double-staining for the targeted developmental markers (i.e. Sox17, Pdx-1, Ngn3), across the time points of FMD. We also measured the expression of Oct4 (Pou5f1), which has been previously reported to be expressed in the nucleus of adult pancreatic islets in association with Foxo-1 related diabetic β-cell dedifferentiation (Talchai et al., 2012; Xiao et al., 2013). Oct4 (Pou5f1) mRNA expression showed a trend for an increase in mice on the FMD, which is not significant (FIG. 4C, p>0.05). Results of immunostaining indicate that Oct4 (Pou5f1) and Sox17 may only be co-expressed very transiently after overnight re-feeding (FIG. 13B, RF12 hr) followed by robust expansion of Sox17$^+$Pdx1$^+$ and then Pdx1$^+$Ngn3$^+$ cells at RF1d (FIG. 4D and see also FIG. 13B for all time points). Although Ngn3+ cells were also detectable in AL mice, they were mainly located outside or on the edge of the islets, in agreement with what was reported in previous studies (Baeyens et al., 2014; Gomez et al., 2015) (FIG. 4D). The number of Ngn3+ cells was increased both inside and outside the islets during the FMD and re-feeding (FIG. 4D).

These results suggest that as a result of the FMD and re-feeding cycle, the pancreatic islets contain an elevated number of cells with features of progenitor cells, which may differentiate and generate insulin-producing cells.

FMD Induces Ngn3 Expression to Generate Insulin-Producing β Cells

Figure 5A:
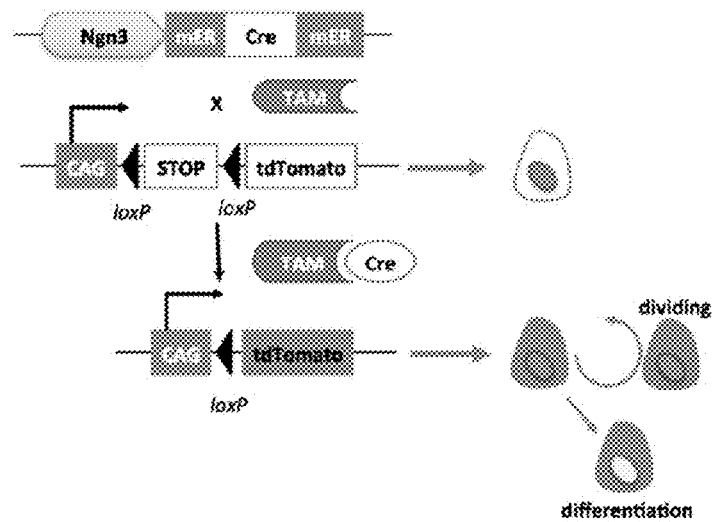
Figure 5B:
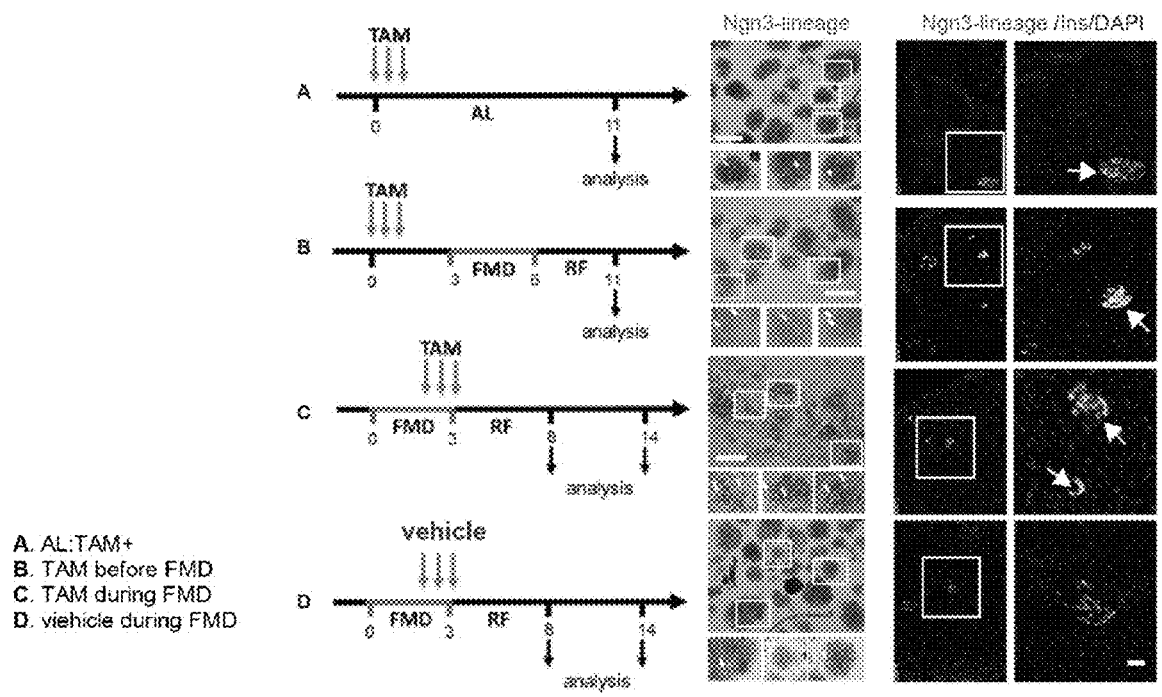
Figure 5C:
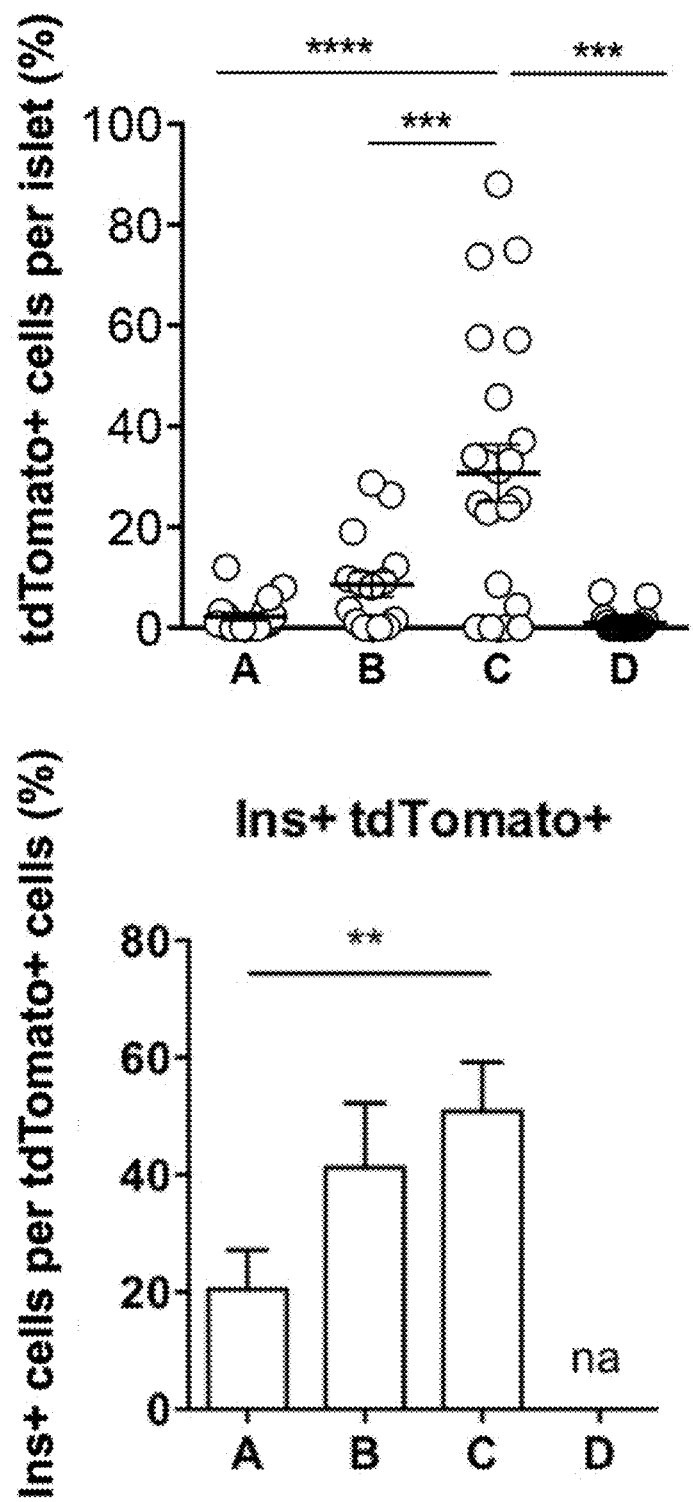

Ngn3+ cells within the pancreatic islets have been previously described as progenitor cells able to generate all lineages of endocrine cells including the insulin-producing β cells, although the role of Ngn3 in adult β-cell regeneration remains unclear (Baeyens et al., 2014; Van de Casteele et al., 2013; Xu et al., 2008). To investigate whether the FMD causes de novo expression of Ngn3 and whether Ngn3+ cells may contribute to FMD-induced β-cell regeneration, we generated Ngn3-CreER;tdTomato$^{LSL}$-reporter mice to trace the lineage of putative Ngn3-expressing cells and their progeny in the adult mice treated with the FMD (FIG. 5A). To initiate the loxP recombination for lineage tracing, low-dose tamoxifen injections (2 mg per day, for 3 days) inducing the recombination (maximized at 48 hr and minimized within a week) were given to mice before or after the FMD and to mice fed ad libitum (AL control) (FIG. 5A). Tissue collection time points are relative to the time of injection and to that of FMD treatments (FIG. 5A). Results indicate that the FMD induced the expansion of the Ngn3-derived lineages (FIGS. 5B and 5C). Characterization of tdTomato+ cells by immunostaining indicates that tdTomato+ cells contributed 50.8±8.3% of the overall beta cell pool following the FMD (FIG. 5C, group C).

Figure 5D:
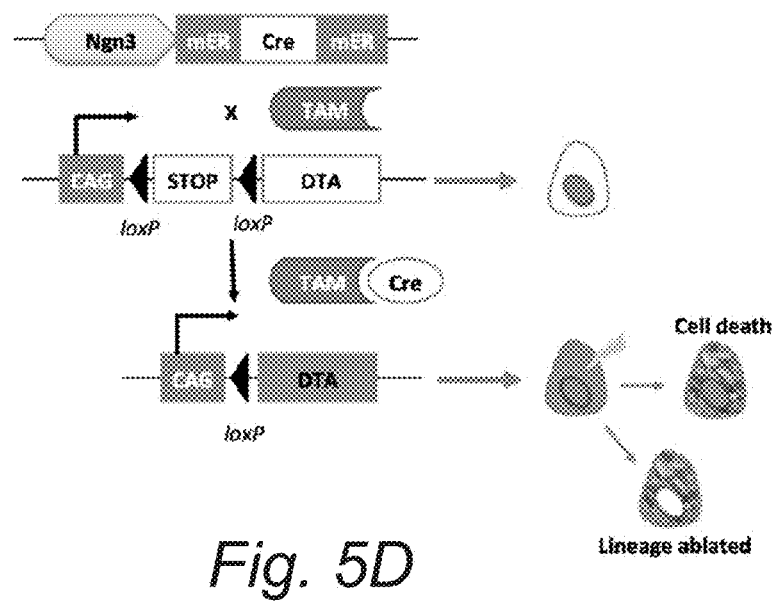
Figure 5E:
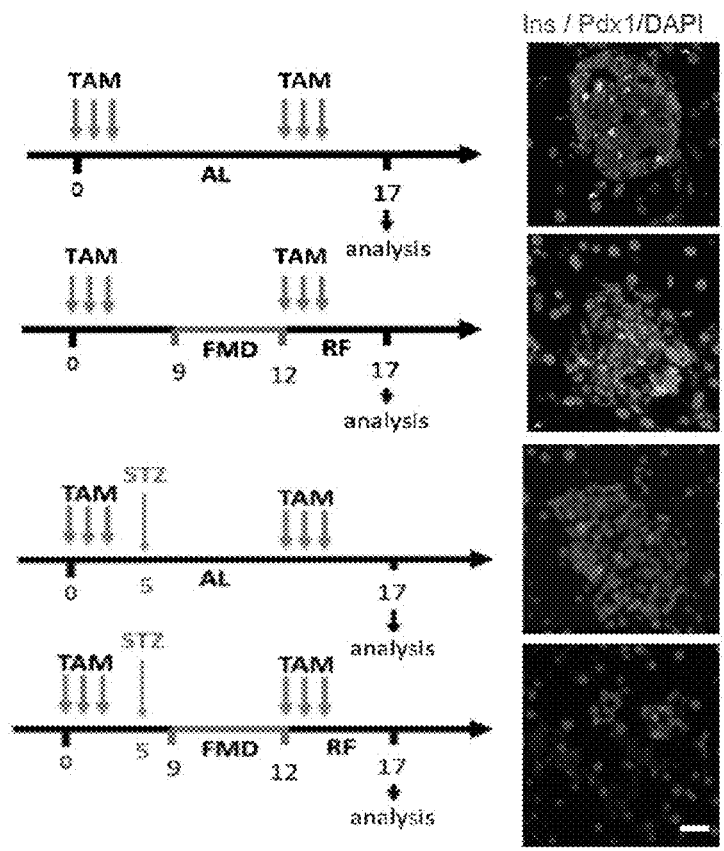
Figure 5G:
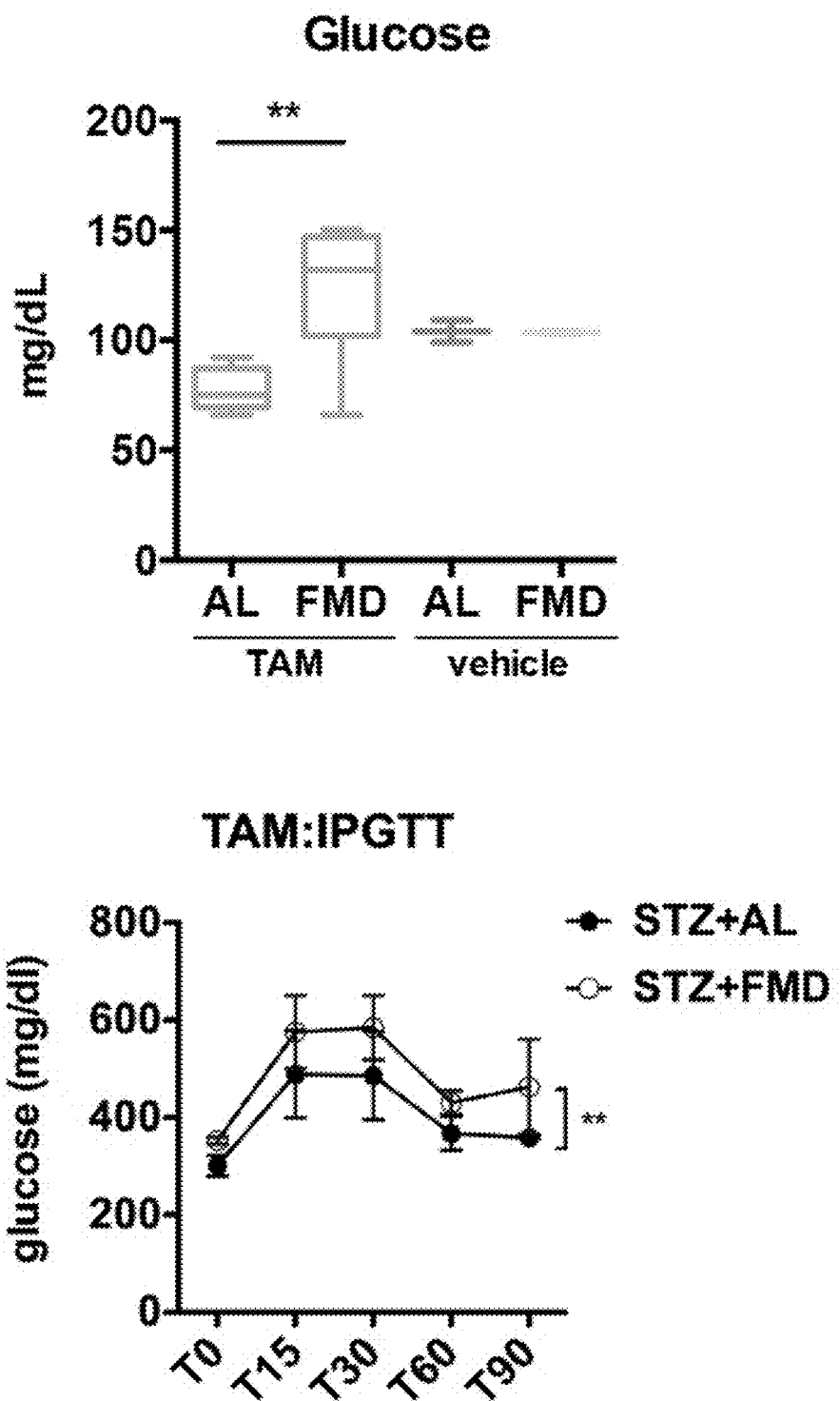

To confirm the contribution of FMD-induced Ngn3 lineages in reconstituting insulin-secreting beta cells, we generated another mouse model (Ngn3-CreER/LSL-R26R$^{DTA}$) and performed lineage-ablation experiments in both wild-type non-diabetic mice and STZ-treated mice (FIG. 5D). The results indicate that ablation of Ngn3+ lineage reversed FMD-induced β-cell regeneration and its effects on fasting glucose levels in the naïve wild-type mice (FIGS. 5E, 5F and 13) and that on glucose clearance capacities (IPGTT assay) in STZ-treated diabetic mice (FIG. 5G), confirming the FMD-induced generation of an Ngn3-lineage and suggesting a critical role for this Ngn3-dependent β-cell neogenesis in glucose homeostasis.

Fasting Conditions or Inhibition of Nutrient Signaling Pathways Promote Ngn3 Expression and Insulin Production in Human Pancreatic Cells In both mouse and humans, Ngn3 expression occurs right before and during endocrine cell generation. Ngn3 mRNA expression in the developing mouse pancreas peaks around E15.5, which is roughly equivalent to week 7-8 (Carnegie Stages 21-22) in human development. Expression of Ngn3 in adult mouse islets, although rare, has been demonstrated by rigorous lineage reporter analysis (Wang et al., 2009). In agreement with results from others, our data (FIGS. 5 and 13) indicate that Ngn3+ cells in adult pancreas islets are important for beta-cell regeneration in mice. On the other hand, the role of Ngn3 in human islet development and β-cell regeneration in adulthood remains poorly understood (McKnight et al., 2010).

Figure 6A:
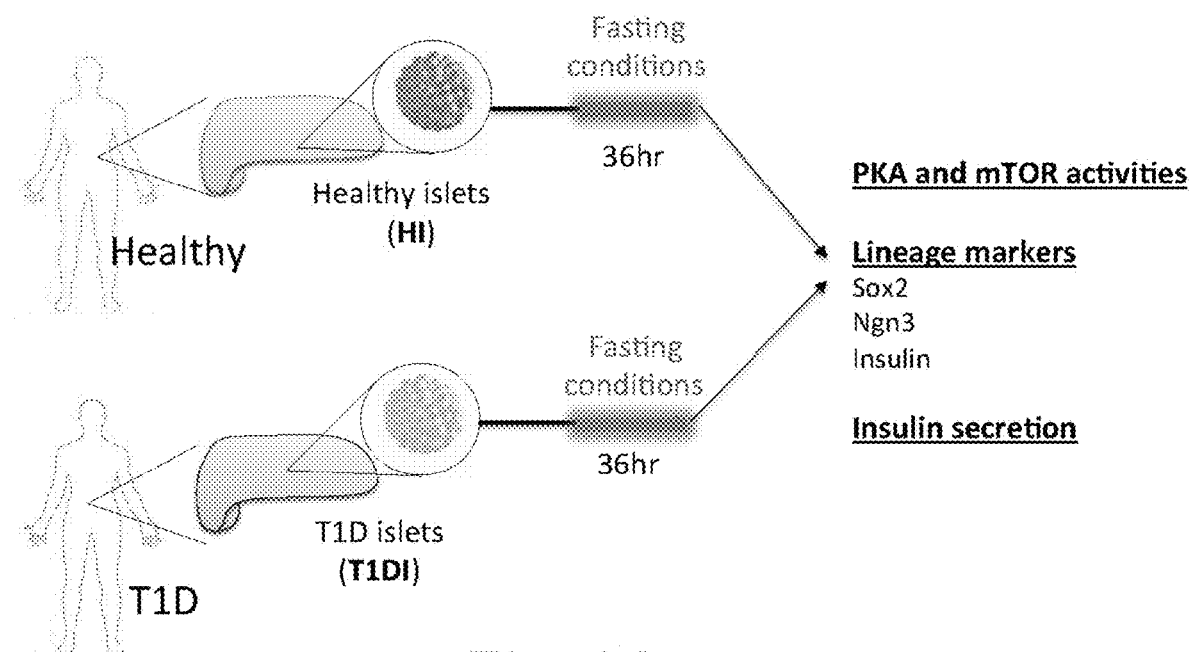
Figure 6B:
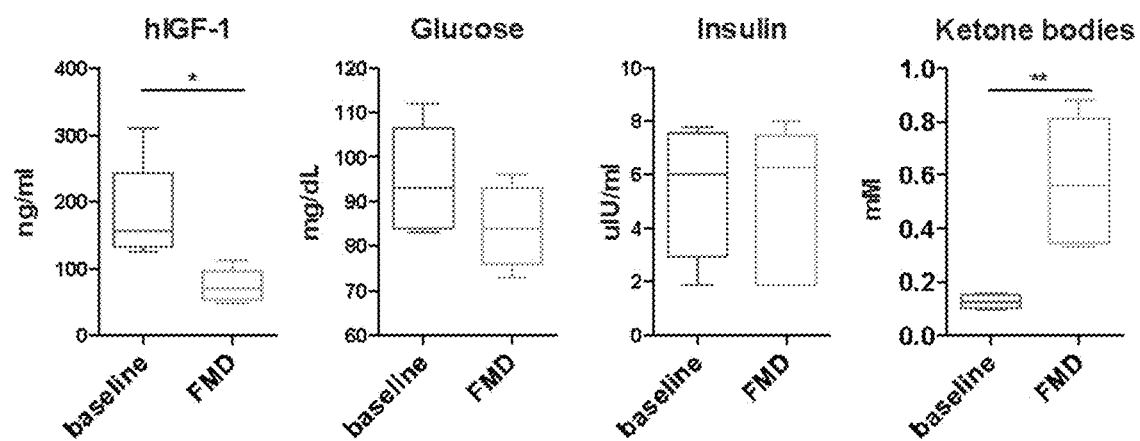

To investigate how the fasting mimicking conditions affect Ngn3 expression and β-cell functions in human pancreatic cells, we performed ex vivo experiments using primary human pancreatic islets (FIG. 6A). Briefly, the pancreatic islets from healthy and T1D subjects (HI and T1DI, respectively) were cultured according to the manufacturer's instructions. The cultured islets were then treated with serum from subjects enrolled in a clinical trial testing the effects of a low protein and low calorie FMD lasting 5 days (NCT02158897)[17]. Serum samples were collected at baseline and at day 5 of the fasting mimicking diet in 5 subjects. We then measured IGF-1, glucose and ketone bodies and treated human pancreatic islets with the subject-derived serum (FIG. 6B, Table 2 (FIG. 7). In both healthy islets and T1D islets exposed to the serum of FMD-treated subjects, we observed a trend for glucose-dependent induction in the expression of Sox2 and Ngn3 (FIG. 14A).

Figure 6C:
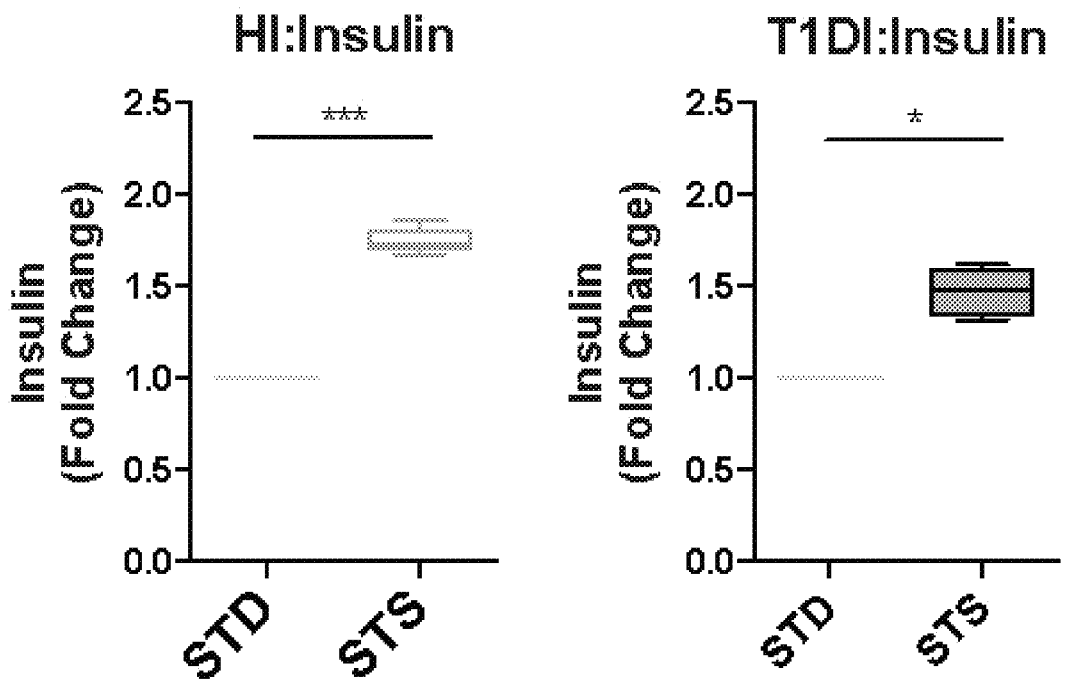
Figure 6D:
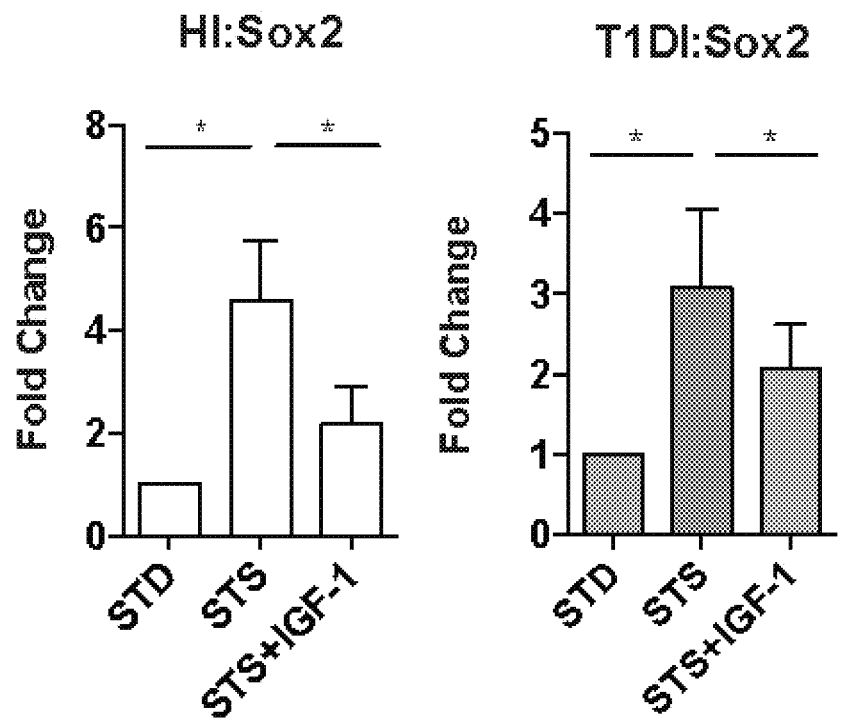
Figure 6E:
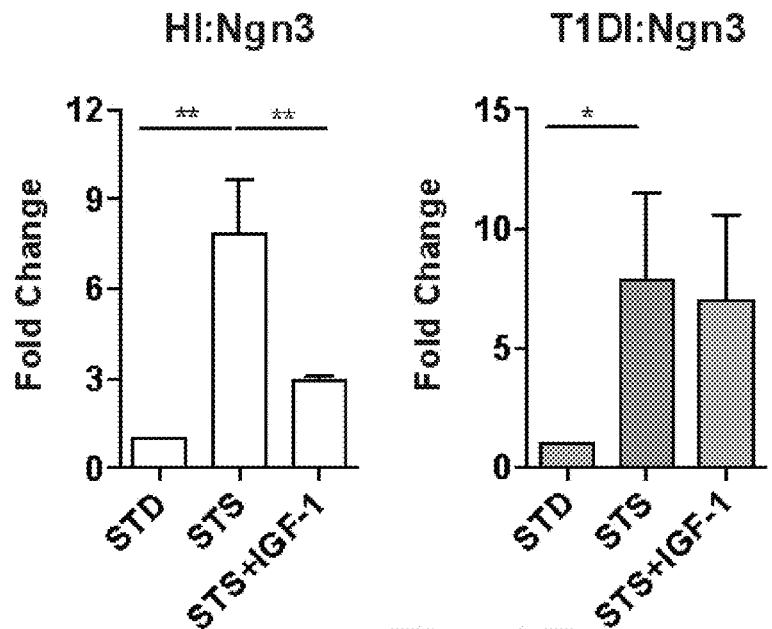
Figure 6F:
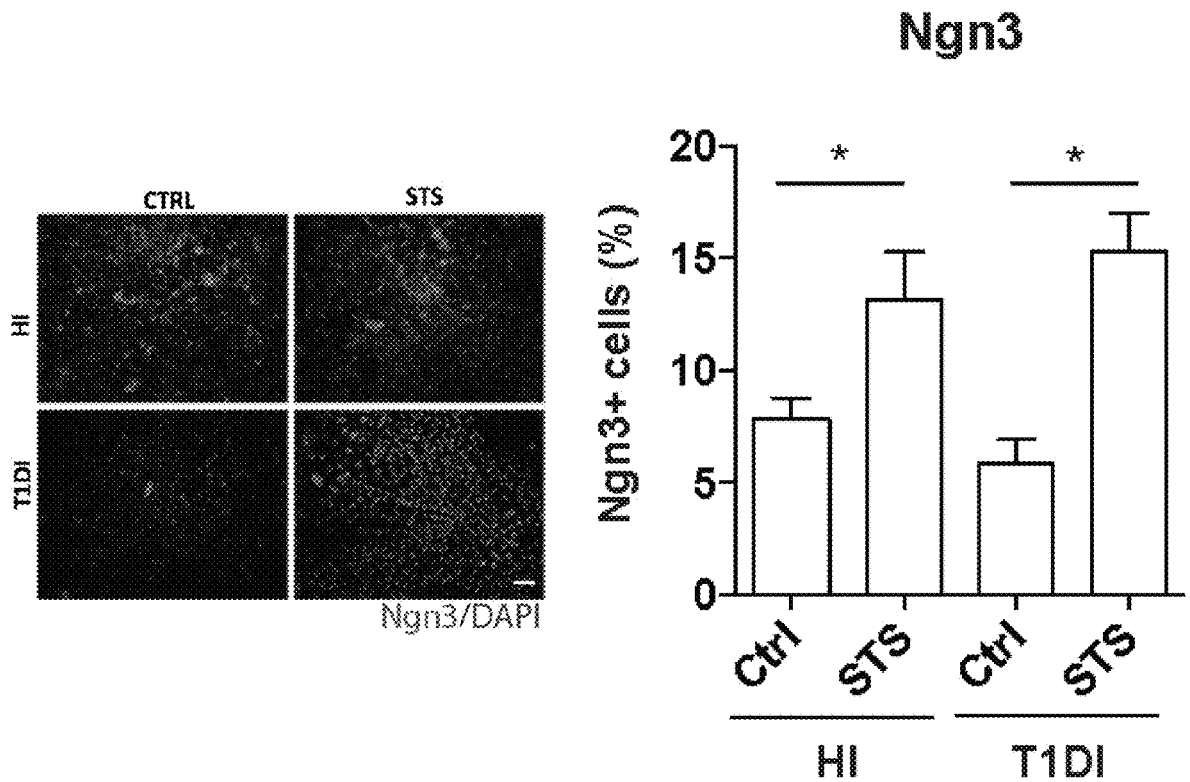
Figure 6G:
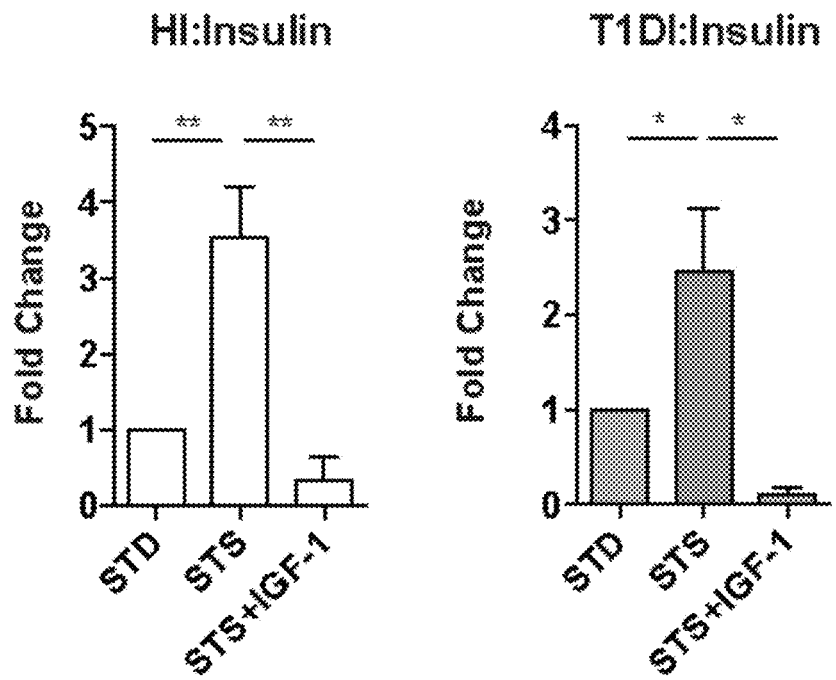

We then applied the low-glucose and low-serum fasting mimicking medium (STS) to the cultured pancreatic islets, and found that it significantly stimulated the secretion of insulin in both HI and T1DI (FIG. 6C). We further investigated the expression of lineage reprogramming markers, which we found to be up-regulated in mice as a result of the FMD-treatment (i.e. Nanog, Sox17, Sox2, Ngn3 and Ins). The results indicate that the fasting mimicking conditions had strong effects in inducing the expression of Sox2, Ngn3 and insulin in human pancreatic islets from healthy (healthy islets, HI) and T1D subjects (T1D islets, T1DI) (FIG. 6D-F). In cells from normal human subjects, these effects were reversed by IGF-1 treatment (FIG. 6G). Notably, in human T1D cells, IGF-1 reversed the increased insulin and Sox 2 gene expression but not that of Ngn3 expression caused by the STS medium (FIG. 6G vs. FIGS. 6D and 6E). Future studies are warranted to further investigate the role of circulating IGF-1 in the expression of lineage reprogramming markers and pancreatic islet cells regeneration in vivo.

Figure 6H:
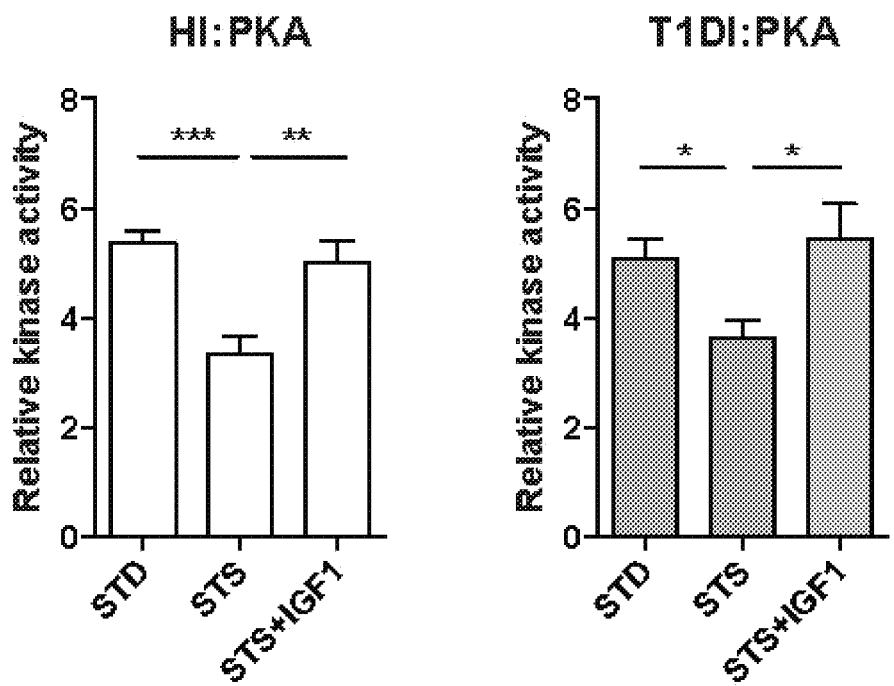
Figure 6I:
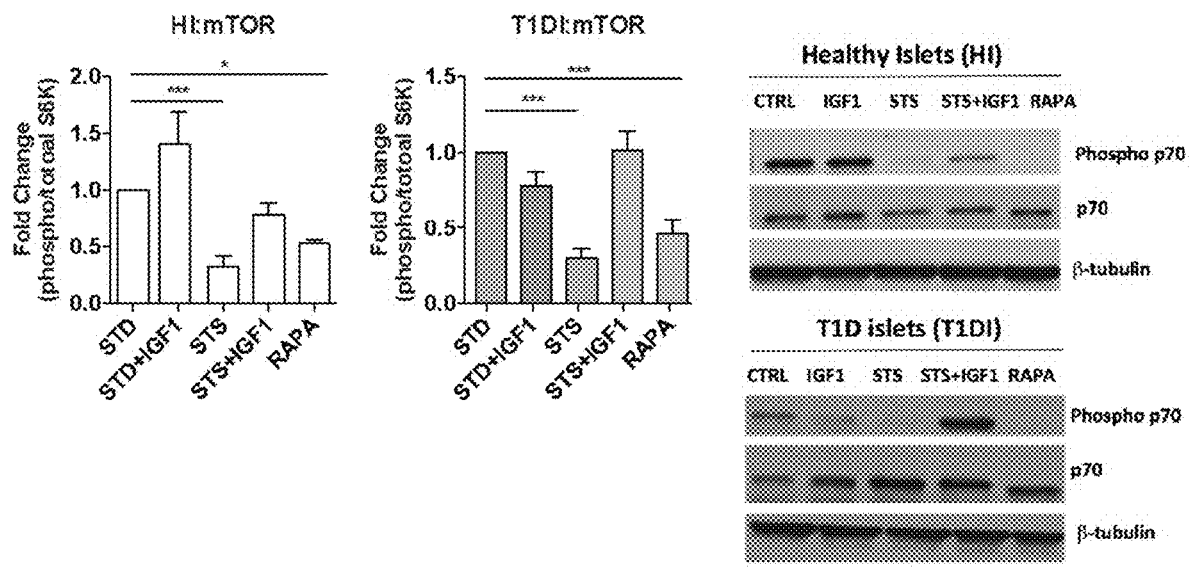
Figure 6J:
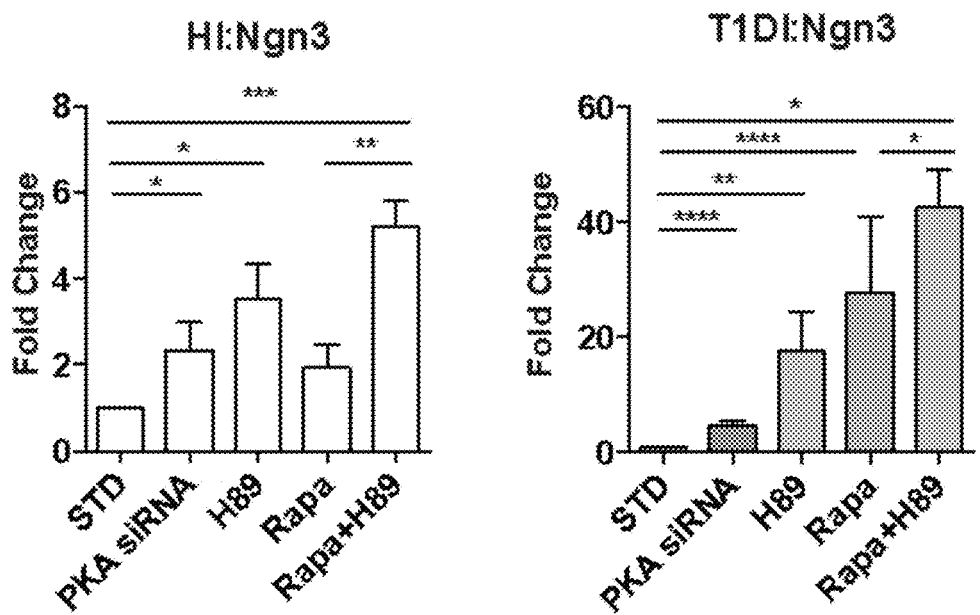
Figure 6K:
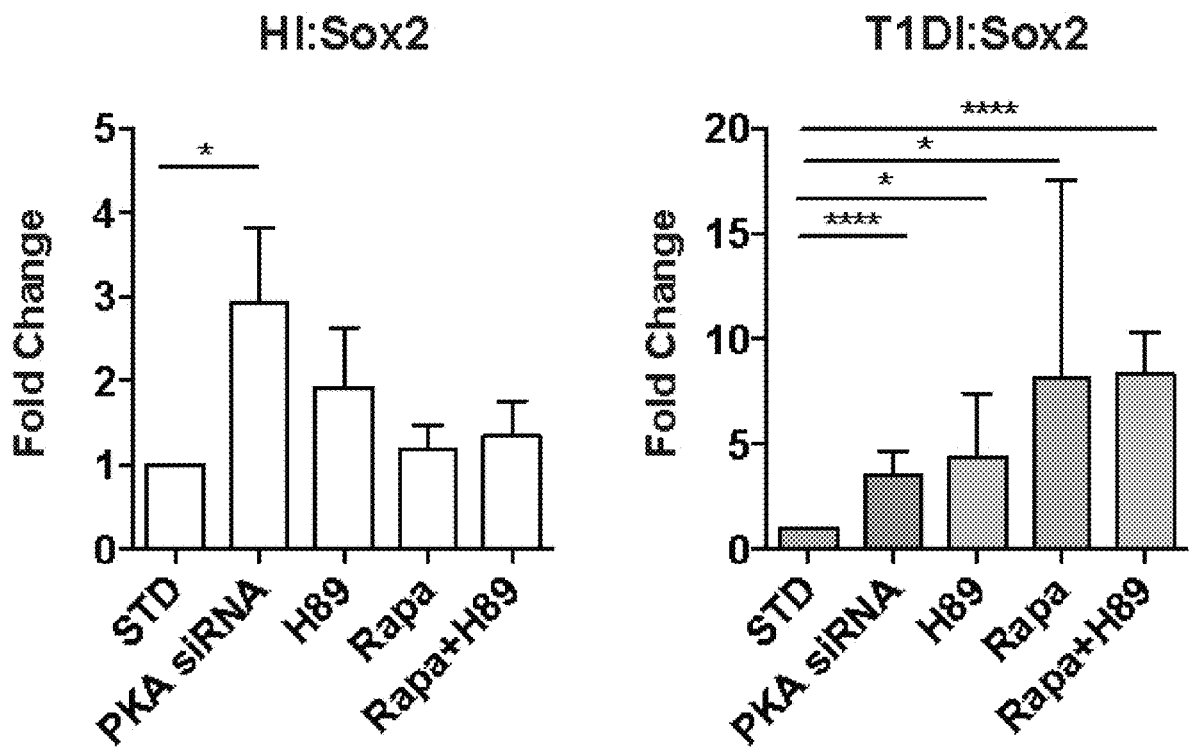
Figure 9A:
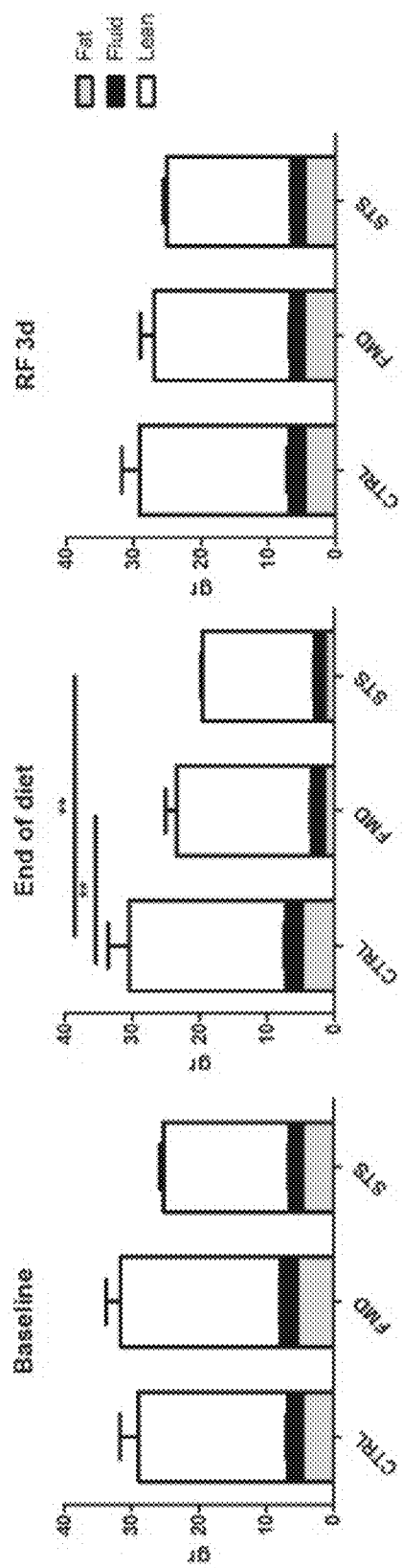
Figure 9B:
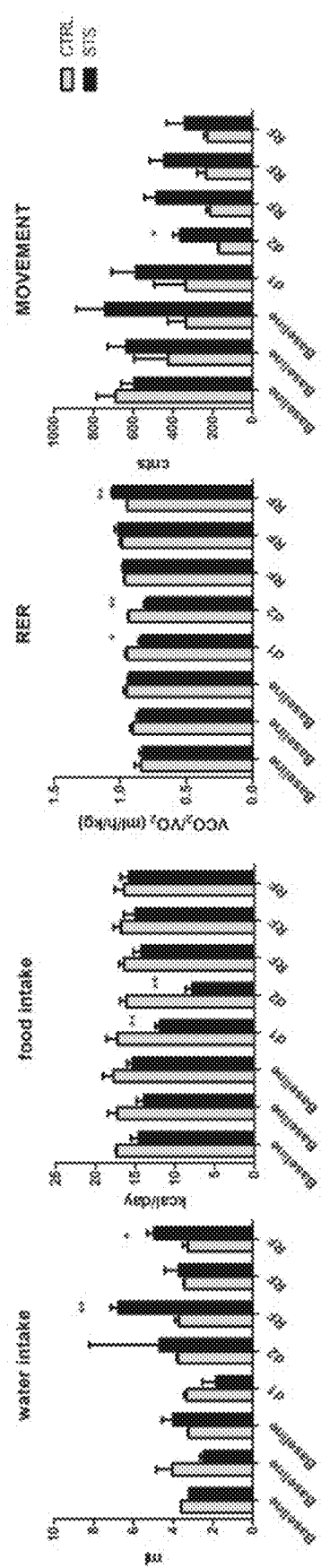
Figure 9C:
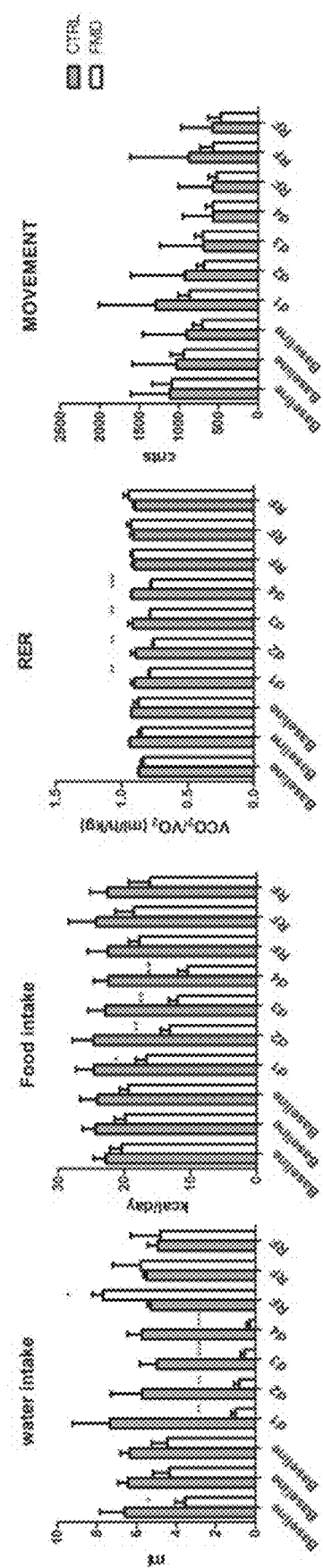
Figure 9D:
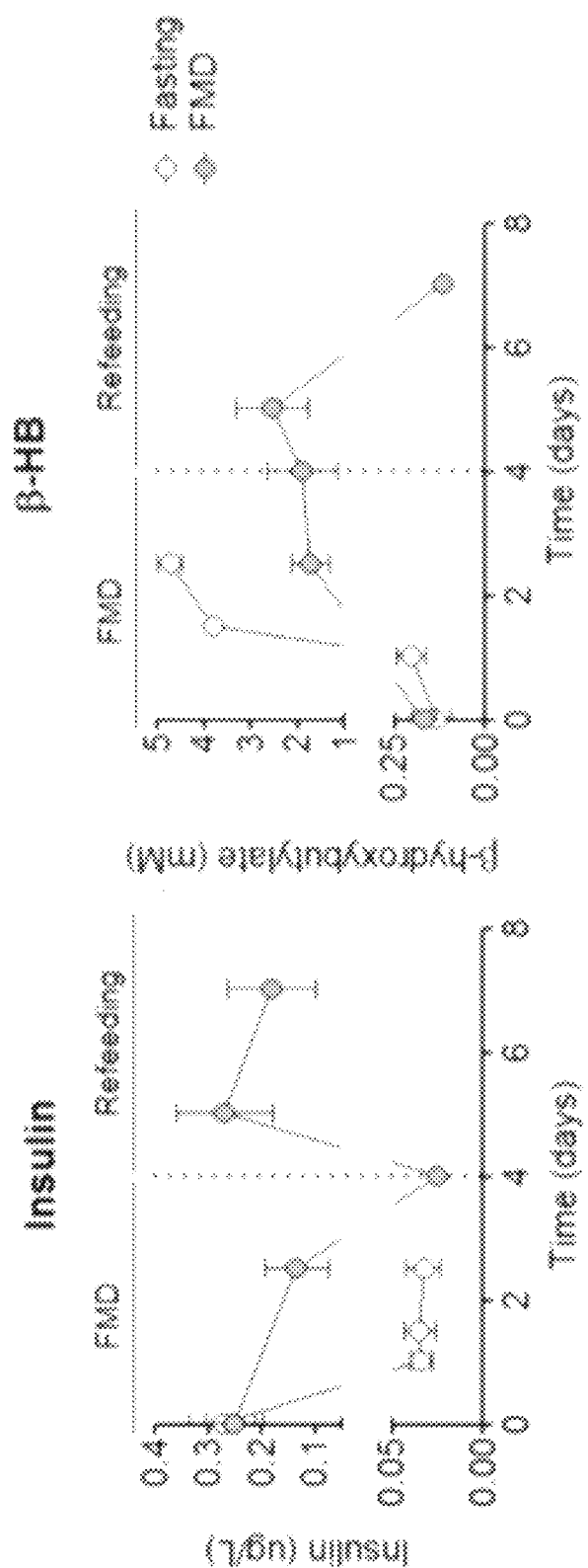

In both healthy and T1D human islets, STS medium significantly reduced the activity of PKA, an effect reversed by IGF-1 treatment (FIG. 6H). It also dampened the activity of mTOR, which is a key mediator of amino acid signaling (FIG. 6I). To further investigate the role of these nutrient sensing signaling pathways in regulating the expression of lineage markers (i.e. Sox2 and Ngn3), we tested the role of the Tor-S6K and PKA pathways, which function downstream of IGF-1, in the reprogramming of pancreatic cells. Human pancreatic islets cultured in standard medium were treated with rapamycin, which inhibits mTOR, and H89, which inhibits PKA. mTOR and PKA were implicated by our group and others in the regeneration of other cell types (Cheng et al., 2014; Yilmaz et al., 2012). We found that in human islets from T1D subjects (T1DI), expression of the essential lineage markers Sox2 and Ngn3 was not induced by inhibition of either mTOR or PKA, but was significantly induced when both mTOR and PKA were inhibited (FIGS. 6J and 6K). Interestingly, the constitutive mTOR, but not PKA, activity is trending higher in HI compared to T1D1 cells (FIG. 6I, lane 1 for both sets for mTOR activity and FIG. 6H for PKA activity), which may explain the overall differences between HI and T1DI in Sox2 and Ngn3 expression shown in FIG. 6J. Taken together, these results indicate that fasting may be effective in promoting lineage reprogramming and insulin generation in pancreatic islet cells, in part by reducing IGF-1 and inhibiting both Tor and PKA signaling. Pancreatic cells from T1D subjects displayed constitutively elevated activity of Tor-S6K and PKA, which points to the potential for inhibitors of both pathways in the induction of Ngn3-mediated lineage reprogramming. These results raise the possibility that the effect of the FMD on pancreatic regeneration in T1D subjects could be mimicked or enhanced by pharmacological inhibition of these pathways.

DISCUSSION

During mouse development, at embryonic day E8.5, pancreatic progenitor cells co-express the SRY-Related HMG-Box transcription factors Sox17 and homeodomain transcription factor Pdx1. These multipotent pancreatic progenitors are then converted into bipotent epithelial cells that generate duct cells or a transient population of endocrine precursor cells expressing the bHLH factor Neurogenin3 (Ngn3). $Ngn3^+$ endocrine precursors give rise to all the principal islet endocrine cells including $glucagon^+$ $\alpha$ cells and $insulin^+\beta$ cells (Arnes et al., 2012). In mice, expression of Ngn3 in the developing pancreas is transient, detectable between E11.5 and E18 (Arnes et al., 2012). Whether developmental genes including Sox17, Pdx-1 and Ngn3 could be activated to generate functional β-cells in adults was previously unknown.

Both cell-based therapy and the use of cytokines and hormones that stimulate β-cell self-replication have the potential to restore insulin-producing β cells in diabetic patients (Dirice et al., 2014). However, despite some success with transplantation-based therapy, the short supply of donor pancreata plus the inefficient conversion of stem cells into specialized derivatives have represented obstacles for clinical application, suggesting that a successful β-cell regeneration might depend on the coordinated activation and re-programming of endogenous progenitors (Blum et al., 2014; Sneddon et al., 2012; Wang et al.; Xiao et al., 2013). Recently, this in vivo lineage reprogramming or transdifferentiation, has become an emerging strategy to regenerate β cells (Cohen and Melton, 2011; Heinrich et al., 2015) (Abad et al., 2013; Xu et al., 2015).

In this study, we discovered that a low protein and low sugar fasting mimicking diet (FMD) causes a temporary reduction in β-cell number followed by its return to normal levels after re-feeding, suggesting an in vivo lineage reprogramming. We show that the severe hyperglycemia and insulinemia in both the late stage $Lepr^{db/db}$ T2 and the STZ-treated T1 mouse diabetes models were associated with severe β-cell deficiency in pancreatic islets. 6-to-8 cycles of the FMD and re-feeding were required to restore the β-cell mass, insulin secretion function and to return the 6 hr-fasting blood glucose to nearly normal levels. In non-diabetic wild-type mice, the portion of beta cells per islet, as well as the total number of β cells per pancreas was reduced by about 60% at the end of a 4-day FMD but their normal level was completely restored within 3-to-5 days post re-feeding. Also, insulin and blood glucose levels were reduced by 70% or more at the end of the FMD period but returned to normal levels within 24-to-36 hours of re-feeding. Interestingly, in diabetic mice the majority of cells residing in the islets expressed neither insulin nor glucagon (i.e. non-α/β). This phenotype was also found in non-diabetic wild-type mice during the FMD and was accompanied by an increase of other transitional cell types (i.e. Pdx1+Glucagon+ cells and Insulin+glucagon+) followed by significant β-cell regeneration upon re-feeding. This suggests that the FMD alters the gene expression profile that normally suppresses the generation of β cells. More importantly, these results suggest that dietary-induced lineage-conversion occurring prior to the β-cell proliferation may play an important role in beta-cell regeneration across the diabetic and non-diabetic mouse models. One possibility is that glucagon and insulin expression are transiently suppressed in α and β cells during the FMD, followed by lineage reprogramming in committed cells. Another possibility is that the FMD may cause cell death and then stimulate progenitor or other cells to regenerate β cells.

The FMD reversed the dedifferentiated expression profile for a number of genes associated with maturity-onset diabetes of the young (MODY) and regulated by Foxo1 (Kim-Muller et al., 2014). The FMD appears to cause pancreatic islets to first increase the expression of Foxo1 and its transcriptional targets, then induce transitionally the expression of the progenitor cell marker Ngn3+ upon re-feeding, leading to β-cell regeneration. We conclude that together with the changes in a wide range of cytokines associated with β-cell regeneration, FMD and post-FMD re-feeding generate the complex and highly coordinated conditions that promote the generation of stable insulin producing β-cells to reverse severe β-cell depletion. The key changes priming pancreatic islet cells for regeneration during the FMD, appear to be the reduction of IGF-1 levels, and the consequent down-regulation of PKA and mTor activity, in agreement with the role for these pathways in hematopoietic (Cheng et al., 2014) and intestinal stem cell self-renewal (Yilmaz et al., 2012). It was proposed that transient dedifferentiation of β-cells may play a role in their in vivo dynamics (Kim-Muller et al., 2014; Weinberg et al., 2007). The capacity of these dedifferentiated cells to re-differentiate fundamentally changes the therapeutic potential of existing cells in promoting β-cell regeneration and reverse T1D symptoms (Blum et al., 2014; Wang et al., 2014). Thus, our study provides an example of a potent and coordinated dietary regulation of cell fate-determination with the potential to serve as a therapeutic intervention to treat diabetes and other degenerative diseases. Our preliminary results from a pilot clinical trial also indicate that the use of periodic cycles of a prolonged FMD is feasible and ready to be tested in large randomized clinical trials for effects on both insulin resistance and pancreatic β-cell regeneration for the treatment of both T1D and T2D.

Experimental Model and Subject Details Mouse Models.

All animal protocols were approved by the Institutional Animal Care and Use Committee (IACUC) of the University of Southern California (USC). All mice were maintained in a pathogen-free environment and housed in clear shoebox cages in groups of five animals per cage with constant temperature and humidity and 12 hr/12 hr light/dark cycle. Prior to supplying the FMD diet, animals were transferred into fresh cages to avoid feeding on residual chow and coprophagy. All animals had access to water at all times. Unless otherwise on experimental diets, mice were fed ad libitum with regular chow (e.g. AIN93G).

T1D:

High-dose streptozotocin (STZ) injection (150 mg/kg) for inducing T1D was performed to cause β-cell depletion (>70% loss) and hyperglycemia (>250 dl/ml)(Wu and Huan, 2008). Male C57B16 mice (16 weeks, n=18) were weighed and fasted 4 to 6 hours prior to STZ injection. Briefly, STZ was dissolved in sodium citrate buffer (pH 4.5, freshly prepared) at a concentration of 10 mg/ml immediately prior to use and STZ solution was administered intraperitoneally (IP) within 5 minutes from preparation according to mice weight. An equal volume of citrate buffer was injected into male and female C57B16 mice (4- to 8-months-old, n=18) that were used as healthy controls. Mice were returned to their cage and food was replaced and 10% sucrose water was provided to prevent hypoglycemia in the days immediately following STZ injection. T2D: Ten-week-old male BKS.Cg-+Lepr$^{db}$/+Lepr$^{db}$/Jcl (db/db) mice and BKS.Cg-m+/m+/Jcl (m/m) control mice (n=15 for db/db and n=7 for control) were purchased from The Jackson Laboratory. Age-matched wild-type littermates were used as the healthy controls. Unless otherwise specified, mice were not fasted at the time of tissue collection. All experiments and procedures were performed according to an approved protocol by the Institutional Animal Care and Use Committee at University of Southern California.

Lineage Tracing and Lineage Ablation.

Hemizygous transgenic Ngn3-CreER mice were bred with R26R$^{CAG-LSL-tdTomato}$ reporter mice for lineage tracing experiments, or bred with R26R$^{DTA}$ mice for lineage ablation experiments (Jackson Laboratory). Tamoxifen (TAM) injections were performed as previously described (Madisen et al., 2010). Briefly, 75 mg/kg TAM was injected i.p. at the interested time points (as indicated in FIG. 5B and FIG. 5F). Both sex mice (12-16 weeks old) were used n=6 for each group, n=3 for vehicle control.

Human Pancreatic Islets:

Human Pancreatic Type 1 Langerhans Cells (#35001-03) and non-diabetic control (#35002-04) were purchased from a commercial source Celprogen (Torrance, Calif.). The cells were seeded at 80% of confluence and cultured with standard medium: Celprogen, M35002-04S for healthy islets and M35001-03 S for T1D islets. The cells were plated at 10$^5$ per ml density and incubated in the appropriate size flask at 37° C. in a 5% CO2 humidified incubator. Medium were changed every 48 h. When reached 65-75% of confluence, cells were passaged with Celprogen Trypsin-EDTA (T1509-014) and subcultured for expansion.

Human Subjects (FMD):

Study subjects were recruited under protocols approved by the IRB (approval # HS-12-00391) of the University of Southern California (USC) based on established inclusion and exclusion criteria. Informed consent was obtained from all subjects. Examination and tests included, but were not limited to, blood draws through venipuncture before (AL) and after the 1$^{st}$ FMD cycle (FMD) and after 5-8 days after completion of the 3$^{rd}$ dietary intervention cycle (RF). Presented are preliminary results of a set of 6 to 8 healthy subjects (see Table 2 (FIG. 7) for profiles of these individuals).

Criteria for Inclusion of Human Subjects:

Generally healthy adult volunteers, subjects of 18-70 years of age, body mass index: 18.5 and up, ability and willingness to provide written informed consent, ability and willingness to undergo multiple cycles of a 5-day dietary regimen, ability and willingness to provide blood samples via venipuncture. Exclusion criteria: Any major medical condition and chronic diseases, mental illness including severe depression and dementia, drug dependency, hormone replacement therapy (DHEA, estrogen, thyroid, testosterone), severe hypertension (systolic BP>200 mm Hg and/or diastolic BP>105 mm Hg), underweight (BMI<18.5 kg/m2), females who are pregnant or nursing, special dietary requirements incompatible with the study interventions or food allergies, alcohol dependency). Profile: Subjects in this study are at age 49.1±6.9, with heights of 166.7±4.7 cm, with body weights of 63.32±4.8 kg at baseline and 61.36±4.3 at the end of FMD.

Method Details

Mouse Fasting Mimicking Diet (FMD):

The mouse version of the FMD is a 4-day regimen using ingredients similar to the human FMD (see Table 3 (FIG. 8)) (Brandhorst et al., 2015). All diet ingredients were thoroughly mixed and then blended together with heated hydrogel (ClearH2O, Maine). Mice was fed at 50% of normal daily calorie intake on day 1 and 10% normal daily calorie intake on days 2 to 4. All mice were supplied with fresh food during the morning hours (8 am-10 am). Naturally, FMD mice were hungry and generally consumed the supplied food within a few hours during the light cycle. Control-fed animals usually consumed the supplied food during the dark hours. Post-FMD refeeding: After the end of the day 2-4 diet, mice were fed ad libitum regular chow up to 10 days to regain body weight before starting another FMD cycles.

Blood Glucose and Insulin Measurement.

Unless otherwise specified, mice were fasted for 6 hours (morning fasting) before blood glucose measurements. Blood glucose was measured through tail vein bleeding with the use of the OneTouch UltraMini Blood Glucose Monitoring System (Lifescan, Milpitas, Calif., USA). Plasma insulin levels were determined by mouse enzyme-linked immunosorbent assay (Mercodia, Winston-Salem, N.C., USA), according to manufacturer's instructions. Whole blood was withdrawn from the facial vein, and plasma was separated by centrifugation at 14,000 rpm for 3 min in plasma separator tubes with lithium heparin (BD, Franklin Lakes, N.J., USA). Briefly, 10 mL of plasma samples and calibrators were aliquoted in a mouse monoclonal anti-insulin antibody-coated 96-well plate. Working solution containing peroxidase-conjugated anti-insulin antibody was then added to each well (100 m L per well), and the plate was put under shaking conditions at room temperature (RT) for 2 h. After six washes with washing buffer, 200 mL of 3,3',5,5'-Tetramethylbenzidine substrate was added to each well and allowed to incubate for 15 min at RT. The reaction was stopped with 0.5 mol/L H2SO4 and optical density (OD) was read at 450 nm with the use of the Victor3 multilabel plate reader (PerkinElmer, Waltham, Mass., USA). A standard curve was drawn by plotting OD450 and insulin concentration of calibrators with the use of Sigmaplot 11 data analysis software (Systat Software Inc, San Jose, Calif., USA) and used as reference to extrapolate sample values for insulin concentrations (Milanesi et al., 2012; Villani et al., 2014). The homeostatic model assessment (HOMA) is a method used to quantify insulin resistance (HOMA-IR) and beta-cell function (% B). HOMA-IR was calculated using the following formula: HOMA-B= (Fasting glucose×Insulin)/22.5. HOMA % B was calculated using the following formula: HOMA-B=(20×Fasting Insulin)/(Fasting Glucose-3.5) % (Matthews, 2001).

Intraperitoneal Glucose Tolerance Testing (IPGTT) and Insulin Tolerance Testing:

Mice were single-caged and fasted for 4 hours prior to the injections. Glucose (1.5 mg/g) or Insulin (0.75 unit/kg) was injected intraperitoneally. Blood glucose levels were measured at 5, 15, 30, 60, and 90 min after the injection.

Immunofluorescence Analysis.

Briefly, the pancreatic samples were collected without saline perfusion and immediately processed for paraffin embedding and histology as previously described (Milanesi et al., 2012; Villani et al., 2014). Tissues were fixed in 10% neutral phosphate buffer formalin (Polysciences Inc, Warrington, Pa., USA) for 1 h at 4° C. and stored in 70% ethanol overnight at 4° C.

Tissues were subsequently dehydrated through graded ethanol, toluene and finally embedded in paraffin (TissuePrep, Fisher Scientific, Pittsburgh, Pa., USA). Pancreatic sections (5 µm) were sliced with the use of a Leica RM2235 rotary microtome and dried ON. The following day sections were deparaffinized in Histochoice clearing agent (Sigma-Aldrich) and rehydrated through graded ethanol series (100%, 90%, 70%, 50% and 30%) followed by rinsing in distilled water before use. Heat-mediated antigen retrieval with antigen unmasking solution (H-3300, Vector Laboratories) was performed and sections were blocked with 2% bovine serum albumin (BSA) solution for 30 min at RT. The following primary antibodies were used: anti-insulin (Abcam, ab8304), anti-glucagon (Abcam, ab8055), anti-PCNA (Abcam, ab2426), anti-PDX1 (Abcam, ab47383). Additional antibodies used for developmental markers are Anti-Oct4 antibody—ChIP Grade (Abcam, #ab19857) and anti-Oct-4A (C30A3) rabbit mAb (Cell Signaling, 2840P), Anti-Sox17 (Santa Cruz Biotechnology #sc-17355) and Anti-NGN3 (LifeSpan Biosciences, #LS-C97692). Sections were incubated with primary antibodies in a humidified chamber for 1 hour at RT. After PBS washing, sections were incubated for 30 min at RT with secondary antibodies, respectively, Alexa-fluor 555 donkey anti-mouse immunoglobulin (Ig)G, Alexa-fluor 488 donkey anti-rabbit IgG, Alexa-fluor anti-goat 647 (dilution 1/500). All secondary fluorochrome-conjugated anitbodies were purchased from Life Technologies. Sections were mounted with Vectashield mounting medium with 40, 6-diamidino-2-phenylindole (Vector Laboratories, Burlingame, Calif., USA). The images of the stained sections were captured using a 10×, 20× or a 40× objective as indicated in figure legends with a Leica AF6000 fluorescent microscope. Double staining for Pdx1$^+$Glucagon$^+$ cells, Insulin$^+$Glucagon$^+$ cells and Ngn3-tdTomato$^+$ glucagon$^+$ cells was verified by confocal imaging (Zeiss LSM 710). Numbers of cells or areas of interest were measured from 3-5 mice per group, 6-8 pancreas sections per mouse for 20-30 islets per condition per time point. "Islet area" was measured as previously described (Brereton et al., 2014). Basically, we measure total islet cross-sectional area per 2.5 mm$^2$ pancreas section (%). Please also see FIGS. 10-12 for the absolute cell counts per islet, the numbers and/or area of islets per pancreas section.

Pancreatic Islet Isolation.

Pancreatic islets were isolated form mice as previously described (Li et al., 2009). In brief, mice were sacrificed by CO2 inhalation and immediately processed for pancreatic perfusion. The pancreas was perfused with 3 ml of collagenase P (Roche Diagnostics Corp, 1-1.5 mg/ml, ca 1,000 U/mL) dissolved in HBSS. The collagenase solution was injected by inserting a 30G1/2-G needle into the common bile duct through the joint site of the hepatic duct under a dissecting microscope. After full pancreas distension the tissue was digested by incubation at 37° C. for 30 min in a total of 2 ml of digestion solution. Digested tissue was vigorously shaken and subsequently washed twice in HBSS containing CaCl2. Islets were purified using Falcon cell strainers (Fisher Scientific) and hand-picked under a dissecting microscope. Islets were washed with PBS and used to extract total RNA for qPCR analysis (>40 uM in size) or incubated in HBSS solutions for GSIS assay (average sized between 40 and 70 uM) in a humidified incubator (95% air, 5% CO2) at 37° C.

Cell Lineage Identification qPCR Array

Total RNA was extracted from purified islets by column method using the RNeasy Mini kit (Qiagen, Valencia, Calif.) according to manufacturer's instructions and quantified with the Nanodrop system (Thermo Scientific, Waltham, Mass.). cDNA was obtained from the extracted RNA by retrotranscription with the RT2 First Strand Kit (SABiosciences, Qiagen, Valencia, Calif.) following manufacturer's instructions. The cDNA of each sample was then added to the RT2 SYBR Green qPCR Master Mix and aliquoted for gene expression analysis on specific arrays for the mouse cell lineage identification (PAMM-508Z, SABiosciences). Gene analysis, including significant values and fold changes, was performed with the online tool provided by SABiosciences (www.sabiosciences.com/perarraydataanalysis.php).

Glucose stimulated insulin secretion (GSIS) Assay. Isolated purified islets were incubated in RPMI1640 medium (containing 11 mmol/1 glucose and supplemented with 100 μg/ml streptomycin, 100 μg/ml penicillin, 2 mmol/1 glutamine and 10% FBS) overnight at 37° C. (5% CO2) and then hand-picked into the following medium for GSIS assay: glucose-starved preparation in HEPES buffer (pH 7.4, containing 125 mM NaCl, 5.9 mM KCl, 1.2 mM MgCl$_2$ and 1.28 mM CaCl2, 1 mg/ml BSA) for 45 min and then transferred to the basal glucose conditioned medium (2.5G) (10 islets per well into 500 ul assay medium containing 2.5 mM glucose) for 60 min. Islets were then washed in glucose starvation medium for 5 min and then transferred to glucose stimulation medium (25G) containing 25 mM glucose for 60 min. Medium was collected at the indicated time points (FIG. 1K). The GSIS experiment was performed at least three times and in triplicate in 24-well tissue culture plates with 10 equally-sized islets per well. Washes in between treatments were performed under a dissecting microscope to preserve the number of islet throughout the assay.

Cytokines Profiling. Mouse Cytokine 23-Plex Immunoassay (BIO-RAD, USA) was Used to Perform Simultaneous Quantitative Detection of Multiple Analytes from a Single Serum Sample.

Human Pancreatic Islet Treatments and qPCR:

Cells were treated for 36 h with: Standard medium: Celprogen, M35002-045 for healthy islets and M35001-035 for T1D islets). STS condition (0.5 g/liter of Glucose; 2% FBS), H89 (20 uM) (Sigma-Aldrich), Rapamycin (RAPA) (20 nM) (LC Laboratories, Woburn, Mass., USA), IGF1 (40 ng/ml) (ProSpec, East Brunswick, N.J., USA) and PKA siRNA (Cell signaling, 6574S). For PKA silencing, cells were seeded at 80% of confluence, after 24 h they were transfected for 48 h with 100 nM PKA siRNA (Cell signaling, 6574S) using Lipofectamine RNAiMAx Reagent (ThermoFisher) according to manufacturer instructions. Total RNA was extracted using RNeasy Mini kit (Qiagen) according to the manufacturer's instructions and quantified with the use of the Nanodrop system (Thermo Scientific, Waltham, Mass., USA). Briefly, 1 ug of total RNA was extracted using RNeasy Mini kit and reverse transcribed with SuperScript II Reverse transcriptase (Invitrogen) and the detection of the different transcripts (Ngn3, Sox2, Insulin, and 18S as a reference gene) was carried out using the Kapa sybr fast qPCR kit (KAPA BIO SYSTEMS) according to the instructions of the manufacturer. The expression level were analyzed by quantitative real-time polymerase chain reaction (PCR) on a Roche LightCycler 480II . Gene expression was quantified using the comparative Ct method.

Western Blotting:

Total cell lysates were prepared using the M-Per Protein Extraction Reagent (ThermoScientific, Rockford, Ill., USA) according to manufacturer instructions. Protein concentration was measured with BCA assay (Thermo Scientific). Equal amounts of protein (60 μg) were heat-denatured in lane marker reducing sample buffer (Thermo Scientific), resolved by SDS-PAGE using Novex 4-20% Tris-Glycine MiniProtein Gels (Thermo Scientific), and transferred to PVDF membranes (Millipore, Darmstadt, Germany). The filters were blocked in 5% BSA for 1 h at room temperature and then incubated overnight at 4° C. with primary antibody directed against p70 S6 Kinase and phospho-p70 S6 Kinase (Thr389) (Cell Signaling rabbit mAb #2708, rabbit mAb

9234) and antibody against beta-tubulin (Millipore, #05-661). Peroxidase conjugated IgG (Santa Cruz, Calif., USA) was used as secondary antibody. Membrane-bound immune complexes were detected by ultra-sensitive enhanced chemiluminescence system (Thermo Scientific) on a photon-sensitive film (Hyperfilm ECL, GE Healthcare, Milano, Italy). Quantification was performed by densitometric analysis using ImageJ64 software.

PKA Activity:

PKA activity was measured using the PKA kinase activity kit (Enzo Life Science, Inc. Farmingdale, N.Y., USA) according to manufacturer instructions.

Human Fasting Mimicking Diet:

Human version of FMD is a propriety formulation belonging to L-Nutra (http://l-nutra.com/prolon/). It is a plant-based diet designed to attain fasting-like effects on the serum levels of IGF-I, IGFBP1, glucose and ketone bodies while providing both macro- and micronutrients to minimize the burden of fasting and adverse effects (Brandhorst et al., 2015). Day 1 of the FMD supplies ~4600 kJ (11% protein, 46% fat, 43% carbohydrate), whereas days 2-5 provide ~3000 kJ (9% protein, 44% fat, 47% carbohydrate) per day. The FMD comprises proprietary formulations of vegetable-based soups, energy bars, energy drinks, chip snacks, tea, and a supplement providing high levels of minerals, vitamins and essential fatty acids (FIG. 11). All items to be consumed per day were individually boxed to allow the subjects to choose when to eat while avoiding accidentally consuming components of the following day. For the human subjects, a suggested FMD meal plan was provided that distributes the study foods to be consumed as breakfast, lunch, snacks, and dinner. See lists below for ingredients and supplements:

FMD Ingredients:

Mushroom Soup: Rice flour, Carrot powder, Dried onion, Champignon mushroom powder, Inulin (chicory fiber), Dried champignon mushroom, Salt, Yeast extract, Potato starch, Olive oil, Dried parsley, Natural flavor.

Vegetable Soup: Rice flour, Dried onion, Inulin (chicory fiber), Dried tomato, Dried carrot, Salt, Dried red pepper, Dried leek, Potato starch, Olive oil, Freeze dried basil, Spinach powder, Dried parsley, Natural flavor.

Tomato Soup: Rice flour, Dried tomato powder, Dried onion, dried tomato pieces, dried carrot, chicory fiber, potato starch, olive oil, Salt, Yeast extract, Dried basil, Dried parsley, Natural flavor.

Pumpkin Soup: Pumpkin powder, rice flour, inulin (chicory fiber), dried carrot, salt, yeast extract, potato starch, olive oil, dried onion, dried parsley, natural flavor.

Energy Bar: Almond meal, Macadamia nut butter, Honey, Pecan, Coconut, Flaxseed meal, Coconut oil, Vanilla extract, Sea salt.

Kale Crackers: kale, golden flax seeds, sunflower seeds, cashews, Sesame seeds, nutritional yeast, apple cider vinegar, hemp seeds, pumpkin seeds, sea salt, onion powder, dill week, black pepper Algal Oil Capsule: Algal oil, Gelatin, Glycerin, Purified water, Turmeric, Annatto extract Teas: chamomile, spearmint, or Lemon Energy drink: Purified water, natural vegetable glycerin, polylysine.

Supplements:

Vitamin A (as Beta Carotene), Vitamin C (Ascorbic Acid), Vitamin D (as Cholecalciferol), Vitamin E (as DL-Alpha Tocopherol Acetate), Vitamin K (as Phytonadione), Thiamine (as Thiamine Mononitrate), Riboflavin, Niacin (as Niacinamide), Vitamin B6 (as Pyridoxine HCl), Folic Acid, Vitamin B12 (as Cyanocobalamin), Biotin, Pantothenic Acid (as Calcium-D-Pantothenate), Calcium (as Calcium Carbonate and Tribasic Calcium Phosphate), Iron (as Ferrous Fumarate), Phosphorous (as Tribasic Calcium Phosphate), Iodine (as Potassium Iodine), Magnesium (as Magnesium Oxide), Zinc (Zinc Oxide), Selenium (as Sodium Selenate), Copper (as Cupric Sulfate), Manganese (as Manganese Sulfate), Chromium (as Chromium Picolinate), Molybdenum (as Sodium Molybdate). Proprietary Blend: Beet Root Powder, Spinach Leaf Powder, Tomato Fruit Powder, Carrot Root Powder, Collards Greens Powder, Collards (Kale) Leaf Powder. Other Ingredients: Stearic Acid, Microcrystalline Cellulose, Dicalcium Phosphate, Croscarmellose Sodium, Magnesium Stearate, Silicon Dioxide, Pharmaceutical Glaze.

Metabolic Cages:

Whole-body fat and lean mass was noninvasively measured using LF90 time domain nuclear magnetic resonance scanner (Bruker Optics, Inc). Indirect calorimetric and energy balance parameters including food/water intake, energy expenditure, respiratory exchange ratio (RER), and physical activity were noninvasively assessed for 10 d using metabolic cages (TSE Systems Inc., Chesterfield, Mo., USA).

Quantification and Statistical Analysis.

All experiments reported in FIGS. 1 to 4 were repeated at least three independent times and those in FIGS. 5 and 6 were repeated twice. All samples represent biological replicates. Unless otherwise specified in figure legends, all center values shown in graphs refer to the mean. For statistical significance of the differences between the means of two groups, we used two-tailed Student's t-tests. Statistical significance of differences among multiple groups (≥3) was calculated by performing ANOVA multiple comparisons of the means for each group. No samples or animals were excluded from analysis, and sample size estimates were not used. Animals were randomly assigned to groups. Studies were not conducted blinded, with the exception of all histological analyses.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

Abad, M., Mosteiro, L., Pantoja, C., Canamero, M., Rayon, T., Ors, I., Grana, O., Megias, D., Dominguez, O., Martinez, D., et al. (2013). Reprogramming in vivo produces teratomas and iPS cells with totipotency features. Nature 502, 340-345.

Arakawa, K., Ishihara, T., Oku, A., Nawano, M., Ueta, K., Kitamura, K., Matsumoto, M., and Saito, A. (2001). Improved diabetic syndrome in C57BL/KsJ-db/db mice by oral administration of the Na(+)-glucose cotransporter inhibitor T-1095. British journal of pharmacology 132, 578-586.

Arnes, L., Hill, J. T., Gross, S., Magnuson, M. A., and Sussel, L. (2012). Ghrelin expression in the mouse pancreas defines a unique multipotent progenitor population. PloS one 7, e52026.

Baeyens, L., Lemper, M., Leuckx, G., De Groef, S., Bonfanti, P., Stange, G., Shemer, R., Nord, C., Scheel, D. W., Pan, F. C., et al. (2014). Transient cytokine treatment induces acinar cell reprogramming and regenerates functional beta cell mass in diabetic mice. Nature biotechnology 32, 76-83.

Barnosky, A. R., Hoddy, K. K., Unterman, T. G., and Varady, K. A. (2014). Intermittent fasting vs daily calorie restriction for type 2 diabetes prevention: a review of human findings. Translational research: the journal of laboratory and clinical medicine 164, 302-311.

Blum, B., Roose, A. N., Barrandon, O., Maehr, R., Arvanites, A. C., Davidow, L. S., Davis, J. C., Peterson, Q. P., Rubin, L. L., and Melton, D. A. (2014). Reversal of beta cell de-differentiation by a small molecule inhibitor of the TGFbeta pathway. eLife 3, e02809.

Brandhorst, S., Choi, I. Y., Wei, M., Cheng, C. W., Sedrakyan, S., Navarrete, G., Dubeau, L., Yap, L. P., Park, R., Vinciguerra, M., et al. (2015). A Periodic Diet that Mimics Fasting Promotes Multi-System Regeneration, Enhanced Cognitive Performance, and Healthspan. Cell Metab 22, 86-99.

Brereton, M. F., Iberl, M., Shimomura, K., Zhang, Q., Adriaenssens, A. E., Proks, P., Spiliotis, II, Dace, W., Mattis, K. K., Ramracheya, R., et al. (2014). Reversible changes in pancreatic islet structure and function produced by elevated blood glucose. Nature communications 5, 4639.

Cheng, C. W., Adams, G. B., Perin, L., Wei, M., Zhou, X., Lam, B. S., Da Sacco, S., Mirisola, M., Quinn, D. I., Dorff, T. B., et al. (2014). Prolonged fasting reduces IGF-1/PKA to promote hematopoietic-stem-cell-based regeneration and reverse immunosuppression. Cell stem cell 14, 810-823.

Chera, S., Baronnier, D., Ghila, L., Cigliola, V., Jensen, J. N., Gu, G., Furuyama, K., Thorel, F., Gribble, F. M., Reimann, F., et al. (2014). Diabetes recovery by age-dependent conversion of pancreatic delta-cells into insulin producers. Nature 514, 503-507.

Cnop, M., Welsh, N., Jonas, J. C., Jorns, A., Lenzen, S., and Eizirik, D. L. (2005). Mechanisms of pancreatic beta-cell death in type 1 and type 2 diabetes: many differences, few similarities. Diabetes 54 Suppl 2, S97-107.

Cohen, D. E., and Melton, D. (2011). Turning straw into gold: directing cell fate for regenerative medicine. Nature reviews Genetics 12, 243-252.

Cook, J. R., Matsumoto, M., Banks, A. S., Kitamura, T., Tsuchiya, K., and Accili, D. (2015). A Mutant Allele Encoding DNA-Binding-Deficient Foxo1 Differentially Regulates Hepatic Glucose and Lipid Metabolism. Diabetes.

Dirice, E., Kahraman, S., Jiang, W., El Ouaamari, A., De Jesus, D. F., Teo, A. K., Hu, J., Kawamori, D., Gaglia, J. L., Mathis, D., et al. (2014). Soluble factors secreted by T cells promote beta-cell proliferation. Diabetes 63, 188-202.

Dor, Y., and Glaser, B. (2013). beta-cell dedifferentiation and type 2 diabetes. The New England journal of medicine 368, 572-573.

Fiorina, P., Shapiro, A. M., Ricordi, C., and Secchi, A. (2008). The clinical impact of islet transplantation. American journal of transplantation: official journal of the American Society of Transplantation and the American Society of Transplant Surgeons 8, 1990-1997.

Gomez, D. L., O'Driscoll, M., Sheets, T. P., Hruban, R. H., Oberholzer, J., McGarrigle, J. J., and Shamblott, M. J. (2015). Neurogenin 3 Expressing Cells in the Human Exocrine Pancreas Have the Capacity for Endocrine Cell Fate. PloS one 10, e0133862.

Grunnet, L. G., Aikin, R., Tonnesen, M. F., Paraskevas, S., Blaabjerg, L., Storling, J., Rosenberg, L., Billestrup, N., Maysinger, D., and Mandrup-Poulsen, T. (2009). Proinflammatory cytokines activate the intrinsic apoptotic pathway in beta-cells. Diabetes 58, 1807-1815.

Haeusler, R. A., Hartil, K., Vaitheesvaran, B., Arrieta-Cruz, I., Knight, C. M., Cook, J. R., Kammoun, H. L., Febbraio, M. A., Gutierrez-Juarez, R., Kurland, I. J., et al. (2014). Integrated control of hepatic lipogenesis versus glucose production requires FoxO transcription factors. Nature communications 5, 5190.

Heinrich, C., Spagnoli, F. M., and Berninger, B. (2015). In vivo reprogramming for tissue repair. Nature cell biology 17, 204-211.

Hsu, F. L., Huang, C. F., Chen, Y. W., Yen, Y. P., Wu, C. T., Uang, B. J., Yang, R. S., and Liu, S. H. (2013). Antidiabetic effects of pterosin A, a small-molecular-weight natural product, on diabetic mouse models. Diabetes 62, 628-638.

Johnson, J. D., Han, Z., Otani, K., Ye, H., Zhang, Y., Wu, H., Horikawa, Y., Misler, S., Bell, G. I., and Polonsky, K. S. (2004). RyR2 and calpain-10 delineate a novel apoptosis pathway in pancreatic islets. J Biol Chem 279, 24794-24802.

Kim-Muller, J. Y., Zhao, S., Srivastava, S., Mugabo, Y., Noh, H. L., Kim, Y. R., Madiraju, S. R., Ferrante, A. W., Skolnik, E. Y., Prentki, M., et al. (2014). Metabolic inflexibility impairs insulin secretion and results in MODY-like diabetes in triple FoxO-deficient mice. Cell Metab 20, 593-602.

Kroon, E., Martinson, L. A., Kadoya, K., Bang, A. G., Kelly, O. G., Eliazer, S., Young, H., Richardson, M., Smart, N. G., Cunningham, J., et al. (2008). Pancreatic endoderm derived from human embryonic stem cells generates glucose-responsive insulin-secreting cells in vivo. Nature biotechnology 26, 443-452.

Laviano, A., and Rossi Fanelli, F. Toxicity in chemotherapy—when less is more. The New England journal of medicine 366, 2319-2320.

Lebastchi, J., and Herold, K. C. (2012). Immunologic and metabolic biomarkers of beta-cell destruction in the diagnosis of type 1 diabetes. Cold Spring Harbor perspectives in medicine 2, a007708.

Li, D. S., Yuan, Y. H., Tu, H. J., Liang, Q. L., and Dai, L. J. (2009). A protocol for islet isolation from mouse pancreas. Nature protocols 4, 1649-1652.

Madisen, L., Zwingman, T. A., Sunkin, S. M., Oh, S. W., Zariwala, H. A., Gu, H., Ng, L. L., Palmiter, R. D., Hawrylycz, M. J., Jones, A. R., et al. (2010). A robust and high-throughput Cre reporting and characterization system for the whole mouse brain. Nature neuroscience 13, 133-140.

Maehr, R., Chen, S., Snitow, M., Ludwig, T., Yagasaki, L., Goland, R., Leibel, R. L., and Melton, D. A. (2009). Generation of pluripotent stem cells from patients with type 1 diabetes. Proceedings of the National Academy of Sciences of the United States of America 106, 15768-15773.

Matthews, D. R. (2001). Insulin resistance and beta-cell function—a clinical perspective. Diabetes, obesity & metabolism 3 Suppl 1, S28-33.

Matthews, D. R., Hosker, J. P., Rudenski, A. S., Naylor, B. A., Treacher, D. F., and Turner, R. C. (1985). Homeostasis model assessment: insulin resistance and beta-cell function from fasting plasma glucose and insulin concentrations in man. Diabetologia 28, 412-419.

McKnight, K. D., Wang, P., and Kim, S. K. (2010). Deconstructing pancreas development to reconstruct human islets from pluripotent stem cells. Cell stem cell 6, 300-308.

Meier, J. J., Butler, A. E., Saisho, Y., Monchamp, T., Galasso, R., Bhushan, A., Rizza, R. A., and Butler, P. C. (2008). Beta-cell replication is the primary mechanism subserving the postnatal expansion of beta-cell mass in humans. Diabetes 57, 1584-1594.

Milanesi, A., Lee, J. W., Li, Z., Da Sacco, S., Villani, V., Cervantes, V., Perin, L., and Yu, J. S. (2012). beta-Cell regeneration mediated by human bone marrow mesenchymal stem cells. PloS one 7, e42177.

Mu, J., Woods, J., Zhou, Y. P., Roy, R. S., Li, Z., Zycband, E., Feng, Y., Zhu, L., Li, C., Howard, A. D., et al. (2006). Chronic inhibition of dipeptidyl peptidase-4 with a sitagliptin analog preserves pancreatic beta-cell mass and function in a rodent model of type 2 diabetes. Diabetes 55, 1695-1704.

Pagliuca, F. W., Millman, J. R., Gurtler, M., Segel, M., Van Dervort, A., Ryu, J. H., Peterson, Q. P., Greiner, D., and Melton, D. A. (2014). Generation of functional human pancreatic beta cells in vitro. Cell 159, 428-439.

Pipeleers, D., Keymeulen, B., Chatenoud, L., Hendrieckx, C., Ling, Z., Mathieu, C., Roep, B., and Ysebaert, D. (2002). A view on beta cell transplantation in diabetes. Ann N Y Acad Sci 958, 69-76.

Rabinovitch, A. (1998). An update on cytokines in the pathogenesis of insulin-dependent diabetes mellitus. Diabetes/metabolism reviews 14, 129-151.

Raffaghello, L., Lee, C., Safdie, F. M., Wei, M., Madia, F., Bianchi, G., and Longo, V. D. (2008). Starvation-dependent differential stress resistance protects normal but not cancer cells against high-dose chemotherapy. Proceedings of the National Academy of Sciences of the United States of America 105, 8215-8220.

Sneddon, J. B., Borowiak, M., and Melton, D. A. (2012). Self-renewal of embryonic-stem-cell-derived progenitors by organ-matched mesenchyme. Nature 491, 765-768.

Stanger, B. Z. (2008). HNF4A and diabetes: injury before insult? Diabetes 57, 1461-1462. Talchai, C., Xuan, S., Lin, H. V., Sussel, L., and Accili, D. (2012). Pancreatic beta cell dedifferentiation as a mechanism of diabetic beta cell failure. Cell 150, 1223-1234.

Talchai, S. C., and Accili, D. (2015). Legacy Effect Of Foxo1 In Pancreatic Endocrine Progenitors On Adult beta-cell Mass And Function. Diabetes.

Teta, M., Long, S. Y., Wartschow, L. M., Rankin, M. M., and Kushner, J. A. (2005). Very slow turnover of beta-cells in aged adult mice. Diabetes 54, 2557-2567.

Tonne, J. M., Sakuma, T., Deeds, M. C., Munoz-Gomez, M., Barry, M. A., Kudva, Y. C., and Ikeda, Y. Global gene expression profiling of pancreatic islets in mice during streptozotocin-induced beta-cell damage and pancreatic Glp-1 gene therapy. Dis Model Mech 6, 1236-1245.

Van de Casteele, M., Leuckx, G., Baeyens, L., Cai, Y., Yuchi, Y., Coppens, V., De Groef, S., Eriksson, M., Svensson, C., Ahlgren, U., et al. (2013). Neurogenin 3+ cells contribute to beta-cell neogenesis and proliferation in injured adult mouse pancreas. Cell death & disease 4, e523.

Villani, V., Milanesi, A., Sedrakyan, S., Da Sacco, S., Angelow, S., Conconi, M. T., Di Liddo, R., De Filippo, R., and Perin, L. (2014). Amniotic fluid stem cells prevent beta-cell injury. Cytotherapy 16, 41-55.

Wang, S., Jensen, J. N., Seymour, P. A., Hsu, W., Dor, Y., Sander, M., Magnuson, M. A., Serup, P., and Gu, G. (2009). Sustained Neurog3 expression in hormone-expressing islet cells is required for endocrine maturation and function. Proceedings of the National Academy of Sciences of the United States of America 106, 9715-9720.

Wang, Z., York, N. W., Nichols, C. G., and Remedi, M. S. Pancreatic beta Cell Dedifferentiation in Diabetes and Redifferentiation following Insulin Therapy. Cell Metab 19, 872-882.

Wang, Z., York, N. W., Nichols, C. G., and Remedi, M. S. (2014). Pancreatic beta cell dedifferentiation in diabetes and redifferentiation following insulin therapy. Cell Metab 19, 872-882.

Weinberg, N., Ouziel-Yahalom, L., Knoller, S., Efrat, S., and Dor, Y. (2007). Lineage tracing evidence for in vitro dedifferentiation but rare proliferation of mouse pancreatic beta-cells. Diabetes 56, 1299-1304.

Weir, G. C., Aguayo-Mazzucato, C., and Bonner-Weir, S. (2013). beta-cell dedifferentiation in diabetes is important, but what is it? Islets 5, 233-237.

Wu, K. K., and Huan, Y. (2008). Streptozotocin-induced diabetic models in mice and rats. Curr Protoc Pharmacol Chapter 5, Unit 5 47.

Xiao, X., Chen, Z., Shiota, C., Prasadan, K., Guo, P., El-Gohary, Y., Paredes, J., Welsh, C., Wiersch, J., and Gittes, G. K. (2013). No evidence for beta cell neogenesis in murine adult pancreas. The Journal of clinical investigation 123, 2207-2217.

Xu, J., Du, Y., and Deng, H. (2015). Direct lineage reprogramming: strategies, mechanisms, and applications. Cell stem cell 16, 119-134.

Xu, X., D'Hoker, J., Stange, G., Bonne, S., De Leu, N., Xiao, X., Van de Casteele, M., Mellitzer, G., Ling, Z., Pipeleers, D., et al. (2008). Beta cells can be generated from endogenous progenitors in injured adult mouse pancreas. Cell 132, 197-207.

Yilmaz, O. H., Katajisto, P., Lamming, D. W., Gultekin, Y., Bauer-Rowe, K. E., Sengupta, S., Birsoy, K., Dursun, A., Yilmaz, V. O., Selig, M., et al. (2012). mTORC1 in the Paneth cell niche couples intestinal stem-cell function to calorie intake. Nature 486, 490-495.

Yin, D., Tao, J., Lee, D. D., Shen, J., Hara, M., Lopez, J., Kuznetsov, A., Philipson, L. H., and Chong, A. S. (2006). Recovery of islet beta-cell function in streptozotocin-induced diabetic mice: an indirect role for the spleen. Diabetes 55, 3256-3263.

Zhernakova, A., Alizadeh, B. Z., Eerligh, P., Hanifi-Moghaddam, P., Schloot, N. C., Diosdado, B., Wijmenga, C., Roep, B. O., and Koeleman, B. P. (2006). Genetic variants of RANTES are associated with serum RANTES level and protection for type 1 diabetes. Genes and immunity 7, 544-549.

Zhou, Q., Brown, J., Kanarek, A., Raj agopal, J., and Melton, D. A. (2008). In vivo reprogramming of adult pancreatic exocrine cells to beta-cells. Nature 455, 627-632.

What is claimed is:

1. A method for promoting pancreatic β-cell regeneration comprising:
   identifying a subject in need of human pancreatic β-cell regeneration; and
   administering a fasting mimicking diet (FMD) for a predetermined period of time and administering a Protein Kinase A (PKA) inhibitor and administering a Tor inhibitor to the subject to promote pancreatic β-cell regeneration, wherein the fasting mimicking diet provides:
less than 40 grams of sugar for day 1;
less than 30 grams of sugar for days 2 to 5 and any remaining days;
less than 28 grams of protein for day 1;
less than 18 grams of protein for days 2 to 5 and any remaining days;
20-100 grams of monounsaturated fats for day 1;
6-30 grams of polyunsaturated fats for day 1;
2-12 grains of saturated fats for day 1;
10-50 grams of monounsaturated fats for days 2 to 5 and any remaining days;
3-15 grams of polyunsaturated fats for days 2 to 5 and any remaining days;
1-30 grams of saturated fats for days 2 to 5, or any remaining days; and
a micronutrient composition on each day and any remaining days, and wherein the PKA inhibitor and/or the Tor inhibitor is select from the group consisting of an antibody, antagonist or small molecule which blocks IGF-1R, rapamycin which inhibits mTOR, H89 which inhibits PKA, and combinations thereof.

2. The method of claim 1 the subject is diagnosed with diabetes type 1 or diabetes type 2.

3. The method of claim 1 wherein somatic cell dedifferentiation and/or reprogramming is promoted.

4. The method of claim 1 wherein gastrointestinal cell dedifferentiation and/or reprogramming is promoted.

5. The method of claim 1 wherein the fasting mimicking diet promotes muscle rejuvenation associated with stem cell generation.

6. The method claim 5 wherein insulin resistance is decreased.

7. The method of claim 5 wherein hyperglycemia is reduced.

8. The method of claim 1 wherein the predetermined period of time is 5 to 10 days.

9. The method of claim 1 wherein the fasting mimicking diet provides:
8-25 kcal per kilogram body weight for each diet day:
less than 30 grams of sugar for each diet day;
less than 18 grams of protein for each diet day; and
9-30 grams of monounsaturated fats for each diet day, 2.5-9 grams of polyunsaturated fats for each diet day and 1-10 grams of saturated fats for each diet day.

10. The method of claim 1 wherein the fasting mimicking diet provides:
5-8 kcal per kilogram body weight for each diet day;
less than 20 grams of sugar for each diet day;
less than 12 grams of protein for each diet day; and
6.5-10 grams of monounsaturated fats for each diet day, 2.5-4.5 grams of polyunsaturated fats for each diet day and 1.5-4 grams of saturated fats for each diet day.

11. The method of claim 1 wherein the fasting mimicking diet provides:
0-3 kcal per kilogram body weight for each diet day;
less than 5 grams of sugar for each diet day;
less than 3 grams of protein for each diet day; and
less than 2.5 grams of monounsaturated fats for each diet day, less than 1 grams of polyunsaturated fats for each diet day and less than 1 grams of saturated fats for each diet day.

12. The method of claim 1 wherein the fasting mimicking diet is administered from a diet package, the diet package comprising:

a first set of rations for a first diet to be administered for a predetermined time period to the subject with administration schedule, the first diet providing:
less than 40 grams of sugar for day 1;
less than 30 grams of sugar for days 2 to 5 and any remaining days;
less than 28 grams of protein for day 1;
less than 18 grams of protein for days 2 to 5 and any remaining days;
20-100 grams of monounsaturated fats for day 1;
6-30 grams of polyunsaturated fats for day 1;
2-12 grams of saturated fats for day 1;
10-50 grams of monounsaturated fats for days 2 to 5 and any remaining days;
3-15 grams of polyunsaturated fats for days 2 to 5 and any remaining days;
1-12 grams of saturated fats for days 2 to 5, or any remaining days; and
a micronutrient composition on each day and any remaining days; and
instructions for administering the diet package to the subject for promoting pancreatic β-cell regeneration and somatic cell reprogramming, the instructions including the administration schedule.

13. The method of claim 12 wherein the fasting mimicking diet provides:
8-10 kcal per kilogram body weight for each diet day:
less than 30 grams of sugar for each diet day;
less than 18 grams of protein for each diet day; and
9-15 grams of monounsaturated fats for each diet day, 2.5-4.5 grams of polyunsaturated fats for each diet day and 1-5.5 grams of saturated fats for each diet day.

14. The method of claim 12 wherein the fasting mimicking diet provides:
5-8 kcal per kilogram body weight for each diet day;
less than 20 grams of sugar for each diet day;
less than 12 grams of protein for each diet day; and
6.5-10 grams of monounsaturated fats for each diet day, 2.5-4.5 grams of polyunsaturated fats for each diet day and 1.5-4 grams of saturated fats for each diet day.

15. The method of claim 12 wherein the fasting mimicking diet provides:
0-3 kcal per kilogram body weight for each diet day;
less than 5 grams of sugar for each diet day;
less than 3 grams of protein for each diet day; and
less than 2.5 grams of monounsaturated fats for each diet day, less than 1 grams of polyunsaturated fats for each diet day and less than 1 grams of saturated fats for each diet day.

16. The method of claim 12 further comprising a second set of rations for a second diet to be administered to the subject for a second time period, the second diet providing an overall calorie consumption that is within 10 percent of a subject's normal calorie consumption for 25 to 26 days following the first diet.

17. The method of claim 12 wherein the first set of rations provide 400-800 mg of calcium per day for days 1-5; 7.2-14.4 mg of iron per day for days 1-5; 200-400 mg of magnesium per day for days 1-5; 1-2 mg of copper per day for days 1-5; 1-2 mg of manganese per day for days 1-5; and 3.5-7 mcg of selenium per day for days 1-5.

18. The method of claim 12 wherein the first set of rations provide 2-4 mg of Vitamin B1 per day for days 1-5; 2-4 mg of Vitamin B2 per day for days 1-5; 20-30 mg of Vitamin B3 per day for days 1-5; 1-1.5 mg of Vitamin B5 per day for days 1-5; 2-4 mg of Vitamin B6 per day for days 1-5; 240-480 mcg of Vitamin B9 per day for days 1-5; 600-1000

IU of Vitamin D per day for days 1-5; 14-30 mg of Vitamin E per day for days 1-5; over 80 mcg of Vitamin K per day for days 1-5; and 16-25 mcg Vitamin B12 are provided during the predetermined time period.

19. The method of claim 1 wherein the PKA inhibitor is select from the group consisting of H89, antibodies which blocks IGF-IR, PKA siRNA, and combinations thereof.

20. The method of claim 1 wherein the PKA it inhibitor is H89.

21. The method of claim 1 wherein the PKA inhibitor is an antibody which blocks IGF-IR.

22. The method of claim 1 wherein the Tor inhibitor is rapamycin or an antibody which blocks IGF-IR.

23. The method of claim 1 wherein the Tor inhibitor is rapamycin.

24. The method of claim 1 wherein the Tor inhibitor is rapamycin and the PKA inhibitor is H89.

25. The method of claim 11 wherein the first set of rations provides 600 mg of Docosahexaenoic acid (DHA, algae-derived) during the predetermined time period.

26. The method of claim 12 further comprising a component having Vitamin A in an amount of 900-1600 IU; Ascorbic Acid in an amount of 10-20 mg; calcium carbonate in an amount of 60-100 mg; ferrous fumarate in an amount of 3-6 mg; cholecalciferol in an amount of 0.001-0.005 mg; dl-alpha tocopheryl acetate in an amount 3-7 mg; phytonadione in an amount of 0.1-0.04 mg; thiamine mononitrate in an amount of 0.15-0.5 mg; riboflavin in an amount 0.2-0.6 mg; and niacinamide in an amount of 3-7 mg.

27. The method of claim 26 further comprising a component having calcium pantothenate in an amount of 1.5-4.0 mg; pyridoxine hydrochloride in an amount of 0.3-0.7 mg; biotin in an amount of 0.01-0.02 mg; folic acid in an amount of 0.07-0.14 mg; cyanocobalamin in an amount of 0.001-0.002 mg; chromium picolinate in an amount of 0.014-0.022 mg; cupric sulfate in an amount of 0.18-0.32 mg; potassium iodide in an amount of 0.03-0.045 mg; magnesium oxide in an amount of 20-32 mg; manganese sulfate of 0.3-0.7 mg; sodium molybdate in an amount of 0.014-0.023 mg; sodium selenate in an amount of 0.014-0.023 mg; and zinc oxide in an amount of 3-5 mg.

* * * * *

UNITED STATES PATENT AND TRADEMARK OFFICE
CERTIFICATE OF CORRECTION

PATENT NO. : 10,660,932 B2
APPLICATION NO. : 15/433906
DATED : May 26, 2020
INVENTOR(S) : Valter D. Longo et al.

It is certified that error appears in the above-identified patent and that said Letters Patent is hereby corrected as shown below:

In the Claims

Column 39, Lines 20-21, Claim 1:
After "and/or Tor inhibitor is"
Delete "select" and
Insert -- selected --.

Column 39, Line 25, Claim 2:
After "The method of claim 1"
Insert -- wherein --.

Column 39, Line 62, Claim 11:
After "less than"
Delete "1 grams" and
Insert -- 1 gram --.

Column 39, Line 63, Claim 11:
After "less than"
Delete "1 grams" and
Insert -- 1 gram --.

Column 40, Line 47, Claim 15:
After "less than"
Delete "1 grams" and
Insert -- 1 gram --.

Column 41, Lines 5-6, Claim 19:
After "wherein the PKA inhibitor is"
Delete "select" and
Insert -- selected --.

Signed and Sealed this
Seventeenth Day of November, 2020

Andrei Iancu
*Director of the United States Patent and Trademark Office*